United States Patent
He et al.

(10) Patent No.: US 11,834,517 B2
(45) Date of Patent: Dec. 5, 2023

(54) BRANCHED PEPTIDES FOR ENZYMATIC ASSEMBLY AND MITOCHONDRIA DRUG DELIVERY

(71) Applicant: BRANDEIS UNIVERSITY, Waltham, MA (US)

(72) Inventors: Hongjian He, Waltham, MA (US); Bing Xu, Newton, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 0 days.

(21) Appl. No.: 17/537,418

(22) Filed: Nov. 29, 2021

(65) Prior Publication Data

US 2022/0112240 A1   Apr. 14, 2022

Related U.S. Application Data

(63) Continuation-in-part of application No. 16/648,295, filed as application No. PCT/US2018/051521 on Sep. 18, 2018, now Pat. No. 11,191,724.

(60) Provisional application No. 63/123,230, filed on Dec. 9, 2020, provisional application No. 62/560,094, filed on Sep. 18, 2017.

(51) Int. Cl.
| | |
|---|---|
| *C07K 7/06* | (2006.01) |
| *C07K 7/08* | (2006.01) |
| *A61P 35/00* | (2006.01) |
| *C07K 19/00* | (2006.01) |
| *A61P 9/00* | (2006.01) |
| *A61K 9/107* | (2006.01) |

(52) U.S. Cl.
CPC .............. *C07K 7/06* (2013.01); *A61K 9/1075* (2013.01); *A61P 9/00* (2018.01); *A61P 35/00* (2018.01); *C07K 7/08* (2013.01); *C07K 19/00* (2013.01)

(58) Field of Classification Search
None
See application file for complete search history.

(56) References Cited

U.S. PATENT DOCUMENTS

| | | | |
|---|---|---|---|
| 6,906,176 | B2 | 6/2005 | Ley et al. |
| 11,191,724 | B2 | 12/2021 | He et al. |
| 2006/0165714 | A1 | 7/2006 | Kern et al. |
| 2008/0268015 | A1 | 10/2008 | Gron et al. |
| 2012/0142616 | A1 | 6/2012 | Gao et al. |
| 2014/0148410 | A1 | 5/2014 | Xu |
| 2014/0235550 | A1 | 8/2014 | Gao et al. |
| 2016/0016994 | A1 | 1/2016 | Xu et al. |
| 2017/0007696 | A1 | 1/2017 | Zhao et al. |
| 2017/0037082 | A1 | 2/2017 | Xu et al. |
| 2017/0119910 | A1 | 5/2017 | Du et al. |
| 2018/0037605 | A1 | 2/2018 | Du et al. |
| 2018/0346630 | A1 | 12/2018 | Zhang et al. |
| 2019/0224330 | A1 | 7/2019 | Wang et al. |
| 2020/0023065 | A1 | 1/2020 | Xu |
| 2020/0281854 | A1 | 9/2020 | He et al. |

FOREIGN PATENT DOCUMENTS

| | | |
|---|---|---|
| WO | 2010/151644 A2 | 12/2010 |
| WO | 2011/022056 A2 | 2/2011 |
| WO | 2012/166705 A2 | 12/2012 |
| WO | 2012/166706 A2 | 12/2012 |
| WO | 2014/074789 A1 | 5/2014 |
| WO | 2014/138367 A1 | 9/2014 |
| WO | 2015/116242 A1 | 8/2015 |
| WO | 2015/157530 A2 | 10/2015 |
| WO | 2015/157535 A2 | 10/2015 |
| WO | 2016/138433 A1 | 9/2016 |
| WO | 2017/189996 A1 | 11/2017 |
| WO | 2018/129171 A1 | 7/2018 |
| WO | 2019/035928 A1 | 2/2019 |
| WO | 2019/055988 A1 | 3/2019 |

OTHER PUBLICATIONS

Final Office Action for U.S. Appl. No. 16/648,295 (dated Jun. 16, 2021).
Non-Final Office Action for U.S. Appl. No. 16/648,295 (dated Jan. 28, 2021).
He et al., "Branched Peptides for Enzymatic Supramolecular Hydrogelation," Chem. Commun. 54:86-89 (2018).
Kim, et al., "Substrate Specificities of Porcine and Bovine Enteropeptidases towards the Peptide Val-(Asp)4-Lys-Ile-Val-Gly and its Analogs," Biosci. Biotechnol. Biochem. 72(3):905-908 (2008).
Waugh, D., "An Overview of Enzymatic Reagents for the Removal of Affinity Tags," Protein Expres. Purif. 80(2): 283-293 (2011).
Nguyen et al., "Modulation of the Protein Kinase Cdelta Interaction with the "d" Subunit of F1F0-ATP Synthase in Neonatal Cardiac Myocytes: Development of Cell-Permeable, Mitochondrially Targeted Inhibitor and Facilitator Peptides," J. Biol. Chem. 285(29):22164-22173 (2010).

(Continued)

*Primary Examiner* — Thomas S Heard
(74) *Attorney, Agent, or Firm* — Troutman Pepper Hamilton Sanders LLP (Rochester)

(57) ABSTRACT

The present invention relates to a branched peptide that includes a first peptide chain and a second peptide chain having its C-terminal amino acid covalently linked to a sidechain of an amino acid residue of the first peptide chain, wherein the first peptide chain includes a plurality of aromatic amino acids and, optionally, an aromatic group linked to an amino terminus of the first peptide chain; and the second peptide chain includes a plurality of hydrophilic amino acids and an enzyme cleavage site. Pharmaceutical compositions containing the branched peptide and one or more therapeutic agents in an aqueous medium are disclosed, where the branched peptides form micelle structures in the aqueous medium. Methods of using the pharmaceutical composition to deliver therapeutic agents, and for treating various disease conditions are also described.

21 Claims, 20 Drawing Sheets
Specification includes a Sequence Listing.

(56) References Cited

OTHER PUBLICATIONS

International Search Report and Written Opinion for corresponding PCT Application No. PCT/US2018/051521, dated Jan. 18, 2019.
Mei et al., "Enzyme-instructed Self-Assembly of Taxol Promotes Axonal Branching," Nanoscale 7(38):15605-15608 (2015).

FIGS. 5A-D

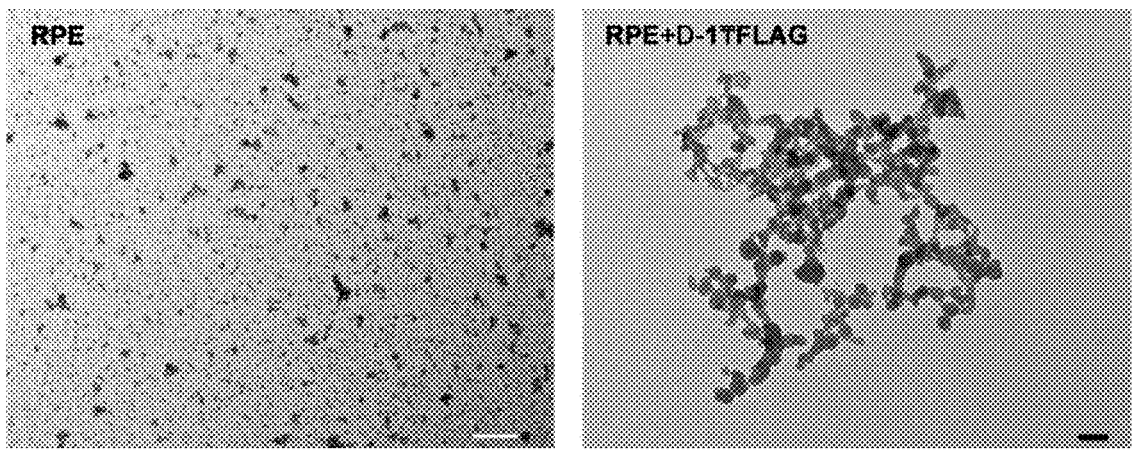
*FIG. 6*
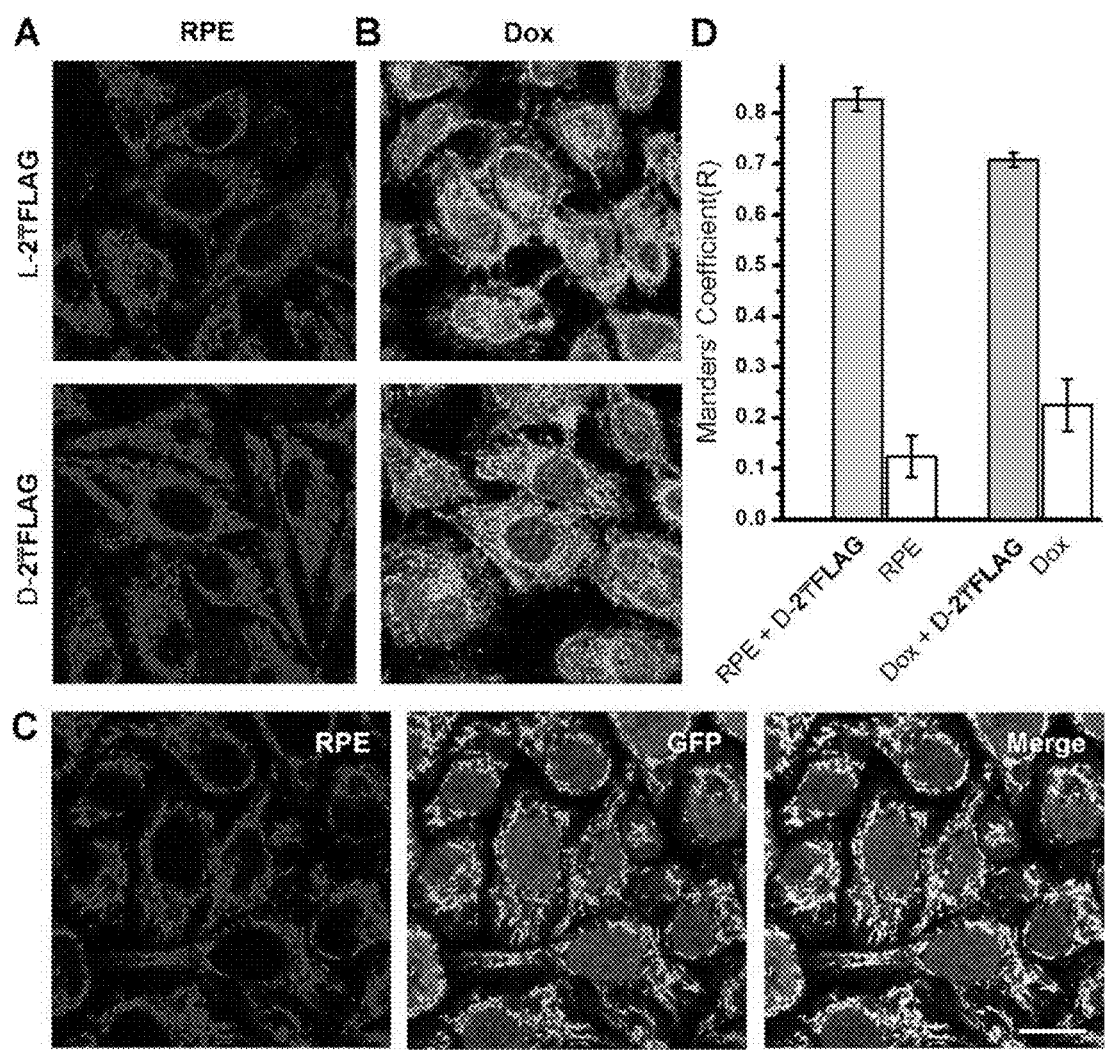
*FIGS. 7A-D*

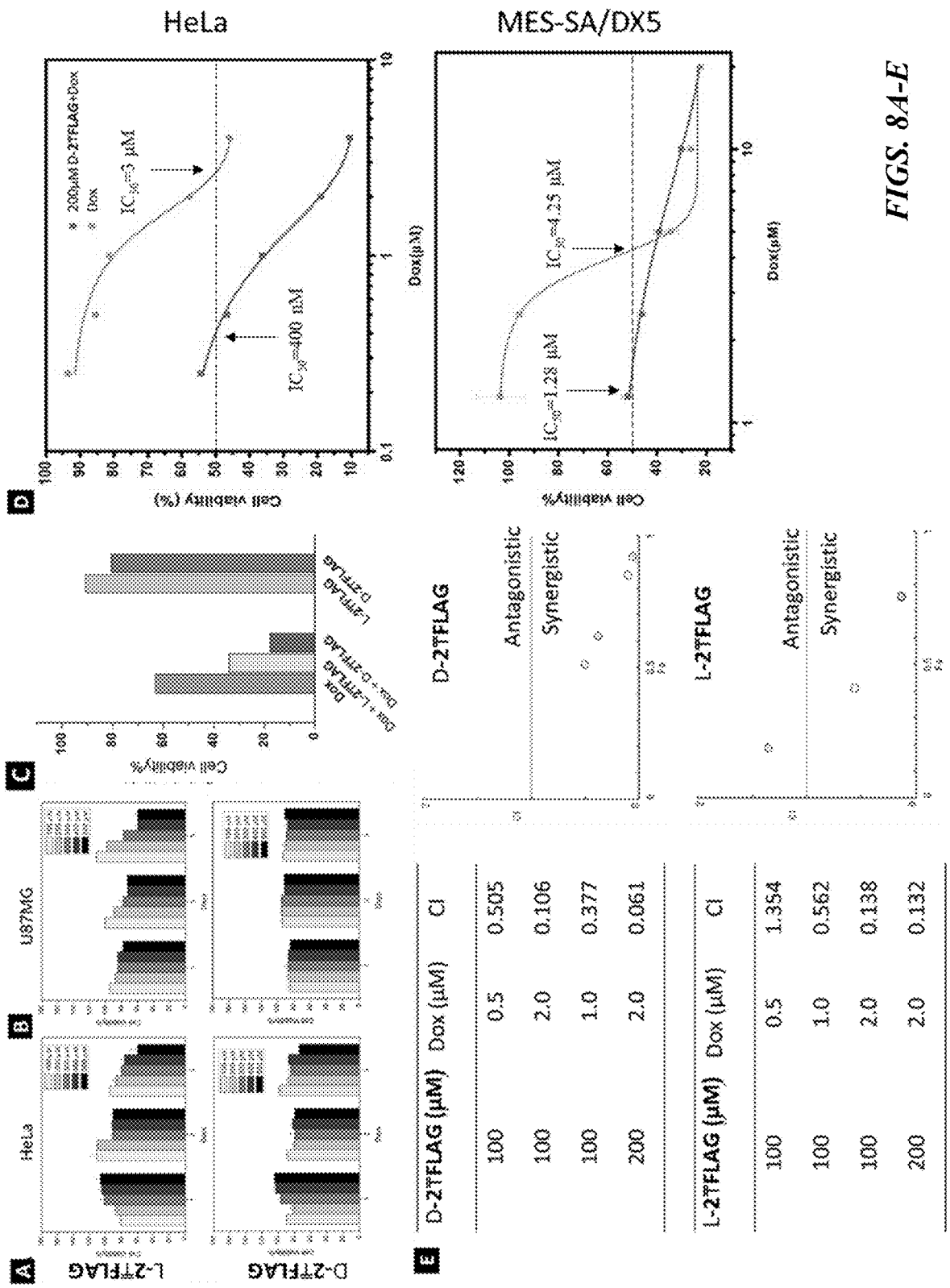
FIGS. 8A-E

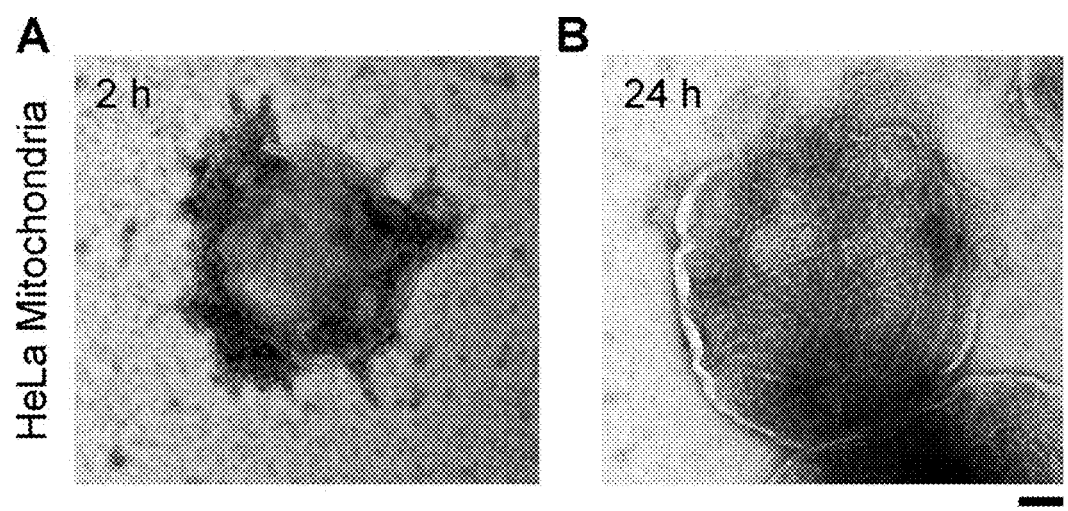
*FIGS. 9A-B*
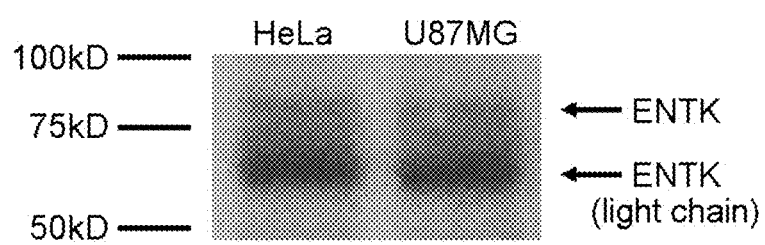
*FIG. 10*
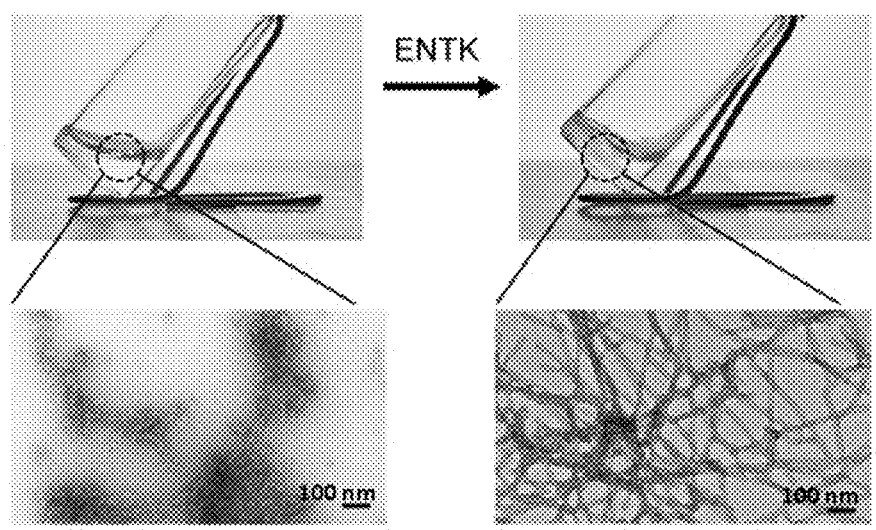
*FIG. 11*

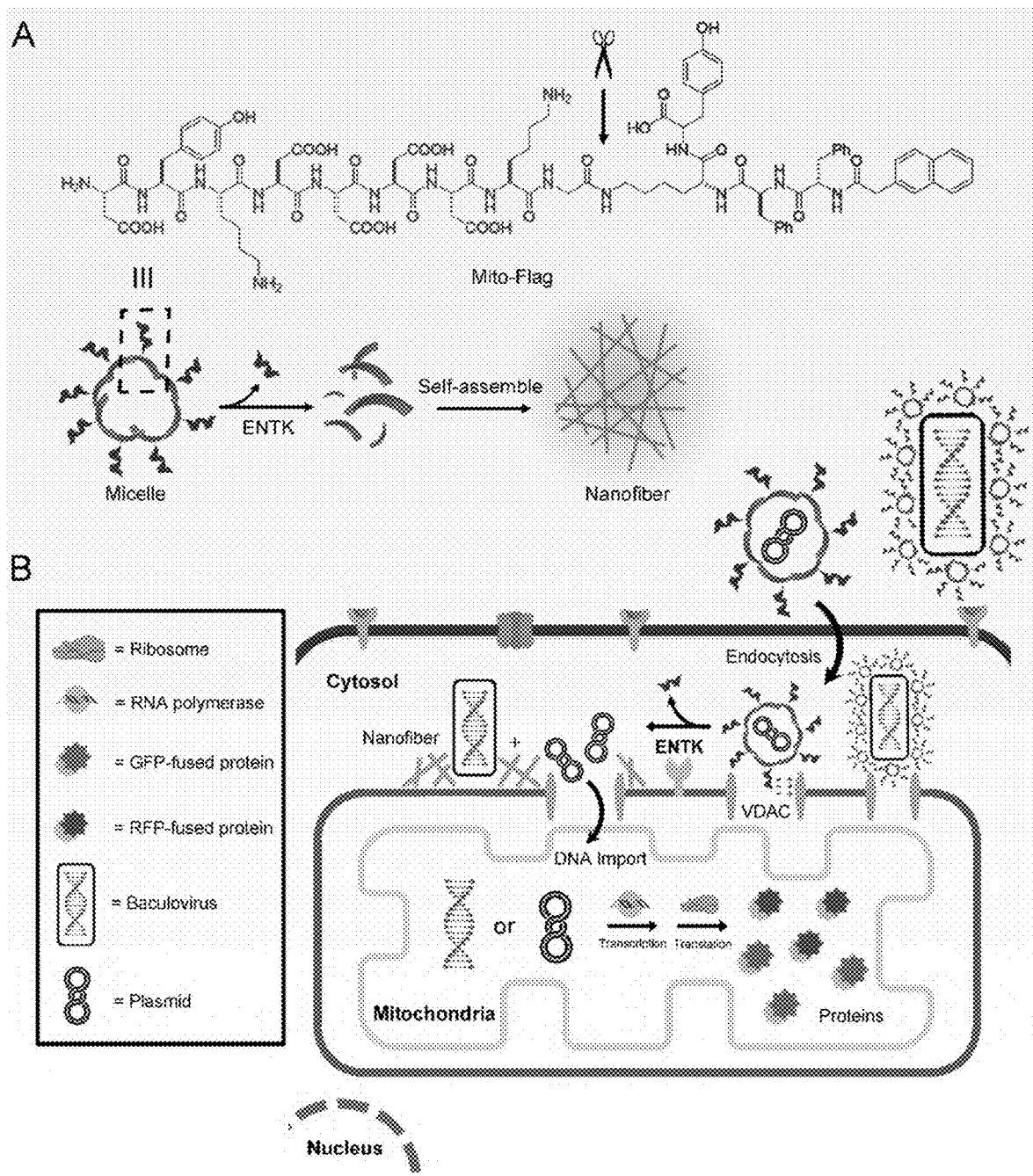
FIGS. 21A-B

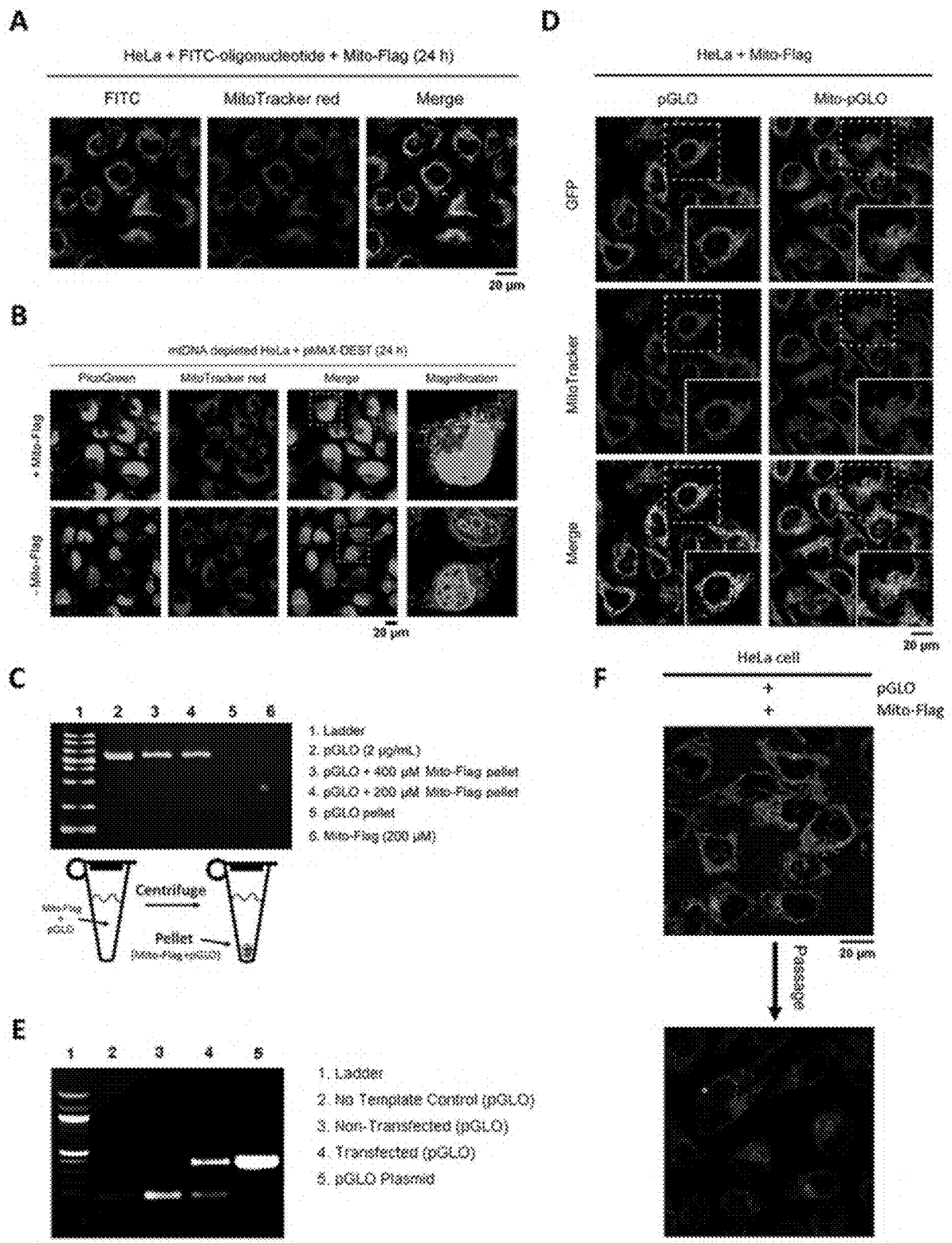
*FIGS. 22A-F*

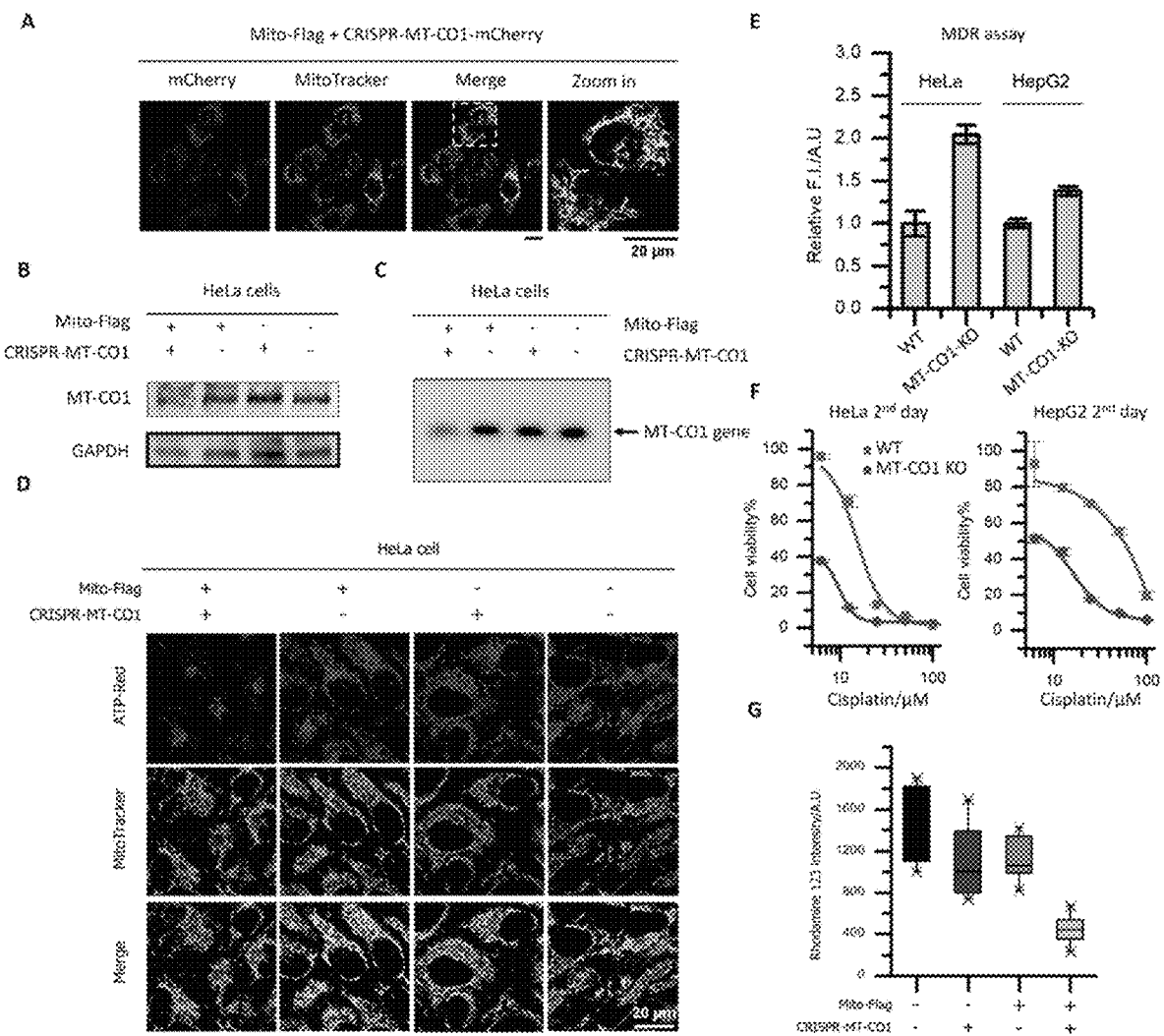
FIGS. 23A-G

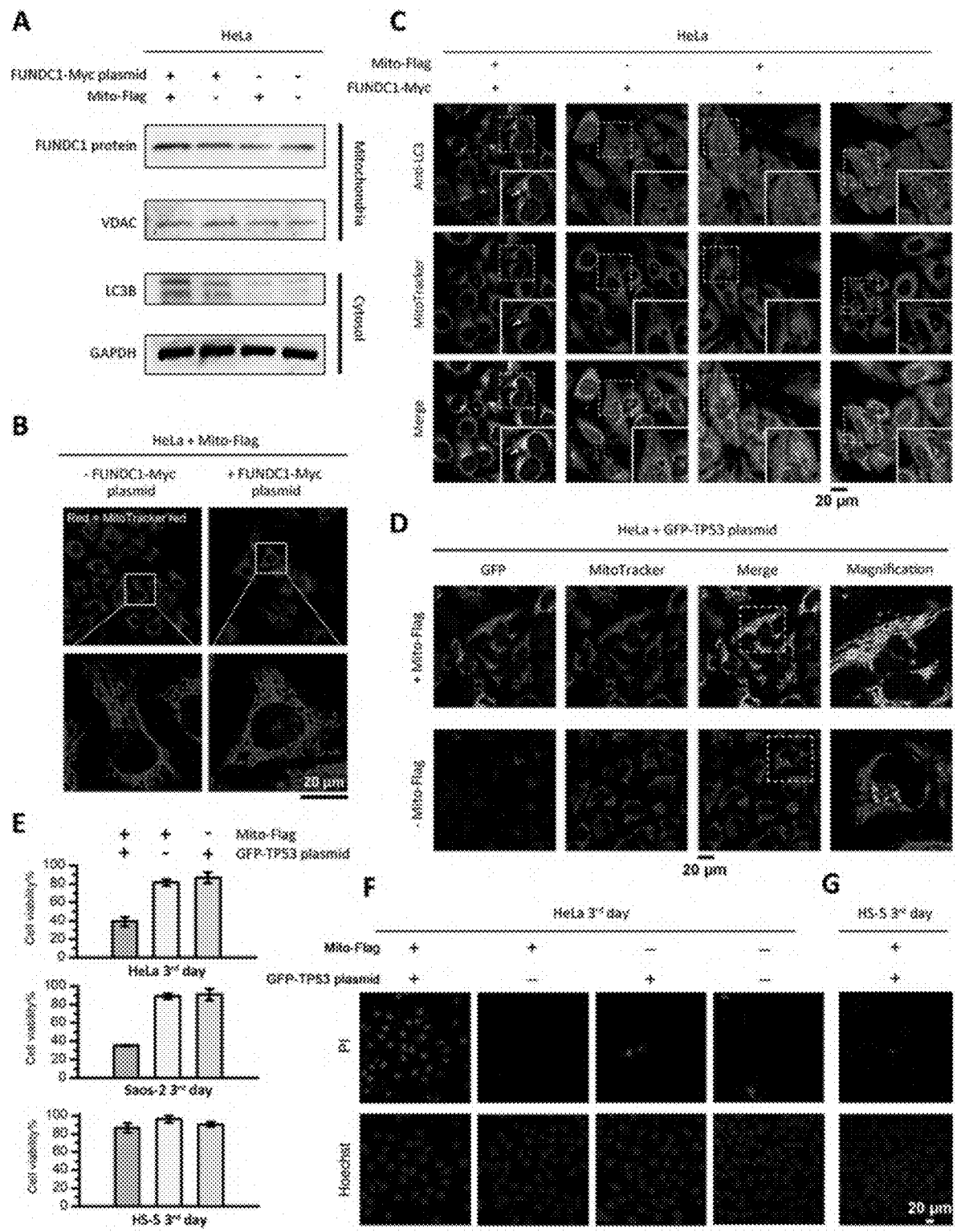
FIGS. 24A-G

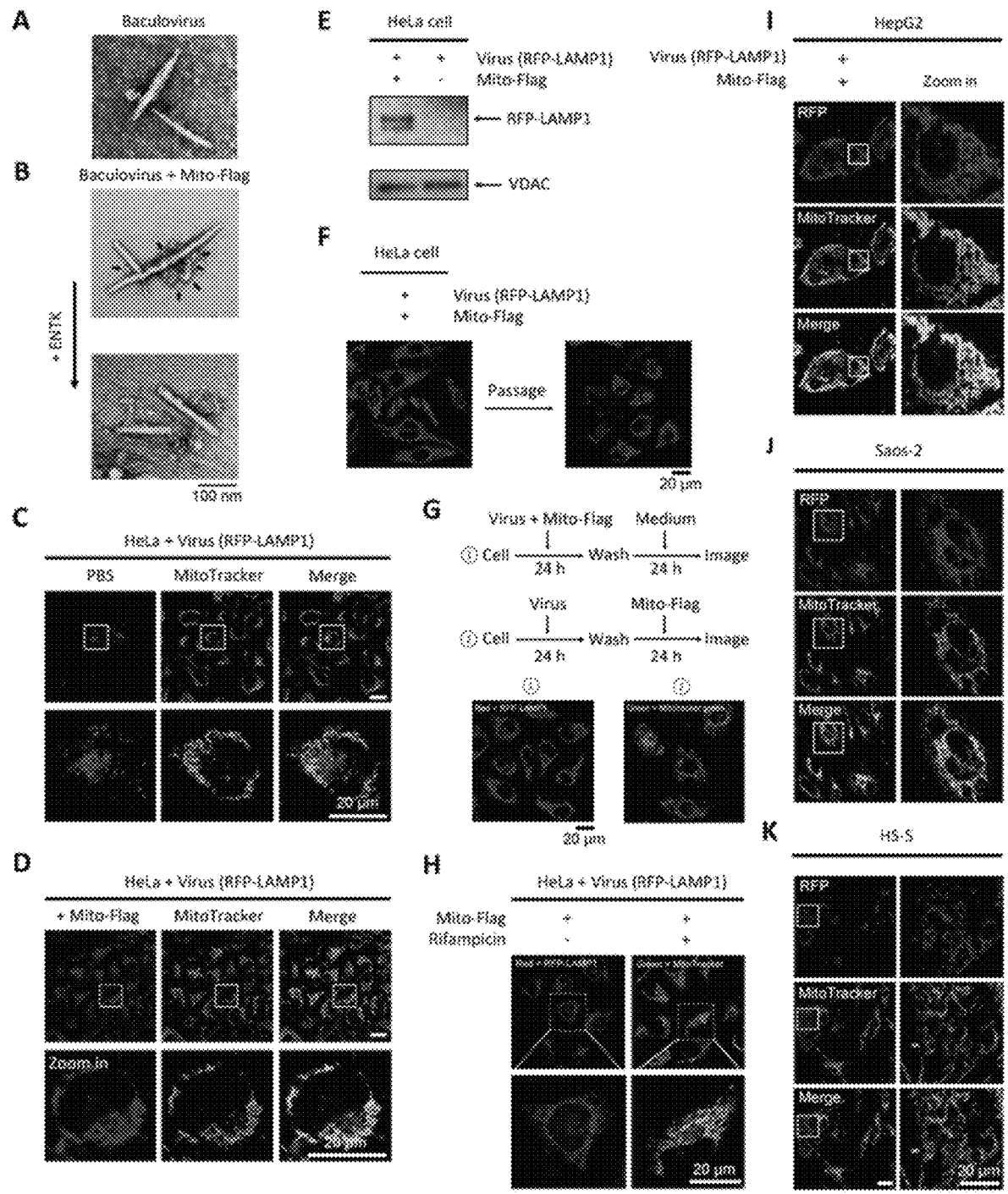
FIGS. 25A-K

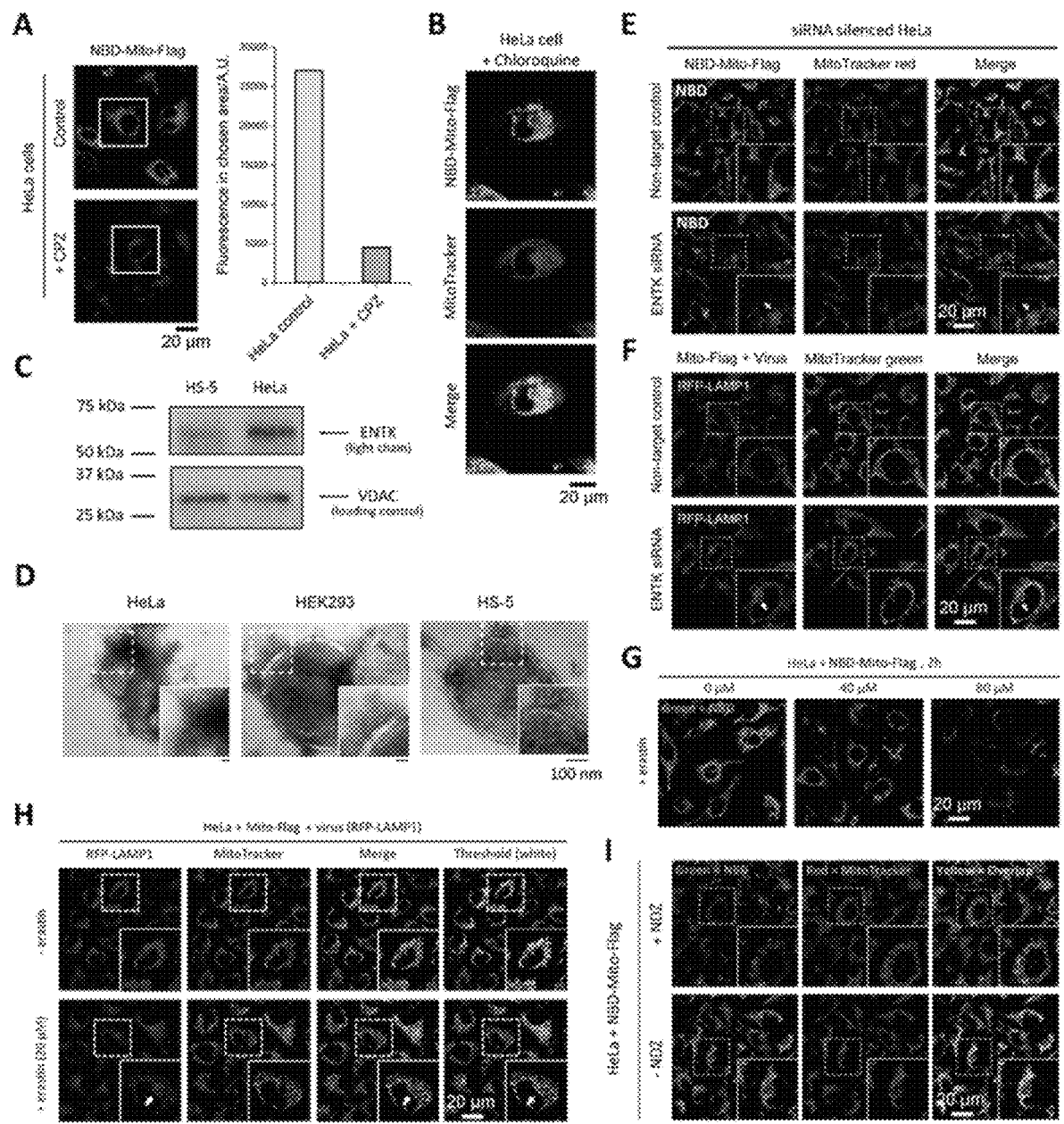
FIGS. 26A-I pGLO:

forward: G G A A A C T A C C T G T T C C A T G G C C A A C A C T T G T C A C T A   SEQ ID NO: 83
reverse: C C T T T G A T G G A C A A G G T A C C G G T T G T G A A C A G T G A T   SEQ ID NO: 84

C A C A T G G C A T G G A T G A A C T A T A C A A A T A G T T A   (boxed: T A A / A T T)

Mito-pGLO:

forward: G G A A A C T A C C T G T T C C A T G G C C A A C A C T T G T C A C T A   SEQ ID NO: 85
reverse: C C T T T G A T G G A C A A G G T A C C G G T T G T G A A C A G T G A T   SEQ ID NO: 86

C A C A T G G C A T G G A T G A G C T C T A C A A A G G T T C C   (boxed: A G G / T C C)

*FIG. 27*

BRANCHED PEPTIDES FOR ENZYMATIC ASSEMBLY AND MITOCHONDRIA DRUG DELIVERY

This application is a continuation-in-part of U.S. patent application Ser. No. 16/648,295, which is a national stage application under 35 U.S.C. § 371 of PCT Application No. PCT/US2018/051521, filed Sep. 18, 2018, which claims the priority benefit of U.S. Provisional Patent Application Ser. No. 62/560,094, filed Sep. 18, 2017. This application also claims the priority benefit of U.S. Provisional Patent Application Ser. No. 63/123,230, filed Dec. 9, 2020, which is hereby incorporated by reference in its entirety.

This invention was made with government support under grants CA142746 and CA252364 awarded by the National Institutes of Health, and grant DMR-2011846 awarded by the National Science Foundation. The government has certain rights in the invention.

FIELD OF THE INVENTION

The present invention relates to branched peptides capable of forming micelles when introduced to aqueous medium, enzymatically induced self-assembly of the cleaved peptide products, pharmaceutical compositions containing the branched peptides, and their use to deliver cargo to the mitochondria of cells.

BACKGROUND OF THE INVENTION

As a subcellular organelle, mitochondria play essential roles in many cellular processes, such as apoptosis and metabolism (Green et al., *Science* 305(5684):626-629 (2004); McBride et al., *Curr. Biol.* 16(14):R551-R560 (2006); Kujoth et al., *Science* 309(5733):481-484 (2005); Balaban et al., *Cell* 120(4):483-495 (2005)). Intensive research efforts have focused on developing therapeutics that target mitochondria (Hoye et al., *Acc. Chem. Res.* 41(1):87-97 (2008); Murphy et al., *Annual Review of Pharmacology and Toxicology* 47:629-656 (2007); Yousif et al., *Chembiochem* 10(12):1939-1950 (2009)). In fact, some of the therapeutics have already entered clinical trials (Thomas et al., *J. Am. Soc. Nephrol.* 18(1):213-222 (2007); Birk et al., *J. Am. Soc. Nephrol.* 24(8):1250-1261 (2013); Trachootham et al., *Nat. Rev. Drug. Discov.* 8(7):579-591 (2009)). With the exception of gramicidin S derivatives developed by Wipf et al. (Hoye et al., *Acc. Chem. Res.* 41(1):87-97 (2008)), most of the molecules reported for targeting mitochondria are lipophilic and cationic (Yousif et al., *Chembiochem* 10(12):2081-2088 (2009); Mahon et al., *Chem. & Bio.* 14(8):923-930 (2007); Zhao et al., *Biochem. Pharmacol.* 70(12):1796-1806 (2005); Smith et al., *Eur. J. Biochem.* 263(3):709-716 (1999); Murphy et al., *Annu. Rev. Pharmacol. Toxicol.* 47:629-656 (2007); Murphy, M. P., *Trends Biotechnol.* 15(8):326-330 (1997); Hurt et al., *EMBO J.* 4(13A):3509-3518 (1985); Horton et al., *Chem. Biol.* 15(4):375-382 (2008); Hoye et al., *Acc. Chem. Res.* 41(1):87-97 (2008)). Although those lipophilic cations are able to prevent mitochondrial damage in vitro, they have a major drawback due the toxicity that results from the accumulation in the mitochondrial matrix (Murphy, M. P., *Trends Biotechnol.* 15(8):326-330 (1997)). Thus, it is both desirable and necessary to develop new molecules and processes for targeting mitochondria.

The present invention is directed to overcoming these and other deficiencies in the art.

SUMMARY OF THE INVENTION

A first aspect of the invention relates to a branched peptide that includes a first peptide chain and a second peptide chain having its C-terminal amino acid covalently linked to a sidechain of an amino acid residue of the first peptide chain. The first peptide chain includes a plurality of aromatic amino acids and, optionally, an aromatic group linked to an amino terminus of the first peptide chain. The second peptide chain comprises a plurality of hydrophilic amino acids and an enzyme cleavage site.

A second aspect of the invention relates to a pharmaceutical composition comprising the branched peptide according to the first aspect of the invention in an aqueous medium. The pharmaceutical composition may include one or more therapeutic agents in combination with the branched peptides. In accordance with this aspect of the invention, the branched peptides form micelle structures in the aqueous medium.

A third aspect of the invention relates to a method of delivering a therapeutic agent into mitochondria comprising encapsulating a therapeutic agent within a micelle structure of the pharmaceutical composition according to the second aspect of the invention. A cell is contacted with the pharmaceutical composition, whereby micelle structures are taken up by the cell and targeted to mitochondria within the cell. As a consequence of the micelle structures being targeted to the mitochondria, the therapeutic agent is thereby delivered to the mitochondria.

A fourth aspect of the invention relates to a nanofiber formed in an aqueous medium comprising a self-assembled, enzymatically modified form of the branched peptide of the first aspect of the invention.

A fifth aspect of the invention relates to a supramolecular hydrogel formed in an aqueous medium and comprising a self-assembled, enzymatically modified form of the branched peptide of the first aspect of the invention.

A sixth aspect of the invention relates to a method of treating a patient having a cancerous condition comprising: administering a pharmaceutical composition according the second aspect of the invention to a patient having a cancerous condition, where the administering is effective to inhibit cancer cell survival. In this aspect of the invention, the pharmaceutical composition also includes a therapeutic agent effective for treating cancer cells, i.e., inhibiting cancer cell survival.

A seventh aspect of the invention relates to a method of treating an individual exposed to radiation comprising: administering a pharmaceutical composition according to the second aspect of the invention to an individual exposed to, or about to be exposed to radiation, where the administering is effective to inhibit radiation-induced damage to cells of the individual. In this aspect of the invention, the pharmaceutical composition also includes a therapeutic (or prophylactic) agent effective to inhibit radiation-induced damage to cells.

An eighth aspect of the invention relates to a method of treating a patient for a cardiovascular disease or condition, the method comprising: administering a pharmaceutical composition according to the second aspect of the invention, to an individual having a cardiovascular disease or condition, where the administering is effective to inhibit radiation-induced damage to cells of the individual. In this aspect of the invention, the pharmaceutical composition also includes a therapeutic agent effective for treating a cardiovascular disease or condition.

A ninth aspect of the invention relates to a pharmaceutical composition comprising an aqueous medium, a nucleic acid construct or recombinant viral vector, and a branched peptide comprising a first peptide chain and a second peptide chain having its C-terminal amino acid covalently linked to a sidechain of an amino acid residue of the first peptide chain, wherein the first peptide chain comprises a plurality of aromatic amino acids and, optionally, an aromatic group linked to an amino terminus of the first peptide chain, and wherein the second peptide chain comprises a plurality of hydrophilic amino acids and an enzyme cleavage site; wherein the branched peptide is associated with the nucleic acid construct or recombinant viral vector in the aqueous medium.

The tenth aspect of the invention relates to a method of delivering a nucleic acid molecule into mitochondria comprising: providing a pharmaceutical composition according to the ninth aspect of the invention; and contacting a cell with the pharmaceutical composition, whereby the branched peptide associated with the nucleic acid construct or recombinant viral vector are taken up by the contacted cell and upon cleavage of the cleavage site promotes peri-mitochondrial self-assembly of the first peptides to form a nanofiber matrix comprising the nucleic acid construct or recombinant viral vector, which nucleic acid construct or recombinant viral vector is then delivered into the mitochondria.

An eleventh aspect of the invention relates to a method of treating a patient having a cancerous condition comprising administering a pharmaceutical composition according to the ninth aspect of the invention to a patient having a cancerous condition, wherein the nucleic acid construct or recombinant viral vector disrupts mitochondrial function and promotes cellular apoptosis selectively in cancer cells.

In any of the preceding aspects, the peptide can be conjugated to a therapeutic agent, or a therapeutic agent in non-conjugated form can be present in the products, hydrogels, or pharmaceutical compositions of the invention, such that the therapeutic agent is captured or retained in any hydrogel product formed thereby.

The accompanying Examples demonstrate the enzymatic cleavage of branched peptides that carry negative charges for targeting mitochondria. Conjugating a well-established protein tag, i.e., FLAG-tag (Hopp et al., *Nat. Biotechnol.* 6(10):1204-1210 (1988), which is hereby incorporated by reference in its entirety) to self-assembling motifs (Reches & Gazit, *Science* 300(5619):625-627 (2003); Burattini et al., *J. Am. Chem. Soc.* 132(34):12051-12058 (2010); Zhang et al., *Langmuir* 27(2):529-537 (2010), which are hereby incorporated by reference in their entirety) affords the precursors that are the substrates of enterokinase (ENTK) (Pavlov & Thompson, *The Work of the Digestive Glands*, London: Charles Griffin & Company, Limited (1902), which is hereby incorporated by reference in its entirety). The precursors form micelles, which upon enzymatic cleavage of the hydrophilic branch that contains the FLAG motif (DDDDK) (Hopp et al., *Nat. Biotechnol.* 6(10):1204-1210 (1988), which is hereby incorporated by reference in its entirety) turn into nanofibers. Fluorescent microscopy of live cells reveals that, after being taken up by cells, the branched peptides and their enzyme cleaved products mainly localize to the mitochondria. Moreover, the micelles of the precursors are able to deliver cargo, including small molecules (as exemplified by doxorubicin (Dox)), viral vectors (as exemplified by baculovirus), and proteins (as exemplified by red phycoerythrin (RPE)(Teale & Dale, *Biochem. J.* 116(2):161-169 (1970), which is hereby incorporated by reference in its entirety) into cells, largely to mitochondria and within about two hours. Western blot indicates ENTK on the isolated mitochondria of cancer cells, and transmission electron microscopy (TEM) of the isolated mitochondria confirms the conversion of the micelles to nanofibers at the mitochondria. Preventing ENTK proteolysis diminishes the mitochondria targeting. These results confirm enzyme-induced self-assembly as the process for targeting mitochondria. As the first report of using perimitochondrial enzymatic noncovalent synthesis ("ENS") for targeting mitochondria and delivery of molecular cargo to mitochondria (see FIG. 1), this application and its accompanying Examples illustrate a fundamentally new molecular motif and process for targeting mitochondria and exploring the applications of protease-instructed assembly for biomedicine.

The accompanying Examples also demonstrate that, using this same branched peptide ("Mito-Flag" or D-2⊤FLAG), perimitochondrial ENS enables selective genetic engineering of the mitochondria of cancer cells. The branched Mito-Flag peptide self-assembles into micelles carrying the genetic payload. After the micelles enter cancer cells mainly via clathrin mediated endocytosis, the mitochondria-bound ENTK hydrolyzes the Flag-tag, allowing the cleaved peptide to self-assemble and form nanofibers (collectively forming a hydrogel) on mitochondria. Using mitochondria-specific codons (Jukes et al., "Evolutionary Changes in the Genetic Code," *Comp. Biochem. Physiol. B* 106:489-494 (1993), which is hereby incorporated by reference in its entirety) further confirms the gene expression in mitochondria. This perimitochondrial ENS approach transfects gene vectors encoding CRISPR/Cas9 (Glass et al., "Engineering the Delivery System for CRISPR-based Genome Editing," *Trends Biotech.* 36:173-185 (2018); Glass et al., "Nanoparticles for CRISPR-Cas9 Delivery," *Nat Biomed. Eng.* 1:854-855 (2017), each of which is hereby incorporated by reference in its entirety) into the mitochondria of cancer cells to knockout MT-CO1 gene, which depletes oxidative phosphorylation (OXPHOS) and re-sensitize the cancer cells to cisplatin. Additionally, Mito-Flag facilitates the gene expression of FUNDC1 and GFP-tagged p53 proteins in the mitochondria of cancer cells, which induces mitophagy (Liu et al., "Mitochondrial Outer-Membrane Protein FUNDC1 Mediates Hypoxia-Induced Mitophagy In Mammalian Cells," *Nat. Cell Biol.* 14:177-185 (2012), which is hereby incorporated by reference in its entirety) and apoptosis (Green et al., "The Pathophysiology of Mitochondrial Cell Death," *Science* 305:626-629 (2004), which is hereby incorporated by reference in its entirety), respectively. Besides DNA plasmid, combining viral gene vectors and Mito-Flag results in the exclusive expression of non-mitochondrial proteins (e.g., GFP, RFP-LAMP1, or GFP-PTS) in cancer cell mitochondria. Using Rifampicin (Gadaleta et al., "The Effect of Rifampicin on Mitochondrial RNA Polymerase From Rat Liver," *FEBS Lett.* 10:54-56 (1970), which is hereby incorporated by reference in its entirety), an inhibitor specific for mitochondrial RNA polymerase, confirms that the delivered genes undergo transcription in mitochondria. Mechanistically, the electrostatic interaction between Mito-Flag and voltage-dependent anion channel (VDAC) on mitochondrial surface favors the mitochondria-specific attachment of Mito-Flag. For the cells having a low level or knockdown of mitochondria bound ENTK, perimitochondrial ENS is absent, therefore the production of those proteins hardly occurs in the mitochondria. Furthermore, mitochondrial membrane potential and pH gradient are necessary for perimitochondrial ENS to target mitochondrial of the cancer cells. This work, illustrating perimitochondrial ENS for assisting genetic engineering of cancer mitochondria, offers a versatile and robust strategy for selectively targeting mitochondria of cancer cells and for the understanding correlation of mitochondria and cancer (Wallace, "Mitochondria and Cancer," *Nat. Rev. Cancer* 12:685-698 (2012), which is hereby incorporated by reference in its entirety).

BRIEF DESCRIPTION OF THE DRAWINGS

FIG. 5A are TEM images of D-1 ᴛ FLAG before (left) and after (right) adding ENTK (24 h), scale bar=100 nm. FIG. 5B are fluorescent images of HeLa and U87MG cells incubated with D-1 ᴛ FLAG for 2 h. FIG. 5C are fluorescence images of D-1 ᴛ FLAG and MitoTracker in HeLa cells. FIG. 5D are HeLa cells treated by the mixture of RPE (1 μg/mL) and D-1 ᴛ FLAG for 2 h. Scale bar=30 μm in (B, C). The concentration of D-1 ᴛ FLAG is 200 μM for A-D.

FIG. 6 is a pair of TEM image of RPE and the mixture of RPE and D-1 ᴛ FLAG. The clear background in the TEM image of the mixture indicates the encapsulation of RPE by D-1 ᴛ FLAG. Scale bar=100 nm.

FIGS. 7A-D display the difference between D-2 ᴛ FLAG and L-2 ᴛ FLAG. In FIGS. 7A-B, HeLa cells incubated separately with RPE (1 μg/mL) and Dox (2 μM) while mixing with D-2 ᴛ FLAG and L-2 ᴛ FLAG (200 μM) for 2 h. In FIG. 7C, GFP-cyt c HeLa cells were treated by the mixture of RPE (1 μg/ml) and D-2 ᴛ FLAG (200 μM) for 2 h. Scale bar=30 μm. FIG. 7D is a graph showing the co-localization analysis of GFP-cyt c and Omi-mcherry expressing HeLa cells treated by RPE or Dox in the presence of D-2 ᴛ FLAG. R=1 indicates perfect co-localization.

FIGS. 8A-E display the cytotoxicity data of D-2 ᴛ FLAG. FIGS. 8A-B are graphical representations of the cytotoxicity data of L-2 ᴛ FLAG and D-2 ᴛ FLAG against HeLa and U87MG cells, respectively. FIGS. 8C-D show the combination of Dox (2 μM) and L-2 ᴛ FLAG and D-2 ᴛ FLAG exhibit increased cancer cell inhibition. FIG. 8E shows the synergistic effect on the inhibition of cancer cells are gained by Compusyn (Chou, *Pharmacol. Rev.* 58(3):621(2006), which is hereby incorporated by reference in its entirety). CI<1 means synergistic effect, >1 means antagonistic effect, =1 means additive effect.

FIGS. 9A-B are TEM images of mitochondria isolated from HeLa cells being incubated with D-2 ᴛ FLAG (200 μM) for 2 h (FIG. 9A) and 24 h (FIG. 9B). Scale bar equals 100 nm.

FIG. 10 show the western blot analysis of ENTK in the mitochondria lisolated from HeLa and U87MG cells. The present of ENTK light chain may due to the fact that the disulfide bond linking the light chain and heavy chain of ENTK was broken (reduced) by 2-mercaptoethanol (Anfinsen et al., *J. Biol. Chem.* 236(5):1361(1961), which is hereby incorporated by reference in its entirety) included in the loading buffer for western blot experiments.

FIG. 11 are images of the Sol/micelles-gel/fibers transition of Mito-Flag (also referred to as D-2 ᴛ FLAG) by ENTK in solution. The concentration of Mito-Flag for producing hydrogel is 2.5 wt %. For TEM images, the concentration of Mito-Flag is 200 μM. ENTK concentration is 10 U/ml for all samples. The incubation time is 24 h.

FIGS. 21A-B are illustrations of perimitochondrial ENS. FIG. 21A is the molecular structure of Mito-Flag and the illustration of the ENS catalyzed by ENTK. FIG. 21B is an illustration of the proteolysis (ENTK cleaving off the Flag-tag) of Mito-Flag to result in supramolecular assemblies of Nap-ffk(G)y and the consequential phase/morphology transition on mitochondria to facilitate the mitochondrial genetic engineering.

FIGS. 22A-F show how perimitochondrial ENS delivers oligonucleotides, nucleic acids, and plasmids into mitochondria. FIG. 22A is a panel of fluorescent images showing how HeLa cells, incubated with Mito-Flag and FITC-labeled oligonucleotides (100 nM, 24 h), display green fluorescence of FITC in mitochondria. FIG. 22B is a panel of fluorescent images of mtDNA depleted HeLa cells incubated with 1 mL pMAX-DEST plasmid (10 μg/mL, 24 h) mixed with/without Mito-Flag. FIG. 22C is a gel electrophoresis analysis of pGLO plasmid in the pellet of Mito-Flag after high-speed centrifuge. FIG. 22D is a panel of fluorescent images of the HeLa cells incubated with pGLO and Mito-pGLO plasmid (5 µg/mL, 24 h, 0.2 wt % arabinose) in the presence of Mito-Flag. FIG. 22E shows is an image of a gel showing detection of pGLO plasmid in the mitochondria isolated from the HeLa cells treated by pGLO (5 µg/mL) and Mito-Flag via PCR and DNA electrophoresis. FIG. 22F is a pair of fluorescent images of the HeLa cells expressing pGLO (in mitochondria) before and after one passage. All Mito-Flag concentrations are 200 µM.

FIGS. 23A-G show how perimitochondrial ENS delivers CRISPR/Cas9 components into the mitochondria of cancer cells for mitochondrial genome editing. FIG. 23A is a panel of fluorescence images of HeLa cells incubated with plasmid encoding CRISPR-Cas9-mCherry and siRNA for enterokinase (ENTK) knockdown. The red fluorescence from mCherry in mitochondria indicates the gene delivery and expression in mitochondria. FIG. 23B is a Western blot analysis of MT-CO1 for HeLa cells treated by solvent control (PBS), free CRISPR-MT-CO1 plasmid, Mito-Flag and the mixture of Mito-Flag and CRISPR-MT-CO1 plasmid. The reduced level of MT-CO1 protein in the combination treatment indicates the knockout of the native MT-CO1 gene. FIG. 23C is a PCR analysis of MT-CO1 gene for HeLa cells treated by solvent control (PBS), free CRISPR-MT-CO1 plasmid, Mito-Flag and the mixture of Mito-Flag and CRISPR-MT-CO1 plasmid. The band of MT-CO1 gene in the combination group is hardly observed. FIG. 23D is an nATP (red) visualization in HeLa cells incubated with solvent control (PBS), free CRISPR-MT-CO1 plasmid, Mito-Flag, and the mixture of Mito-Flag and CRISPR-MT-CO1 plasmid. The cells in the combination group exhibit little fluorescence from ATP-Red in mitochondria, indicating the dysfunction of OXPHOS (MT-CO1 is the catalytic site of cytochrome c oxidase). FIGS. 23E-G graphically show how the knockout of MT-CO1 leads to reduced efficiency in MDR (FIG. 23E), sensitizes cancer cell to cisplatin (FIG. 23F), and reduces mitochondrial membrane potential (FIG. 23G). Data are presented as mean±standard deviation.

FIGS. 24A-G show how perimitochondrial ENS causes mitochondrial transgene expression to induce mitophagy or apoptosis. FIG. 24A is a Western blot analysis of FUNDC1 and LC3B levels in the mitochondria fraction and cytosolic fraction, respectively, of HeLa cells incubated with conditions of interest. VDAC1 serves as mitochondria protein loading control. FUNDC1 plasmid: 5 µg/mL, Mito-Flag: 200 µM, Time: 2 days. FIG. 24B is a panel of fluorescent images showing that Mito-Flag perimitochondrial ENS delivering FUNDC1 gene into mitochondria to induce mitochondrial morphology changes within 2 days. FIG. 24C is a panel of fluorescent images showing that the detection of mitophagy via immunofluorescent staining of autophagy marker, LC3 ($2^{nd}$ day). FIG. 24D is a panel of fluorescent images of HeLa cells incubated with free GFP-TP53 plasmid and the plasmid mixed with Mito-Flag (200 µM, 24 h). FIG. 24E is a graph illustrating cell viability of HeLa, Saos-2, and HS-5 cells incubated with free GFP-TP53 plasmid (5 µg/mL), Mito-Flag (200 µM), and the plasmid (5 µg/mL) mixed with Mito-Flag (200 µM, $3^{rd}$ day). Data are presented as mean±standard deviation. FIG. 24F is a panel of fluorescent images showing an apoptosis analysis on HeLa and HS-5 cells. FIG. 24G is a pair of fluorescent images showing cells incubated with GFP-TP53 plasmid (5 µg/mL) mixed by Mito-Flag (200 µM, $3^{rd}$ day) via propidium iodide staining.

FIG. 25A-K shows how perimitochondrial ENS combines with viral gene vectors for mitochondrial transgene expression. FIG. 25A is a TEM image of free baculovirus. FIG. 25B is a pair of TEM images of the mixture of baculovirus and Mito-Flag micelles (arrow pointed) before/after adding ENTK. FIG. 25C is a panel of fluorescent images of HeLa cells incubated with baculoviral RFP-LAMP1 for 24 h. FIG. 25D is a panel of fluorescence from RFP-LAMP1 in HeLa cells treated by the mixture of baculovirus and Mito-Flag localizes in mitochondria. Mitochondria are stained by MitoTracker. FIG. 25E is a Western blot of RFP-LAMP1 protein in mitochondria isolated from the HeLa cells treated by baculoviral RFP-LAMP1 with or without Mito-Flag for 24 h. FIG. 25F is a panel of fluorescent images of virus-transfected (RFP-LAMP1) HeLa cells before and after cell passage. FIG. 25G graphically illustrates the processes 1 and 2, and shows a pair of representative fluorescent images illustrating localizations of RFP-LAMP1 in the mitochondria of the HeLa cells. Red=RFP, Green=MitoTracker. FIG. 25H is a panel of fluorescent images showing how Rifampycin inhibits the protein expression of RFP-LAMP1 in mitochondria. Red=RFP, Green=MitoTracker. FIGS. 25I-K are panels of fluorescent images showing Saos-2, HepG2, and HS-5 cells, respectively, which are incubated with baculoviral RFP-LAMP1 mixed with Mito-Flag. All Mito-Flag concentrations are 200 µM.

FIG. 26A-I provide evidence of the mechanism of action for Mito-Flag. FIG. 26A shows the cellular uptake of NBD-Mito-Flag (200 µM for 2 h, a fluorescent analog of Mito-Flag) without and with CPZ (5 µM, clathrin-dependent endocytosis inhibitor). FIG. 26B is a panel of confocal fluorescence images of HeLa cells incubated with NBD-Mito-Flag (200 µM) and chloroquine (10 µM). FIG. 26C is a Western blot analysis of ENTK in mitochondria isolated from HeLa and HS-5 cells, which confirms higher ENTK expression in HeLa than in HS-5 cells. FIG. 26D is a panel of TEM images of mitochondria isolated from HeLa, HEK293 and HS-5 cells incubated with 200 µM Mito-Flag for 24 h. Results indicate that ENS-induced phase transition on mitochondria is critical for mitochondria-specific gene transfection. FIG. 26E and FIG. 26F are fluorescent images of NBD-Mito-Flag and RFP-LAMP1 in ENTK-knockdown HeLa cells. The reduced mitochondrial fluorescence and colocalization (indicated by arrows) indicate that ENTK is essential for the mitochondrial accumulation of Flag-tagged peptides. FIG. 26G-H are fluorescent images of the HeLa cells incubated with NBD-Mito-Flag (200 µM, 2 h) (FIG. 26G) or the mixture of virus (RFP-LAMP1) and Mito-Flag (200 µM, 24 h) (FIG. 26H) in the presence of erastin of different concentrations. The non-mitochondria fluorescence (lysosome) in FIG. 26H is indicated by white arrow. FIG. 26I is a panel of fluorescent images of HeLa cells incubated with NBD-Mito-Flag (200 µM, 2 h) after the pretreatment by Ndz (10 µM, 1 h).

FIG. 27 provides partial sequence of pGLO (SEQ ID NOS: 83 and 84) and Mito-pGLO (SEQ ID NOS: 85 and 86). Mutated codons are boxed.

DETAILED DESCRIPTION OF THE INVENTION

Figure 1:
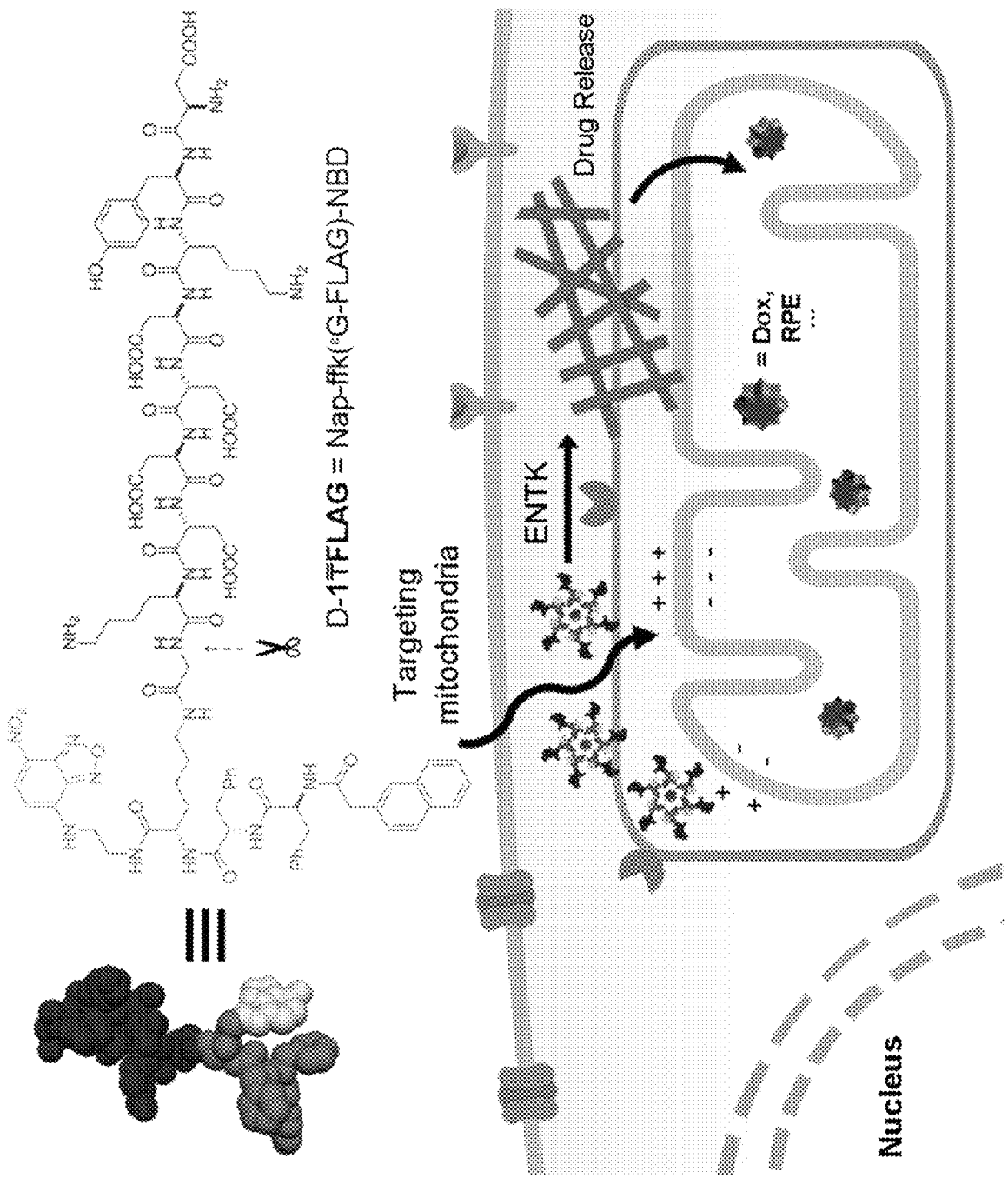
FIG. 1 is a schematic illustration of the structure of a representative branched peptide, its cellular uptake and ENTK-induced cleavage of the branched peptide to convert micelles into nanofibers assembled on mitochondria (i.e., perimitochondrial ENS).

One aspect of the invention relates to a branched peptide that includes a first peptide chain and a second peptide chain having its C-terminal amino acid covalently linked to a sidechain of an amino acid residue of the first peptide chain. The first peptide chain includes a plurality of aromatic amino acids and, optionally, an aromatic group linked to an amino terminus of the first peptide chain. The second peptide chain comprises a plurality of hydrophilic amino acids and an enzyme cleavage site. As discussed more fully below, the branched peptides are capable of forming micelle structures in an aqueous medium and, following enzymatic cleavage of the second peptide chain at the enzyme cleavage site, the resulting (branched) peptide is capable of self-assembling to form nanofibers and, eventually, a hydrogel in an aqueous medium.

The term "amino acid" further includes analogues, derivatives, and congeners of any specific amino acid referred to herein, as well as C-terminal or N-terminal protected amino acid derivatives (e.g., modified with an N-terminal or C-terminal protecting group). Furthermore, the term "amino acid" includes both D- and L-amino acids. Hence, an amino acid which is identified herein by its name, three letter or one letter symbol and is not identified specifically as having the D or L configuration, is understood to assume any one of the D or L configurations. For example, 2-Nal or 2-Nal$_D$ refer to the L and D configurations, respectively, of the analogue 3-(2-naphthyl)-alanine.

Naturally occurring amino acids are identified throughout by the conventional three-letter and/or one-letter abbreviations, corresponding to the trivial name of the amino acid, in accordance with the following list: Alanine (Ala), Arginine (Arg), Asparagine (Asn), Aspartic acid (Asp), Cysteine (Cys), Glutamic acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), and Valine (Val). The abbreviations are accepted in the peptide art and are recommended by the IUPAC-IUB commission in biochemical nomenclature As used herein the term "peptide" includes native peptides (either degradation products or synthetically synthesized peptides) and further to peptidomimetics, such as peptoids and semipeptoids which are peptide analogs, which may have, for example, modifications rendering the peptides more stable while in a body, having lower immunogenicity and/or higher affinity to their receptors.

As used herein, the term "about" when used in connection with a numerical value denotes an interval of accuracy that is ±10% in certain embodiments, ±5% in other embodiments, ±2.5% in still further embodiments, and ±1% in yet another embodiment.

As used herein and in the appended claims, the singular "a", "an" and "the" include the plural reference unless the context clearly dictates otherwise. Thus, for example, reference to a "peptide" includes a plurality of such peptides.

In some embodiments of the invention, the branched peptide, following enzymatic cleavage of the second peptide chain at the enzyme cleavage site, is capable of self-assembling to form nanofibers containing the cleavage product and a hydrogel composed of such nanofibers, when present in an aqueous medium. A hydrogel may be defined as a three-dimensional, hydrophilic or amphiphilic polymeric network capable of taking up a quantity of water, typically a large quantity of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water that allows them to swell in aqueous media. The chains of the network are connected in such a fashion that pores exist and that a substantial fraction of these pores are of dimensions between 1 nm and 1000 nm.

As used herein and is well-known in the art, the term "hydrogel" refers to a material that comprises fibrous networks formed of water-soluble natural or synthetic polymer chains, typically (though not exclusively) containing more than 95% water, often more than 96%, 97%, 98%, or 99% water.

The term "gelling" or "gelation" means a thickening of the medium that may result in a gelatinous consistency and even in a solid, rigid consistency that does not flow under its own weight.

A "gelator" is defined herein to include a non-polymeric organic compound whose molecules can establish, between themselves, at least one physical interaction leading to a self-assembly of the molecules in a carrier fluid to form a gel. The gel may result from the formation of a network of molecular nanofibers due to the stacking or aggregation of gelator molecules. The gelator is the product of enzymatic cleavage of the branched peptide.

The first peptide chain can have any length that is sufficient to allow for self-assembly after enzymatic cleavage (of the second peptide chain of the branched peptide). This includes peptides up to about 70 amino acids, up to about 65 amino acids, up to about 60 amino acids, up to about 55 amino acids, up to about 50 amino acids, up to about 45 amino acids, up to about 40 amino acids, up to about 35 amino acids, up to about 30 amino acids, up to about 25 amino acids, up to about 20 amino acids, up to about 15 amino acids, or up to about 10 amino acids. In certain embodiments, the first peptide chain is less than 20 amino acids in length.

In certain embodiments of the invention, the first peptide chain contains only D-amino acids. In an alternative embodiment, the first peptide chain contains only L-amino acids, or a mixture of L- and D-amino acids.

To promote self-assembly, the first peptide chain preferably includes aromatic amino acids, including one or more of phenylalanine, tyrosine, and tryptophan, or any derivatives thereof.

In the first peptide chain, the amino acid residue to which the second peptide chain is covalently linked is one that has (or had, prior to such covalent linkage) a reactive sidechain. This amino acid having the reactive sidechain can be (i) one having a basic sidechain with a reactive amino group, such as Arg or Lys; or (ii) one having a nucleophilic sidechain with a reactive hydroxyl group or thiol group, such as Ser or Thr or Cys, but preferably Ser or Cys; or (iii) one having a basic sidechain with a reactive imidazole group, such as His. The amino acids having a reactive amino group will form a —NH—C(O)— covalent bond with the second peptide C-terminus as described in the accompanying Examples. The amino acids having a reactive hydroxyl group will form a —O—C(O)— covalent bond with the second peptide C-terminus (see Ono et al., *Bull. Chem. Soc. Japan* 51(8): 2401-2404 (1978), which is hereby incorporated by reference in its entirety). The amino acids having a reactive thiol group will form a —S—C(O)— covalent bond with the second peptide C-terminus (see Ingenito et al., *JACS* 121: 11369-74 (1999), which is hereby incorporated by reference in its entirety).

In one embodiment, the first peptide chain includes an aromatic group linked to the amino terminus of the first peptide chain. The aromatic group can be any suitable single- or multi-ring aromatic moiety that facilitates self-assembly as discussed herein. Exemplary aromatic groups include, without limitation, phenylacetyl, naphthylacetyl, fluorenylacetyl, pyrenylacetyl, and cinnamoyl.

Exemplary first peptide chains of the present invention include, without limitation: napthylacetyl-FFKY (SEQ ID NO: 1), napthylacetyl-FFFKY (SEQ ID NO: 2), napthylacetyl-FFGKY (SEQ ID NO: 3), napthylacetyl-FFGK (SEQ ID NO: 4), napthylacetyl-FFGKF (SEQ ID NO: 5), napthylacetyl-ffky, napthylacetyl-fffky, napthylacetyl-ffgky, napthylacetyl-ffgk, napthylacetyl-ffgkf, napthylacetyl-FFK (Dmt) (SEQ ID NO: 6), napthylacetyl-FFFK(Dmt) (SEQ ID NO: 7), napthylacetyl-FFGK(Dmt) (SEQ ID NO: 8), napthylacetyl-ffk(dmt), napthylacetyl-fffk(dmt), napthylacetyl-ffgk(dmt), napthylacetyl-FFCY (SEQ ID NO: 9), napthylacetyl-FFFCY (SEQ ID NO: 10), napthylacetyl-FFGCY (SEQ ID NO: 11), napthylacetyl-FFGC (SEQ ID NO: 12), napthylacetyl-FFGCF (SEQ ID NO: 13), napthylacetyl-ffcy, napthylacetyl-fffcy, napthylacetyl-ffgcy, napthylacetyl-ffgc, napthylacetyl-ffgcf, napthylacetyl-FFC (Dmt) (SEQ ID NO: 14), napthylacetyl-FFFC(Dmt) (SEQ ID NO: 15), napthylacetyl-FFGC(Dmt) (SEQ ID NO: 16), napthylacetyl-ffc(dmt), napthylacetyl-fffc(dmt), napthylacetyl-ffgc(dmt), where Dmt is 2,6-dimethyl-L-tyrosine and dmt is 2,6-dimethyl-D-tyrosine, and where the second peptide chain is linked to the sidechain of the lysine or cysteine residue.

In certain embodiments, the first peptide chain further includes a therapeutic agent, Z, covalently bonded to the C-terminal residue of first peptide chain. Covalent attachment may be carried out directly to the C-terminus or following amidation of the C-terminus. By way of example only, one such first peptide is napthylacetyl-FFKY-Z (SEQ ID NO: 1), where the tyrosine moiety is covalently linked to the therapeutic agent. The therapeutic agent, Z, can be any type of therapeutic agent that is capable of being so-modified. Exemplary therapeutic agents include, without limitation, antioxidants, coenzymes, vitamins, metabolites, analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-thrombogenic agents, anti-claudication agents, anti-atherosclerotic drugs, vascular agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastrointestinal agents, histamine receptor antagonists, keratolyptics, lipid regulating agents, anti-anginal agents, Cox-2 inhibitors, leukotriene inhibitors, macrolides, muscle relaxants, nutritional agents, opioid analgesics, protease inhibitors, sex hormones, stimulants, anti-osteoporosis agents, anti-obesity agents, cognition enhancers, anti-urinary incontinence agents, anti-benign prostate hypertrophy agents, essential fatty acids, non-essential fatty acids, cytokines, growth factors, antibodies, radioprotective agents, and cardioprotective agents.

In certain embodiments of the invention, the second peptide chain comprises not more than 50 amino acid residues between the enzyme cleavage site and the covalent bond formed between the first and second peptide chains. In a further embodiment, the second peptide chain comprises a single amino acid residue between the cleavage site and the covalent bond between the peptide chains, where the single amino acid is other than Trp or Pro.

The second peptide chain preferably comprises L-amino acids, which improves its susceptibility to enzymatic cleavage.

As noted above, the second peptide chain includes an enzyme cleavage site. While various enzyme cleavage sites are contemplated, preferred enzyme cleavage sites are those that are acted upon by endoenzymes that have specificity for a particular amino acid sequence. One preferred class of enzymes cleavage sites are enterokinase cleavage sites.

Exemplary amino acid sequences of the second peptide chain of the present invention include, without limitation: DDDDK (SEQ ID NO: 17), KDDDK (SEQ ID NO: 18), DDDDR (SEQ ID NO: 19), KDDDR (SEQ ID NO: 20), DADDK (SEQ ID NO: 21), KADDK (SEQ ID NO: 22), DADDR (SEQ ID NO: 23), KADDR (SEQ ID NO: 24), DEDDK (SEQ ID NO: 25), KEDDK (SEQ ID NO: 26), DEDDR (SEQ ID NO: 27), KEDDR (SEQ ID NO: 28), EDDDK (SEQ ID NO: 29), EDDDR (SEQ ID NO: 30), EEDDK (SEQ ID NO: 31), EEDDR (SEQ ID NO: 32), DLYDDDDK (SEQ ID NO: 33), DLYDDDDR (SEQ ID NO: 34), DYKDDDDK (SEQ ID NO: 35), DYKDDDDR (SEQ ID NO: 36), DYKDADDK (SEQ ID NO: 37), DYKDADDR (SEQ ID NO: 38), DYKDEDDK (SEQ ID NO: 39), DYKDEDDR (SEQ ID NO: 40), DYKEDDDK (SEQ ID NO: 41), DYKEDDDR (SEQ ID NO: 42), DYKEEDDK (SEQ ID NO: 43), DYKEEDDR (SEQ ID NO: 44), and LKGDR (SEQ ID NO: 45) (Shahravan et al., *Protein Expr. Purif.* 59(2):314-319 (2008), which is hereby incorporated by reference in its entirety). Variations of the above-identified peptides are also contemplated where additional amino acid residues are introduced between the cleavage site and the C-terminal residue, or where additional N-terminal amino acids are introduced to the second peptide chain.

Additional exemplary amino acid sequences of the second peptide chain of the present invention include, without limitation:

```
                             (SEQ ID NO: 46)
DDDDK(G/A/T/S/Y/H/Q/E/N/D/R/K), (SEQ ID NO: 47)
KDDDK(G/A/T/S/Y/H/Q/E/N/D/R/K), (SEQ ID NO: 48)
DDDDR(G/A/T/S/Y/H/Q/E/N/D/R/K), (SEQ ID NO: 49)
KDDDR(G/A/T/S/Y/H/Q/E/N/D/R/K), (SEQ ID NO: 50)
DADDK(G/A/T/S/Y/H/Q/E/N/D/R/K), (SEQ ID NO: 51)
KADDK(G/A/T/S/Y/H/Q/E/N/D/R/K), (SEQ ID NO: 52)
DADDR(G/A/T/S/Y/H/Q/E/N/D/R/K), (SEQ ID NO: 53)
KADDR(G/A/T/S/Y/H/Q/E/N/D/R/K), (SEQ ID NO: 54)
DEDDK(G/A/T/S/Y/H/Q/E/N/D/R/K), (SEQ ID NO: 55)
KEDDK(G/A/T/S/Y/H/Q/E/N/D/R/K), (SEQ ID NO: 56)
DEDDR(G/A/T/S/Y/H/Q/E/N/D/R/K), (SEQ ID NO: 57)
KEDDR(G/A/T/S/Y/H/Q/E/N/D/R/K), (SEQ ID NO: 58)
EDDDK(G/A/T/S/Y/H/Q/E/N/D/R/K), (SEQ ID NO: 59)
EDDDR(G/A/T/S/Y/H/Q/E/N/D/R/K),
```

```
                                (SEQ ID NO: 60)
EEDDK(G/A/T/S/Y/H/Q/E/N/D/R/K), (SEQ ID NO: 61)
EEDDR(G/A/T/S/Y/H/Q/E/N/D/R/K), (SEQ ID NO: 62)
DLYDDDDK(G/A/T/S/Y/H/Q/E/N/D/R/K), (SEQ ID NO: 63)
DLYDDDDR(G/A/T/S/Y/H/Q/E/N/D/R/K), (SEQ ID NO: 64)
DYKDDDDK(G/A/T/S/Y/H/Q/E/N/D/R/K), (SEQ ID NO: 65)
DYKDDDDR(G/A/T/S/Y/H/Q/E/N/D/R/K), (SEQ ID NO: 66)
DYKDADDK(G/A/T/S/Y/H/Q/E/N/D/R/K), (SEQ ID NO: 67)
DYKDADDR(G/A/T/S/Y/H/Q/E/N/D/R/K), (SEQ ID NO: 68)
DYKDEDDK(G/A/T/S/Y/H/Q/E/N/D/R/K), (SEQ ID NO: 69)
DYKDEDDR(G/A/T/S/Y/H/Q/E/N/D/R/K), (SEQ ID NO: 70)
DYKEDDDK(G/A/T/S/Y/H/Q/E/N/D/R/K), (SEQ ID NO: 71)
DYKEDDDR(G/A/T/S/Y/H/Q/E/N/D/R/K), (SEQ ID NO: 72)
DYKEEDDK(G/A/T/S/Y/H/Q/E/N/D/R/K), (SEQ ID NO: 73)
DYKEEDDR(G/A/T/S/Y/H/Q/E/N/D/R/K),
and (SEQ ID NO: 74)
LKGDR(G/A/T/S/Y/H/Q/E/N/D/R/K).
```

Based on the foregoing, any combination of first and second peptides is contemplated herein, which are formed by reaction of the sidechain —NH$_2$, —OH, or —SH group (e.g., on Lys, Arg, Ser, Thr, or Cys) with the C-terminal carboxyl group, thereby forming a NH—C(O)— bond or —O—C(O)— bond or —S—C(O)— bond, respectively. Exemplary branched peptides of the invention include, without limitation:

```
Nap-FFK($^\varepsilon$G-KDDDDKYD-NH$_2$)Y,

Nap-ffk($^\varepsilon$G-KDDDDKYD-NH$_2$)y,

Nap-FFK($^\varepsilon$G-RDDDDKYD-NH$_2$)Y,

Nap-ffk($^\varepsilon$G-RDDDDKYD-NH$_2$)y,

Nap-FFK($^\varepsilon$G-KDDDDKYD-NH$_2$)(Dmt),

Nap-ffk($^\varepsilon$G-KDDDDKYD-NH$_2$)(dmt),

Nap-FFK($^\varepsilon$G-RDDDDKYD-NH$_2$)(Dmt),

Nap-ffk($^\varepsilon$G-RDDDDKYD-NH$_2$)(dmt),

Nap-FFK($^\varepsilon$G-KDDDDK(Dmt)D-NH$_2$)Y,

Nap-ffk($^\varepsilon$G-KDDDDK(Dmt)D-NH$_2$)y,

Nap-FFK($^\varepsilon$G-RDDDDK(Dmt)D-NH$_2$)Y,

Nap-ffk($^\varepsilon$G-RDDDDK(Dmt)D-NH$_2$)y,

Nap-FFK($^\varepsilon$G-KDDDDK(Dmt)D-NH$_2$)(Dmt),

Nap-ffk($^\varepsilon$G-KDDDDK(Dmt)D-NH$_2$)(dmt),

Nap-FFK($^\varepsilon$G-RDDDDK(Dmt)D-NH$_2$)(Dmt),

Nap-ffk($^\varepsilon$G-RDDDDK(Dmt)D-NH$_2$)(dmt),

Nap-FFK($^\varepsilon$G-KDDDDKYD-NH$_2$)Y-Z,

Nap-ffk($^\varepsilon$G-KDDDDKYD-NH$_2$)y-Z,

Nap-FFK($^\varepsilon$G-RDDDDKYD-NH$_2$)Y-Z,

Nap-ffk($^\varepsilon$G-RDDDDKYD-NH$_2$)y-Z,

Nap-FFK($^\varepsilon$G-KDDDDKYD-NH$_2$)(Dmt)-Z,

Nap-ffk($^\varepsilon$G-KDDDDKYD-NH$_2$)(dmt)-Z,

Nap-FFK($^\varepsilon$G-RDDDDKYD-NH$_2$)(Dmt)-Z,

Nap-ffk($^\varepsilon$G-RDDDDKYD-NH$_2$)(dmt)-Z,

Nap-FFK($^\varepsilon$G-KDDDDK(Dmt)D-NH$_2$)Y-Z,

Nap-ffk($^\varepsilon$G-KDDDDK(Dmt)D-NH$_2$)y-Z,

Nap-FFK($^\varepsilon$G-RDDDDK(Dmt)D-NH$_2$)Y-Z,

Nap-ffk($^\varepsilon$G-RDDDDK(Dmt)D-NH$_2$)y-Z,

Nap-FFK($^\varepsilon$G-KDDDDK(Dmt)D-NH$_2$)(Dmt)-Z,

Nap-ffk($^\varepsilon$G-KDDDDK(Dmt)D-NH$_2$)(dmt)-Z,

Nap-FFK($^\varepsilon$G-RDDDDK(Dmt)D-NH$_2$)(Dmt)-Z,

Nap-ffk($^\varepsilon$G-RDDDDK(Dmt)D-NH$_2$)(dmt)-Z,
``` where Z is a therapeutic agent covalently bonded to the C-terminal residue of the first peptide chain, and where Dmt is 2,6-dimethyl-L-tyrosine and dmt is 2,6-dimethyl-D-tyrosine. To the extent that specific embodiments are not otherwise listed above, it is explicitly contemplated that each of the peptides listed above as containing L-amino acids can also be prepared in the form of its D-amino acid enantiomer. For each peptide listed above as containing a mixture of L- and D-amino acids, it is also explicitly contemplated that each of those peptides can be prepared in the form containing only L-amino acids or only D-amino acids.

The branched peptide of the present invention can be prepared by synthesizing protected first and second peptide chains, which are then reacted together using suitable solid-phase or liquid phase peptide coupling conditions, whereby the C-terminus of the second peptide chain (bearing —COOH group) is reacted with the exposed sidechain of the first peptide chain (bearing reactive —NH$_2$ group, —OH group, or —SH group) to form the branched peptide. Thereafter, the branched peptide can be de-protected and purified using standard procedures.

Combinations of two or more branched peptides are contemplated herein, including where one branched peptide is un-derivatized with a therapeutic agent and one or more additional branched peptides that are derivatized with the same or different therapeutic agents; or where two or more branched peptides are un-derivatized with a therapeutic agent; or where each of two or more branched peptides are derivatized with the same or different therapeutic agents, and no branched peptide that is un-derivatized with a therapeutic agent is present.

Another aspect of the invention relates to a pharmaceutical composition that includes the branched peptide, as described herein, in an aqueous medium.

In certain embodiments the branched peptides in the pharmaceutical composition form micelle structures. Additionally, the pharmaceutical composition can further contain a therapeutic agent encapsulated within the micelle structures. These therapeutic agents can be hydrophobic.

Exemplary therapeutic agents include, but are not limited to, the following: analgesics, anti-inflammatory agents, anti-helminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-thrombogenic agents, anti-claudication agents, anti-atherosclerotic drugs, vascular agents, anti-malarials, anti-migraine agents, anti-muscarinic agents, anti-neoplastic agents (e.g., antiproliferative or chemotherapeutic agents), erectile dysfunction improvement agents, immunosuppressants, anti-protozoal agents, antithyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opioid analgesics, protease inhibitors, sex hormones, stimulants, anti-osteoporosis agents, anti-obesity agents, cognition enhancers, anti-urinary incontinence agents, anti-benign prostate hypertrophy agents, essential fatty acids, non-essential fatty acids, antioxidants, and mixtures thereof.

Further non-limiting examples of the therapeutic agents in the pharmaceutical composition include: acetretin, albendazole, albuterol, aminoglutethimide, amiodarone, amlodipine, amphetamine, amphotericin B, arginine, atorvastatin, atovaquone, azithromycin, baclofen, beclomethasone, benazepril, benzonatate, betamethasone, bicalutanide, budesonide, bupropion, busulfan, butenafine, calcifediol, calcipotriene, calcitriol, camptothecin, candesartan, capsaicin, captopril, carbamezepine, carotenes, celecoxib, cerivastatin, cetirizine, chlorpheniramine, cholecalciferol, cilazepril, cilostazol, cimetidine, cinnarizine, ciprofloxacin, cisapride, clarithromycin, clemastine, clomiphene, clomipramine, clonidine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, doxazosin, efavirenz, eprosartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenyloin, frovatriptan, fuirazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketenserin, ketoconazole, ketorolac, lamotrigine, lansoprazole, leflunomide, lisinopril, loperamide, loratadine, losartan, lovastatin, L-thryroxine, lutein, lycopene, medroxyprogesterone, mifepristone, mefloquine, megestrol acetate, methadone, methoxsalen, methyldopa, metronidazole, miconazole, midazolam, miglitol, minoxidil, mitoxantrone, montelukast, moxonidine, nabumetone, nalbuphine, naratriptan, nelfinavir, nifedipine, nilsolidipine, nilutanide, nitrofurantoin, nitroglycerin, nizatidine, omeprazole, oprevelkin, oestradiol, oxaprozin, paclitaxel, paracalcitol, paroxetine, pentazocine, pioglitazone, pizofetin, prazosin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremitfene, tramadol, tretinoin, troglitazone, trovafloxacin, ubidecarenone, urapidil, valsartan, venlafaxine, verteporfin, vigabatrin, vitamin A, vitamin D, vitamin E, vitamin K, zafirlukast, zileuton, zolmitriptan, zolpidem, zopiclone, pharmaceutically acceptable salts, isomers, and derivatives thereof, and mixtures thereof.

In certain aspects of the invention, the therapeutic agent in the pharmaceutical composition is an antiproliferative or chemotherapeutic drug. Exemplary antiproliferative or chemotherapeutic drugs include, but are not limited to, Abarelix, aldesleukin, Aldesleukin, Alemtuzumab, Alitretinoin, Allopurinol, Altretamine, Amifostine, Anastrozole, Arsenic trioxide, Asparaginase, Azacitidine, β-lapachone, BCG Live, Bevacuzimab, Avastin, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cisplatin, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, and Zoledronic acid.

In certain embodiments the therapeutic agent of the pharmaceutical composition is a protein or polypeptide. The protein or polypeptide can be a cytokine or growth factor (such as VEGF, FGF, MCP-1, PIGF, KGF, PDGF), or an antibody or binding portion thereof.

In a further embodiment, the therapeutic agent of the pharmaceutical composition is a radioprotective agent. Exemplary radioprotective agents include, but are not limited to, amifostine, growth factors as their derivatives such as PDGF and KGF (Palifermin=KGF derivative), manganese superoxide dismutase transgene delivery, tetracycline, p53 Up-regulated modulator of apoptosis ("PUMA") inhibitors (Mustata et al., *Curr Top Med Chem* 11(3):281-90 (2011); Greenberger et al., *Front Oncol* 1:59 (2011), each of which is hereby incorporated by reference in its entirety), BEB55, genistein (4',5,7-trihydroxyisoflavone), ACE inhibitors such as captopril and perindopril, 3,3'-diindolylmethane (DIM), ON01210 (a chlorobenzylsulfone derivative known as Ex-RAD), gamma-tocotrienol (GT3), δ-tocotrienol, R-spondin1 (Rspo1), flagellin and flagellin variants such as CBLB502/Entolimod™, interleukins such as IL2 and IL6, and cytokines such as tumor necrosis factor and transforming growth factor-β3.

In certain embodiments, the therapeutic agent of the pharmaceutical composition is a cardioprotective agent selected from the group of α1 adrenoceptor antagonist, α2 blocker, anti-hypotensive agent, angiotensin receptor blockers/ACE inhibitor, angiotensin-1 blockers, endopeptidase, β2 agonists, β2 blockers, diuretics, calcium channel blockers, anti-arrhythmic agents, anti-angiogenic agents, a corticosteroid, VEGF antagonists, and a statin. Non-limiting exemplary cardioprotective agents are prazosin, terazosin, doxazosin, ketenserin, urapidil, arginine, nitroglycerin, clonidine, methyldopa, moxonidine, hydralazine minoxidil, benezepril, captopril, cilazepril, enalapril, fosinopril, lisinopril, perindopril, quinapril, ramipril, trandolapril, zofenopril, candesartan, eprosartan, irbesartan, losartan, telmisartan, valsartan, omapatrilate, acebutolol, atenolol, bisoprolol, celiprolol, esmodol, metoprolol, nebivolol, betaxolol, carvedilol, labetalol, oxprenolol, pindolol, propanolol, chlortalidon, chlorothiazide, epitizide, hydrochlorthiazide, indapamide, amiloride, triamterene, amlodipin, barnidipin, diltiazem, felodipin, isradipin, lacidipin, lercanidipin, nicardipin, nifedipin, nimodipin, nitrendipin, verapamil, amiodarone, solatol, diclofenac, enalapril, flecainide, ciprofloxacin, latanoprost, flucloxacillin, rapamycin and analogues, triamcinolone acetonide, dexamethasone, fluocinolone acetonide, bevacizumab, ranibizumab, pegaptanib, atorvastatin, fluvastatin, lovastatin, pravastatin, rosuvastatin, simvastatin, and pitavastadn.

In a further embodiment, the therapeutic agent of the pharmaceutical composition is an antioxidant, a coenzyme, a vitamin, a metabolite, or a mineral.

In another embodiment, the therapeutic agent is a nucleic acid molecule. The nucleic acid molecule may be in the form of RNA, DNA, hybrid RNA-DNA, ribozyme, aptamers, RNAi (siRNA, miRNA, antisense oligos), or a modified nucleic acid molecule having modified backbones, sugars, or nucleobases. In certain embodiments, the nucleic acid molecule is DNA in the form of a vector such as a plasmid or virus particle (containing a modified viral genome).

According to one approach, the nucleic acid molecule (or its encoded products) may be used to introduce one or more defects into mitochondrial DNA to disrupt function of a mitochondrial gene. This is particularly desirable for causing cell death of certain cell types, such as cancer cells. According to another approach, the nucleic acid molecule (or its encoded products) may be used to correct errors in mitochondrial DNA to alter function of a mitochondrial gene. This may be desirable for using stem cell therapies to treat one or more disease conditions associated with mitochondrial gene defects. Exemplary targets within the mitochondrial DNA include, without limitation, MT-ATP-8, MT-ATP6, MT-CO1, MT-CO2, MT-CO3, MT-CYB, MT-ND1, MT-ND2, MT-ND3, MT-ND4 L, MT-ND4, MT-ND5, MT-ND6, MT-RNR2, any of the MT-transfer RNA sequences, or MT-ribosomal RNA sequences.

The nucleic acid molecule may optionally encode one or more therapeutic RNA molecules that are active in modifying mitochondrial function, or more or more proteins or polypeptides that active in modifying mitochondrial function, or both. Exemplary RNA molecules that are active in modifying mitochondrial function include, without limitation, RNAi molecules, aptamers, or ribozymes that target mitochondrial genes.

According to another embodiment, the therapeutic agent is a interbacterial toxin that catalyses the deamination of cytidines within dsDNA, and has been identified as DddA. According to one approach, the DddA exists in the form of split-DddA halves that are each non-toxic and inactive until brought together on target DNA by adjacently bound programmable DNA-binding proteins. This approach is described in Mok et al., "A Bacterial Cytidine Deaminase Toxin Enables CRISPR-free Mitochondrial Base Editing," *Nature* 583(7817):631-637 (2020), which is hereby incorporated by reference in its entirety, where fusions of the split-DddA halves, transcription activator-like effector array proteins, and a uracil glycosylase inhibitor resulted in RNA-free DddA-derived cytosine base editors that catalyze C·G-to-T·A conversions in human mtDNA with high target specificity and product purity.

In some embodiments, the therapeutic agent comprises or encodes a nuclease agent and a nuclease agent recognition site to enhance homologous recombination events of an insert polynucleotide (or DNA template) into a target locus, particularly though not exclusively mitochondrial DNA. The term "recognition site for a nuclease agent" includes a DNA sequence at which a nick or double-strand break is induced by a nuclease agent. The recognition site for a nuclease agent is preferably native, and preferably in one of the above-identified mitochondrial DNA targets. The length of the recognition site can vary depending on the nuclease, and includes, for example, recognition sites that are about 20 bp for a CRISPR/Cas9 guide RNA.

Any nuclease agent that induces a nick or double-strand break into a desired recognition site can be used in the methods and compositions disclosed herein. A naturally occurring or native nuclease agent can be employed so long as the nuclease agent induces a nick or double-strand break in a desired recognition site. Alternatively, a modified or engineered nuclease agent can be employed. An "engineered nuclease agent" includes a nuclease that is engineered (modified or derived) from its native form to specifically recognize and induce a nick or double-strand break in the desired recognition site. Thus, an engineered nuclease agent can be derived from a native naturally occurring nuclease agent or it can be artificially created or synthesized. The modification of the nuclease agent can be as little as one amino acid in a protein cleavage agent or one nucleotide in a nucleic acid cleavage agent. In some embodiments, the engineered nuclease induces a nick or double-strand break in a recognition site, wherein the recognition site was not a sequence that would have been recognized by a native (non-engineered or non-modified) nuclease agent. Producing a nick or double-strand break in a recognition site or other DNA can be referred to herein as "cutting" or "cleaving" the recognition site or other DNA.

The nuclease agent employed in the various methods and compositions described herein preferably comprises a CRISPR/Cas system. Such systems can employ a Cas9 nuclease or any other suitable nuclease, which in some instances, is codon-optimized for the desired cell type in which it is to be expressed and/or modified to replace the native nuclear localization signal with a mitochondrial localization signal, e.g., the amino-terminal leader peptide of ornithine transcarbamylase such as amino acids 1-32 of human ornithine transcarbamylase (see UniProtKB—P00480; Hussain et al., "Adapting CRISPR/Cas9 System for Targeting Mitochondrial Genome," *Front. Genet.*, DOI: 10.3389/fgene.2021.627050 (2021); and Seibel et al., "Transfection of Mitochondria: Strategy Towards a Gene Therapy of Mitochondrial DNA Diseases," *Nucleic Acids Res.* 23:10-17 (1995), each of which is hereby incorporated by reference in its entirety) and amino acids 1-25 of human cytochrome oxidase subunit 8 (see UniProtKB—P10176; Hussain et al., "Adapting CRISPR/Cas9 System for Targeting Mitochondrial Genome," *Front. Genet.*, DOI: 10.3389/fgene.2021.627050 (2021); and Bacman et al., "Specific Elimination of Mutant Mitochondrial Genomes in Patient-derived Cells by mitoTALENs," *Nat. Med.* 19:1111-1113 (2013), each of which is hereby incorporated by reference in its entirety). While optional, due to the mitochondrial delivery afforded by the branched peptides of the present invention, such signal peptides may facilitate mitochondrial retention of the Cas nuclease. The system further employs a fused crRNA-tracrRNA construct that functions with the optimized Cas nuclease. This single RNA is often referred to as a guide RNA or gRNA. Within a gRNA, the crRNA portion is identified as the 'target sequences' for the given recognition site and the tracrRNA is often referred to as the 'scaffold'. The gRNA may also be provided with a 20-nucleotide stem-loop element (RP-loop) that is a component of nuclear RNAse P at the 5' end of the guide (see Hussain et al., "Adapting CRISPR/Cas9 System for Targeting Mitochondrial Genome," *Front. Genet.*, DOI: 10.3389/fgene.2021.627050 (2021), which is hereby incorporated by reference in its entirety). According to one approach, the gRNA and modified Cas nuclease, in the form of a Cas9-gRNA complex ("RNP"), can be encapsulated within the micelle of the branched peptide for delivery into mitochondria.

Alternatively, a short DNA fragment containing the target sequence is inserted into a guide RNA expression plasmid. The gRNA expression plasmid comprises the target sequence (in some embodiments around 20 nucleotides), a form of the tracrRNA sequence (the scaffold) as well as a suitable promoter that is active in the cell and necessary elements for proper processing in eukaryotic cells. Many of the systems rely on custom, complementary oligos that are annealed to form a double stranded DNA and then cloned into the gRNA expression plasmid. Separate gRNA expression plasmid and Cas9 expression plasmid are then incorporated into the pharmaceutical formulation with the branched peptide of the present invention to facilitate cell uptake and mitochondrial localization of those plasmids gRNA and Cas9.

The methods and compositions disclosed herein can utilize CRISPR/Cas systems or components of such systems to modify a genome within a cell, preferably the mitochondrial genome. CRISPR/Cas systems include transcripts and other elements involved in the expression of, or directing the activity of, Cas genes. A CRISPR/Cas system can be a type I, a type II, or a type III system. The methods and compositions disclosed herein employ CRISPR/Cas systems by utilizing CRISPR complexes (comprising a guide RNA (gRNA) complexed with a Cas protein) for site-directed cleavage of nucleic acids.

Some CRISPR/Cas systems used in the methods disclosed herein are non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together.

Cas proteins generally comprise at least one RNA recognition or binding domain. Such domains can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage. Cleavage includes the breakage of the covalent bonds of a nucleic acid molecule. Cleavage can produce blunt ends or staggered ends, and it can be single-stranded or double-stranded.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

Cas proteins can be from a type II CRISPR/Cas system. For example, the Cas protein can be a Cas9 protein or be derived from a Cas9 protein. Cas9 proteins typically share four key motifs with a conserved architecture. Motifs 1, 2, and 4 are RuvC-like motifs, and motif 3 is an HNH motif. The Cas9 protein can be from, for example, *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina*. Additional examples of the Cas9 family members are described in WO 2014/131833, which is hereby incorporated by reference in its entirety. Cas9 protein from *S. pyogenes* or derived therefrom is a preferred enzyme. Cas9 protein from *S. pyogenes* is assigned SwissProt accession number Q99ZW2, which is hereby incorporated by reference in its entirety.

Cas proteins can be wild type proteins (i.e., those that occur in nature), modified Cas proteins (i.e., Cas protein variants), or fragments of wild type or modified Cas proteins. Cas proteins can also be active variants or fragments of wild type or modified Cas proteins. Active variants or fragments can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease nucleic acid binding affinity, nucleic acid binding specificity, and/or enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Some Cas proteins comprise at least two nuclease domains, such as DNase domains. For example, a Cas9 protein can comprise a RuvC-like nuclease domain and an HNH-like nuclease domain. The RuvC and HNH domains can each cut a different strand of double-stranded DNA to make a double-stranded break in the DNA. See, e.g., Jinek et al., Science 337:816-821 (2012), which is hereby incorporated by reference in its entirety.

Cas proteins can also be fusion proteins. For example, a Cas protein can be fused to a cleavage domain, an epigenetic modification domain, a transcriptional activation domain, or a transcriptional repressor domain. See WO 2014/089290, which is hereby incorporated by reference in its entirety. Cas proteins can also be fused to a heterologous polypeptide providing increased or decreased stability. The fused domain or heterologous polypeptide can be located at the N-terminus, the C-terminus, or internally within the Cas protein.

Cas proteins can also comprise a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g. eBFP, eBFP2, Azurite, mKalama1, GFPuv, Sapphire, T-sapphire), cyan fluorescent proteins (e.g. eCFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism.

Nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. Promoters that can be used in an expression construct include, for example, promoters active in eukaryotic, mammalian, non-human mammalian, human, rodent, mouse, rat, or hamster cells. Examples of other promoters are described elsewhere herein.

A "guide RNA" or "gRNA" includes an RNA molecule that binds to a Cas protein and targets the Cas protein to a specific location within a target DNA. Guide RNAs can comprise two segments: a "DNA-targeting segment" and a "protein-binding segment." "Segment" includes a segment, section, or region of a molecule, such as a contiguous stretch of nucleotides in an RNA. Some gRNAs comprise two separate RNA molecules: an "activator-RNA" and a "targeter-RNA." Other gRNAs are a single RNA molecule (single RNA polynucleotide), which can also be called a "single-molecule gRNA," a "single-guide RNA," or an "sgRNA." See, e.g., WO/2013/176772A1, WO/2014/065596A1, WO/2014/089290A1, WO/2014/093622A2, WO/2014/099750A2, WO/2013142578A1, and WO 2014/131833A1, each of which is hereby incorporated by reference in its entirety. The terms "guide RNA" and "gRNA" include both double-molecule gRNAs and single-molecule gRNAs.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA.

The crRNA and the corresponding tracrRNA hybridize to form a gRNA. The crRNA additionally provides the single-stranded DNA-targeting segment that hybridizes to a CRISPR RNA recognition sequence. If used for modification within a cell, the exact sequence of a given crRNA or tracrRNA molecule can be designed to be specific to the species in which the RNA molecules will be used. See, e.g., Mali et al. Science 339:823-826 (2013); Jinek et al. Science 337:816-821 (2012); Hwang et al., Nat. Biotechnol. 31:227-229 (2013); Jiang et al. Nat. Biotechnol. 31:233-239 (2013); and Cong et al. Science 339:819-823 (2013), each of which is hereby incorporated by reference in its entirety.

The DNA-targeting segment (crRNA) of a given gRNA comprises a nucleotide sequence that is complementary to a sequence in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the Cas9 system and organism but often contain a targeting segment of between 21 to 72 nucleotides length, flanked by two direct repeats (DR) of a length of between 21 to 46 nucleotides (see, e.g., WO2014/131833, which is hereby incorporated by reference in its entirety). In the case of S. pyogenes, the DRs are 36 nucleotides long and the targeting segment is 30 nucleotides long. The 3' located DR is complementary to and hybridizes with the corresponding tracrRNA, which in turn binds to the Cas9 protein.

The DNA-targeting segment can have a length of from about 12 nucleotides to about 100 nucleotides. For example, the DNA-targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt.

The nucleotide sequence of the DNA-targeting segment that is complementary to a nucleotide sequence (CRISPR RNA recognition sequence) of the target DNA can have a length at least about 12 nt. For example, the DNA-targeting sequence (i.e., the sequence within the DNA-targeting segment that is complementary to a CRISPR RNA recognition sequence within the target DNA) can have a length at least about 12 nt, at least about 15 nt, at least about 18 nt, at least about 19 nt, at least about 20 nt, at least about 25 nt, at least about 30 nt, at least about 35 nt, or at least about 40 nt. In some cases, the DNA-targeting sequence can have a length of about 20 nt.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild-type tracrRNA sequence (e.g., about or more than about 20, 26, 32, 45, 48, 54, 63, 67, 85, or more nucleotides of a wild-type tracrRNA sequence). Examples of wild-type tracrRNA sequences from *S. pyogenes* include 171-nucleotide, 89-nucleotide, 75-nucleotide, and 65-nucleotide versions. See, e.g., Deltcheva et al. *Nature* 471:602-607 (2011); WO 2014/093661, each of which is hereby incorporated by reference in its entirety. Examples of tracrRNAs within single-guide RNAs (sgRNAs) include the tracrRNA segments found within +48, +54, +67, and +85 versions of sgRNAs, where "+n" indicates that up to the +n nucleotide of wild-type tracrRNA is included in the sgRNA. See U.S. Pat. No. 8,697,359, which is hereby incorporated by reference in its entirety.

The percent complementarity between the DNA-targeting sequence and the CRISPR RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the CRISPR RNA recognition sequence within the target DNA can be at least 60% over about 20 contiguous nucleotides. As an example, the percent complementarity between the DNA-targeting sequence and the CRISPR RNA recognition sequence within the target DNA is 100% over the 14 contiguous nucleotides at the 5' end of the CRISPR RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the CRISPR RNA recognition sequence within the target DNA is 100% over the seven contiguous nucleotides at the 5' end of the CRISPR RNA recognition sequence within the complementary strand of the target DNA and as low as 0% over the remainder. In such a case, the DNA-targeting sequence can be considered to be 7 nucleotides in length.

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as separate DNA molecules encoding the crRNA and tracrRNA, respectively.

DNAs encoding gRNAs can be stably integrated in the genome of the cell and operably linked to a promoter active in the cell. Alternatively, DNAs encoding gRNAs can be operably linked to a promoter in an expression construct. Such promoters can be active, for example, in a pluripotent rat, eukaryotic, mammalian, non-human mammalian, human, rodent, mouse, or hamster cell. In some instances, the promoter is an RNA polymerase III promoter, such as a human U6 promoter, a rat U6 polymerase III promoter, or a mouse U6 polymerase III promoter. Examples of other promoters are described elsewhere herein.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is hereby incorporated by reference in its entirety). Guide RNAs can also be a synthetically produced molecule prepared by chemical synthesis.

The term "CRISPR RNA recognition sequence" includes nucleic acid sequences present in a target DNA to which a DNA-targeting segment of a gRNA will bind, provided sufficient conditions for binding exist. For example, CRISPR RNA recognition sequences include sequences to which a guide RNA is designed to have complementarity, where hybridization between a CRISPR RNA recognition sequence and a DNA targeting sequence promotes the formation of a CRISPR complex. Full complementarity is not necessarily required, provided there is sufficient complementarity to cause hybridization and promote formation of a CRISPR complex. CRISPR RNA recognition sequences also include cleavage sites for Cas proteins, described in more detail below. A CRISPR RNA recognition sequence can comprise any polynucleotide, which can be located, for example, in the nucleus or cytoplasm of a cell or within an organelle of a cell, such as a mitochondrion or chloroplast.

The CRISPR RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), which is hereby incorporated by reference in its entirety). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a CRISPR RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "CRISPR RNA recognition sequence." The cleavage site can be on only one strand or on both strands of a nucleic acid. Cleavage sites can be at the same position on both strands of the nucleic acid (producing blunt ends) or can be at different sites on each strand (producing staggered ends). Staggered ends can be produced, for example, by using two Cas proteins, each of which produces a single-strand break at a different cleavage site on each strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the CRISPR RNA recognition sequence of the nickase on the first strand is separated from the CRISPR RNA recognition sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific cleavage of target DNA by Cas9 can occur at locations determined by both (i) base-pairing complementarity between the gRNA and the target DNA and (ii) a short motif, called the protospacer adjacent motif (PAM), in the target DNA. The PAM can flank the CRISPR RNA recognition sequence. Optionally, the CRISPR RNA recognition sequence can be flanked by the PAM. For example, the cleavage site of Cas9 can be about 1 to about 10 or about 2 to about 5 base pairs (e.g., 3 base pairs) upstream or downstream of the PAM sequence. In some cases (e.g., when Cas9 from S. pyogenes or a closely related Cas9 is used), the PAM sequence of the non-complementary strand can be 5'-$N_1$GG-3', where $N_1$ is any DNA nucleotide and is immediately 3' of the CRISPR RNA recognition sequence of the non-complementary strand of the target DNA. As such, the PAM sequence of the complementary strand would be 5'-CC$N_2$-3', where $N_2$ is any DNA nucleotide and is immediately 5' of the CRISPR RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T, $N_1$=T, and $N_2$=A).

Examples of CRISPR RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas protein (see, e.g., WO 2014/165825). The guanine at the 5' end can facilitate transcription by RNA polymerase in cells. Other examples of CRISPR RNA recognition sequences can include two guanine nucleotides at the 5' end (e.g., GG$N_{20}$NGG, SEQ ID NO:76) to facilitate efficient transcription by T7 polymerase in vitro. See, e.g., WO 2014/065596, which is hereby incorporated by reference in its entirety.

The CRISPR RNA recognition sequence can be any nucleic acid sequence endogenous to a cell. The CRISPR RNA recognition sequence is preferably located upstream of the first exon in a native defective gene (to be corrected), and more preferably is located downstream of the native promoter sequence but upstream of the first exon. In one embodiment, the target sequence is immediately flanked by a Protospacer Adjacent Motif (PAM) sequence. In one embodiment, the gRNA comprises a third nucleic acid sequence encoding a Clustered Regularly Interspaced Short Palindromic Repeats (CRISPR) RNA (crRNA) and a trans-activating CRISPR RNA (tracrRNA).

Regardless of the type of therapeutic agent to be delivered, the branched peptide of the pharmaceutical composition is present at a concentration of from about 100 nM to about 500 μM. Furthermore, the therapeutic agent can be present in an amount from about 1 nM to about 10 μM. Single doses of the pharmaceutical composition may contain from 0.1 μg to 0.1 g of the branched peptide, preferably 4 μg to 0.04 g or 400 μg to 0.4 g; and any effective amount of the therapeutic agent. Typically, single doses of the therapeutic agent range from 1 μg/kg·body weight to 1000 mg/kg·body weight (although lesser or greater dosages are also contemplated).

In some embodiments, the carrier is an aqueous medium. In one embodiment, the aqueous medium is a sterile isotonic aqueous buffer, which is typically well tolerated for administration to an individual. Additional exemplary aqueous media include, without limitation, normal saline (about 0.9% NaCl), phosphate buffered saline ("PBS"), sterile water/distilled autoclaved water ("DAW"), as well as cell growth medium (e.g., MEM, with or without serum), aqueous solutions of dimethyl sulfoxide ("DMSO"), polyethylene glycol ("PEG"), and/or dextran (less than 6% per by weight).

To improve patient tolerance to administration, the pharmaceutical composition may have a pH of about 4.5 to about 8.5. In some embodiments, sodium hydroxide or hydrochloric is added to the pharmaceutical composition to adjust the pH.

In other embodiments, the pharmaceutical composition includes a weak acid or salt as a buffering agent to maintain pH. Citric acid has the ability to chelate divalent cations and can thus also prevent oxidation, thereby serving two functions as both a buffering agent and an antioxidant stabilizing agent. Citric acid is typically used in the form of a sodium salt, typically 10-500 mM. Other weak acids or their salts can also be used.

The pharmaceutical composition may also include solubilizing agents, preservatives, stabilizers, emulsifiers, and the like. A local anesthetic (e.g., lidocaine, benzocaine, etc.) may also be included in the compositions, particularly for injectable forms, to ease pain at the site of the injection.

Another aspect of the present invention relates to enzymatic cleavage products of the branched peptides, whereby cleavage of the second peptide chain disrupts the ability of the (resulting cleaved) branched peptide to form micelle structures. Instead, given the loss of a portion of the second peptide chain from the branched peptide, the resulting product is capable of self-assembly to form nanofibers and possibly larger hydrogel assemblies containing those nanofibers.

Thus, in one embodiment, the invention relates to a nanofiber formed in an aqueous medium which includes self-assembled, enzymatically modified forms of the branched peptide as described herein. As used herein, the term "nanofiber" is defined as a fiber of material having any shape wherein at least one dimension, e.g. the diameter, width, thickness, and the like, is about 100 nm or less. Nanofiber diameters may be about 50 nm or less, about 40 nm or less, about 30 nm or less, about 20 nm or less, about 10 nm or less, about 5 nm or less, about 4 nm or less, about 3 nm or less, about 2 nm or less, or about 1 nm or less in diameter. Although the peptides of the present invention, upon self-assembly, as described herein, form nanofibers, persons of skill in the art should appreciate that such peptides may also form microfibrils that are larger than 100 nm thick.

In another embodiment, the invention relates to a supramolecular hydrogel formed in an aqueous medium that includes a self-assembled, enzymatically modified form of the branched peptide.

In these embodiments, the nanofiber or supramolecular hydrogel includes the enzymatically modified form of the branched peptide as described above. Exemplary enzymatically modified forms of the branched peptides include, without limitation, the following: Nap-FFK($^e$G)Y, Nap-FFFK($^e$G)Y, Nap-FFGK($^e$G)Y, Nap-FFGK($^e$G), Nap-FFGK($^e$G)F, Nap-ffk($^e$G)y, Nap-fffk($^e$G)y, Nap-ffgk($^e$G)y, Nap-ffgk($^e$G), Nap-ffgk($^e$G)f, Nap-FFK($^e$G)(Dmt), Nap-FFFK($^e$G)(Dmt), Nap-FFGK($^e$G)(Dmt), Nap-ffk($^e$G)(dmt), Nap-fffk($^e$G)(dmt), Nap-ffgk($^e$G)(dmt), Nap-FFC($^e$G)Y, Nap-FFFC($^e$G)Y, Nap-FFGC($^e$G)Y, Nap-FFGC($^e$G), Nap-FFGC($^e$G)F, Nap-ffc($^e$G)y, Nap-fffc($^e$G)y, Nap-ffgc($^e$G)y, Nap-ffgc($^e$G), Nap-ffgc($^e$G)f, Nap-FFC($^e$G)(Dmt), Nap-FFFC($^e$G)(Dmt), Nap-FFGC($^e$G)(Dmt), Nap-ffc($^e$G)(dmt), Nap-fffc($^e$G)(dmt), and Nap-ffgc($^e$G)(dmt), and where the nanofiber or supramolecular hydrogel optionally includes an enzymatically unmodified form of the branched peptide, which may be incorporated into the same.

In addition, where combinations of branched peptides are present in the pharmaceutical composition, then nanofibers and supramolecular hydrogels formed by the enzymatically modified forms of the branched peptides may also include combinations thereof. These nanofibers and supramolecular hydrogels that contain combinations of enzymatically modified forms of the branched peptides may or may not contain a tethered therapeutic agent (Z).

Based on the various combinations of therapeutic agents, both tethered and micelle-containing, and combinations thereof, the branched peptides can be used to deliver the therapeutic agents in patients for the treatment of various disease conditions.

Therefore, one aspect of the invention relates to a method of delivering a therapeutic agent into mitochondria comprising encapsulating a therapeutic agent within a micelle structure of a pharmaceutical composition as described herein, and then contacting a cell with the pharmaceutical composition, whereby micelle structures are taken up by the cell and targeted to mitochondria within the cell. When the micelle structure is altered by way of enzymatic cleavage of the second peptide chain, the micelle-delivered therapeutic agent is released into the contacted cell adjacent to the mitochondria and/or actively taken up by the mitochondria.

A related aspect of the invention relates to causing cell death of a cancerous cell. This is carried out by delivering a therapeutic agent into mitochondria by encapsulating the therapeutic agent within a micelle structure of a pharmaceutical composition as described herein, and then contacting the cancerous cell with the pharmaceutical composition, whereby micelle structures are taken up by the cell and targeted to mitochondria within the cell. When the micelle structure is altered by way of enzymatic cleavage of the second peptide chain, the micelle-delivered therapeutic agent is released into the contacted cell adjacent to the mitochondria and/or actively taken up by the mitochondria. The therapeutic agent will disrupt one or more critical mitochondrial genes or one or more critical pathways in the mitochondria, and thereby cause cancer cell death.

Some embodiments of the method relate to the delivering of a therapeutic agent into mitochondria wherein the cell is ex vivo or in vivo. For in vivo contact to occur, a pharmaceutical composition of the invention is administered to an individual administering is carried out parenterally, subcutaneously, intravenously, intradermally, intramuscularly, intraperitoneally, by implantation, by intracavitary or intravesical instillation, intraarterially, intralesionally, intradermally, peritumorally, intratumorally, or by introduction into one or more lymph nodes. Other modes of administration that are effective to present the micelle to cells that are intentionally targeted (i.e., for delivery of the therapeutic agent) can also be used. The therapeutic agents can be any of the above-identified agents, including gene therapy agents, for use in treating a condition or disease state that implicates mitochondrial function or mitochondrial gene expression.

Administration of the pharmaceutical composition can be repeated on a daily schedule (i.e., once, twice, or thrice daily), or according to a periodic schedule (i.e., once weekly, bimonthly, once monthly).

Individuals that can be treated include both veterinary patients, typically but not exclusively mammals, as well as human patients.

A further aspect of the invention relates to a method of treating a patient having a cancerous condition. This method includes administering a pharmaceutical composition as described herein to a patient having a cancerous condition, where the administering is effective to inhibit cancer cell survival. Modes and frequency of administration, and patient groups include those identified above.

The cancerous conditions to be treated in accordance with this aspect can involve cancer cells present in a solid tumor, present as a metastatic cell, or present in a heterogenous population of cells that includes both cancerous and non-cancerous cells. Exemplary cancer conditions include, without limitation, cancers or neoplastic disorders of the brain and CNS (glioma, malignant glioma, glioblastoma, astrocytoma, multiforme astrocytic gliomas, medulloblastoma, craniopharyngioma, ependymoma, pinealoma, hemangioblastoma, acoustic neuroma, oligodendroglioma, meningioma), pituitary gland, breast (Infiltrating, Pre-invasive, inflammatory cancers, Paget's Disease, Metastatic and Recurrent Breast Cancer), blood (Hodgkin's Disease, Leukemia, Multiple Myeloma, Lymphoma), lymph node cancer, lung (Adenocarcinoma, Oat Cell, Non-small Cell, Small Cell, Squamous Cell, Mesothelioma), skin (melanoma, basal cell, squamous cell, Kaposi's Sarcoma), bone cancer (Ewing's Sarcoma, Osteosarcoma, Chondrosarcoma), head and neck (laryngeal, pharyngeal, and esophageal cancers), oral (jaw, salivary gland, throat, thyroid, tongue, and tonsil cancers), eye, gynecological (Cervical, Endrometrial, Fallopian, Ovarian, Uterine, Vaginal, and Vulvar), genitourinary (Adrenal, bladder, kidney, penile, prostate, testicular, and urinary cancers), and gastrointestinal (appendix, bile duct (extrahepatic bile duct), colon, gallbladder, gastric, intestinal, liver, pancreatic, rectal, and stomach cancers).

In this aspect of the invention, the pharmaceutical composition contains the branched peptide in combination with a cancer therapeutic agent of the type described above, where the cancer therapeutic agent is tethered to the first peptide chain, introduced separately to the pharmaceutical composition and encapsulated within the micelle structure, both are used together to deliver different forms of the same therapeutic agent (i.e., tethered and untethered forms of the same active agent), or both are used to deliver two different therapeutic agents in combination (i.e., one therapeutic agent tethered and the other untethered but encapsulated within the micelle structure).

While any class of antineoplastic agent, anticancer drug, or chemotherapeutic drug is contemplated for use in connection with the present invention, exemplary agents within these classes include alkylating agents, platinum drugs, antimetabolites, anthracycline and nonanthracycline antitumor antibiotics, topoisomerase inhibitors, mitotic inhibitors, corticosteroids and targeted cancer therapies (such as imatinib, Gleevec®; gefitinib, Iressa®; sunitinib, Sutent®; and bortezomib, Velcade®).

In this aspect of the invention, chemotherapeutic agents can be delivered in one embodiment of the pharmaceutical composition (as described above), and gene therapy agents can be delivered in a second embodiment of the pharmaceutical composition (to knock down or knock out mitochondrial gene expression), either for co-administration or contemporaneous administration, to enhance the killing of cancer cells.

A further aspect of the invention relates to a method of treating an individual exposed to radiation. This method includes administering a pharmaceutical composition as described herein to an individual exposed to, or about to be exposed to, radiation, where the administering is effective to inhibit radiation-induced damage to cells of the individual. Modes and frequency of administration, and patient groups include those identified above. More particularly, administration prior to radiation and/or after radiation exposure is contemplated, including two or more rounds of treatment prior to radiation and two or more rounds of treatment after exposure to radiation. For multiple radiation treatments, the same or different schedule for administration of the pharmaceutical compositions as described herein can be used.

In this aspect of the invention, different forms of the pharmaceutical composition (i.e., containing different therapeutic agents) can be administered at different times. For example, a pharmaceutical composition containing a first therapeutic agent (i.e., with either a tethered or micelle encapsulated therapeutic agent) can be administered prior to radiation, and a second therapeutic agent (i.e., with either a tethered or micelle encapsulated therapeutic agent) can be administered following radiation. In this way, combinations of therapeutic agents that maximize recovery and minimize side effects associated with radiation can be utilized.

Yet another aspect of the invention relates to a method of treating a patient for a cardiovascular disease or condition. This method includes administering a pharmaceutical composition as described herein to an individual having a cardiovascular disease or condition, where the administering is effective to treat the cardiovascular disease or condition. Modes and frequency of administration, and patient groups include those identified above.

Exemplary types of cardiovascular disease or conditions include, but are not limited to, atherosclerosis, arrhythmia, cardiomyopathy, coronary heart disease, infarction, angina, hemorrhagic stroke, ischemic stroke, hypertension, heart failure, peripheral artery disease.

In this aspect of the invention, the pharmaceutical composition contains the branched peptide in combination with a therapeutic agent suitable for treating a cardiovascular disease or condition, including those described above, where the therapeutic agent is tethered to the first peptide chain, introduced separately to the pharmaceutical composition and encapsulated within the micelle structure, both are used together to deliver different forms of the same therapeutic agent (i.e., tethered and untethered forms of the same active agent), or both are used to deliver two different therapeutic agents in combination (i.e., one therapeutic agent tethered and the other untethered but encapsulated within the micelle structure).

In addition to the foregoing, the branched peptide can be used to deliver any other class of therapeutic agents to mitochondria for the treatment of a disease state or condition that implicates mitochondrial function, either by improving mitochondrial function or by disrupting mitochondrial function.

EXAMPLES

The examples below are intended to exemplify the practice of embodiments of the disclosure but are by no means intended to limit the scope thereof.

Materials and Methods for Examples 1-5

Materials: All amino acid derivatives involved in the synthesis were purchased from GL *Biochem* (Shanghai) Ltd. N, N-diisopropylethylamine (DIPEA), O-benzotriazole-N, N,N',N'-tetramethyluronium-hexafluorophosphate (HBTU) were purchased from Fisher Scientific. The synthesis of all peptide fragments was based on solid-phase peptide synthesis (SPPS). The branched peptides were made via the combination of SPPS and liquid phase synthesis. All crude compounds were purified by HPLC with the yield of 70-80%. All reagents and solvents were used as received without further purification unless otherwise stated.

Minimum Essential Medium (MEM) for HeLa and U87MG cells culture were purchased from ATCC, fetal bovine serum (FBS) and penicillin/streptomycin from Gibco/Life Technologies, and 3-(4,5-Dimethylthiazol-2-yl)-2,5-diphenyltetrazolium bromide (MTT) from ACROS Organics.

Mitochondria isolation kit was purchased from Sigma-Aldrich. The mitochondria were isolated according to the protocol provided by the company.

Instruments: All peptides were purified by Water Delta600 HPLC system, equipped with an XTerra C18 RP column. LC-MS was operated on a Waters Acquity Ultra Performance LC with Waters MICRO-MASS detector. $^1$H-NMR spectra were gained on Varian Unity Inova 400 with Deuterated DMSO as solvent. Transmission electron microscope (TEM) images were taken on Morgagni 268 transmission electron microscope. Fluorescent analysis was performed on Shimadzu RF-5301-PC fluorescence spectrophotometer. Fluorescence images were taken by ZEISS LSM 880 confocal laser scanning microscope.

Hydrogel TEM Preparation: The hydrogel was placed on glow discharge thin carbon-coated copper grids (400 meshes, Pacific Grid-Tech) and incubated for 30 s at room temperature. 30 seconds later, a large drop of the ddH$_2$O was placed on parafilm and the grid was allowed to touch the water drop with the sample-loaded surface facing the parafilm. The grid was tilted and allowed to gently absorb water from the edge of the grid using a filter paper sliver (repeated 3 times). Immediately after rinsing, staining was performed by placing a large drop of the UA (uranyl acetate, 2% v/v) stain solution on parafilm and allowing the grid to touch the stain solution drop with the sample-loaded surface facing the parafilm. The grid was tilted and allowed to gently absorb the stain solution from the edge of the grid using a filter paper sliver. The grid was air dried and then examined as soon as possible.

Cell/Mitochondria TEM Preparation: Mitochondria were isolated from treated cells using the mitochondria isolation kit from Sigma-Aldrich according to the manufacturer's instructions, and the mitochondria were then placed on glow discharge thin carbon-coated copper grids (400 meshes, Pacific Grid-Tech) and prepared for TEM imaging using the same rinsing and staining procedures described above.

Statistical Analysis of the Fiber Diameters: Using ImageJ Software and obtained TEM images, fiber diameters were measured from each image. Mean and SD of the fibers was obtained from multiple fiber measurements (80) on each TEM image.

Circular Dichroism Measurement: The CD spectra were recorded (185-300 nm) using a JASCO 810 spectrometer under a nitrogen atmosphere. The hydrogel (0.4 wt %, 200 µL) was placed evenly on the 1 mm thick quartz cuvette and scanned with 0.1 nm interval for three times. The percentage of secondary structures in different samples was calculated by the programs provided in DichroWeb.

Cell culture and MTT assay: Cell culture was carried out with MESA/Dx5 cells. These cells were cultured in Macyo's 5A medium supplemented with 10% v/v fetal bovine serum, 100 U/mL penicillin and 100 µg/mL streptomycin. The condition for cell culture was 37° C. in a humidified atmosphere of 5% CO$_2$. The MTT assay was carried out using MESA/Dx5 cells seeded in a 96-well plate with a density of $1*10^4$ cells per-well (total medium volume of 100 µL). 24 hours post seeding, after the removal of the medium, solutions with serial of concentrations (5 concentrations) of the branched peptides were added to each well. Cells without the treatment of the micelles were used as the control. At designated time (24/48/72 hours), 10 µL MTT solution (5 mg/mL) was added to each well and incubated at 37° C. for another 4 h, and then 100 µL of SDS-HCl solution was added to stop the reduction reaction and dissolve the purple formazan. The absorbance of each well at 595 nm was measured by a multimode microplate reader. The cytotoxicity assay was performed three times and the average value of the three measurements was taken. All the statistical analysis used mean±SEM.

Fluorescent Microscopy: Imaging was carried out with HeLa cells. These cells were cultured in MEM medium supplemented with 10% v/v fetal bovine serum, 100 U/mL penicillin and 100 µg/mL streptomycin. The condition for cell culture was 37° C. in a humidified atmosphere of 5% CO$_2$. The imaging was carried out using HeLa cells seeded in a confocal dish with a density of $1*10^5$ cells per-dish (total medium volume of 1 mL). 24 hours post seeding, after the removal of the medium, solutions with specific components were added to each dish. At designed time (2, 4, 24 h), the images of cells in each dish was taken by Zeiss 880 confocal microscope.

Example 1—Synthesis of Branched Peptides

Figure 2:
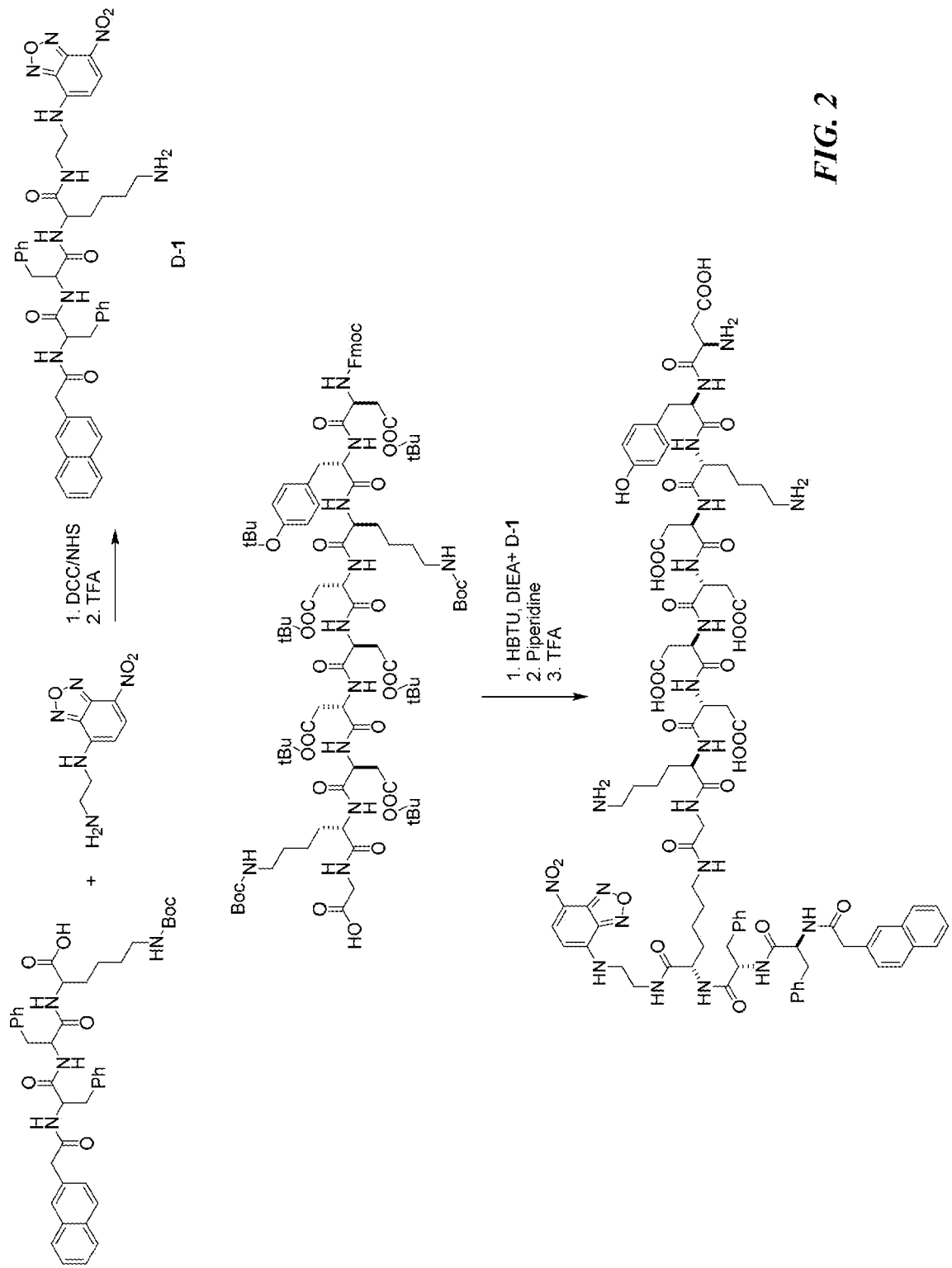
FIG. 2 is an exemplary synthetic route for the formation of branched peptides, and illustrated the structure of D-1, which includes the fluorophore NBD, and its use in the synthesis of D-1 ᴛ FLAG.

FIG. 1 shows the structure of the designed substrate of ENTK. The symbol "⊤" is used to represent the branching so that the substrate is denoted as D-1⊤FLAG. The branched peptides consist of (i) the FLAG-tag (DYKDDDDK, SEQ ID NO: 35) (Hopp et al., *Nat. Biotechnol.* 6(10):1204-1210 (1988), which is hereby incorporated by reference in its entirety) as the substrate of ENTK for enzymatic recognition and cleavage, (ii) a self-assembling peptide sequence D-1 composed of a 2-acetylnaphthyl group (Nap), a D-tripeptide (D-Phe-D-Phe-D-Lys (ffk)), and a nitrobenzoxadiazoly-ethylenediamino moiety (NBD-EA, for enhanced fluorescence upon self-assembly (Gao et al., *Nat. Commun.* 3:1033:1-19 (2012), which is hereby incorporated by reference in its entirety)) at the C-terminal of the D-peptide, and (iii) a glycine residue as the spacer amino acid residue at the C-terminus of the FLAG-tag, i.e., between (i) and the lysine side chain of (ii). Using Fmoc-based solid-phase peptide synthesis (Chan & White, eds., *Fmoc Solid Phase Peptide Synthesis*, Oxford University Press (2000), which is hereby incorporated by reference in its entirety), first the peptide segments DYKDDDDKG (SEQ ID NO: 75) and Nap-ffk were produced (FIG. 2). After the synthesis, D-1 was generated by conjugating NBD-EA to the Nap-ffk peptide via C-terminal activation. Subsequently, the C-terminal of DYKDDDDKG (SEQ ID NO: 75) was connected to the side chain of lysine in D-1 using the same activation method. Finally, the removal of all protecting groups and then purification by high pressure liquid chromatography (HPLC) produce the designed branch peptide (i.e., D-1⊤FLAG).

Figure 3:
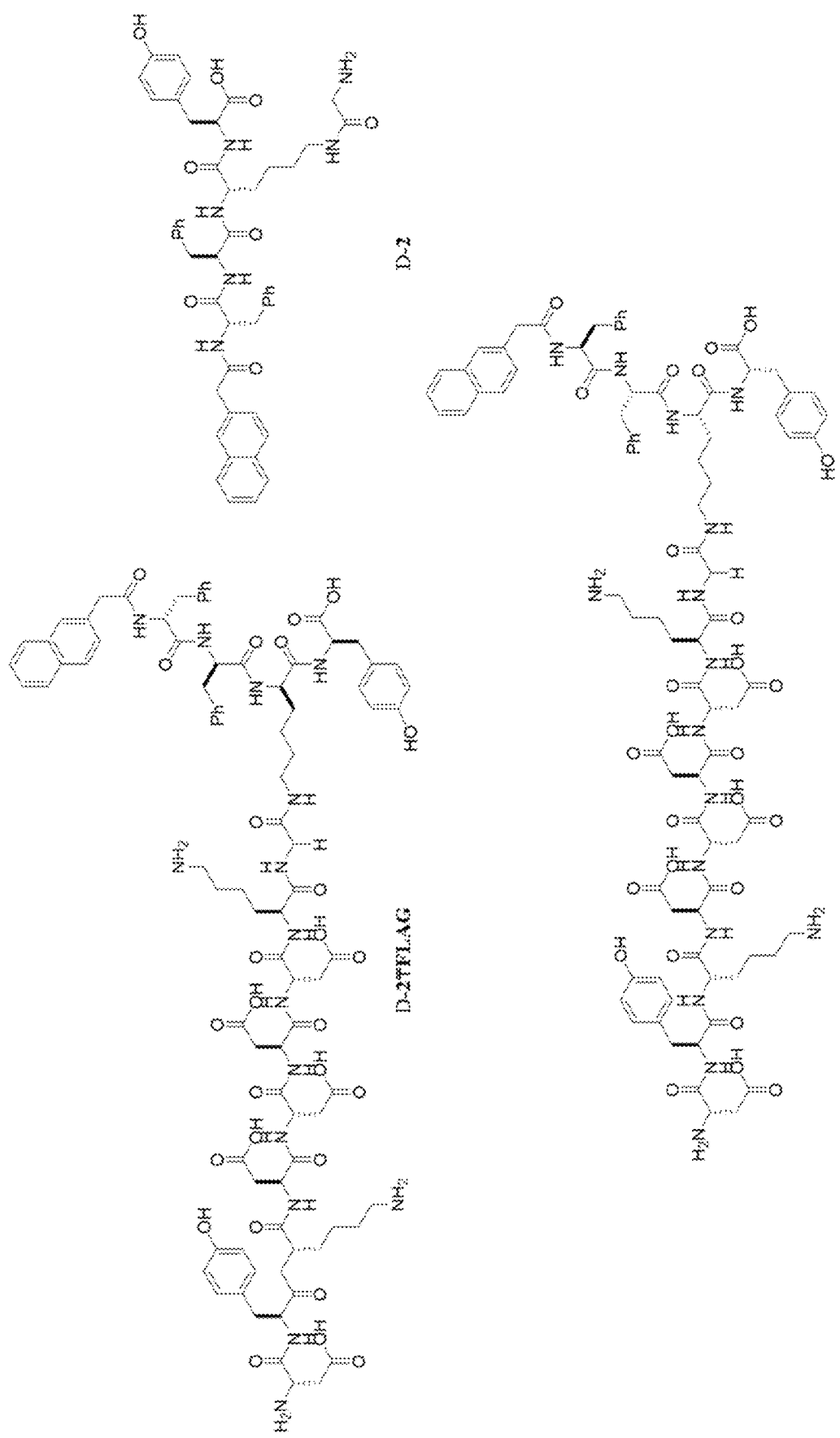
FIG. 3 illustrates the molecular structures of D-2 ᴛ FLAG, D-2, and L-2 ᴛ FLAG.

Similar procedures were performed to produce D-2 ⊤FLAG and L-2⊤FLAG, which contain the Nap-ffky (D-2) and Nap-FFKY (L-2, SEQ ID NO: 1) sequences without the C-terminal NBD moiety (FIG. 3). In FIG. 3, the $^\varepsilon$Gly moiety is shown linked to the Lys sidechain, forming the —NH—C(O)— bond. Upon coupling the Gly moiety to the C-terminus of DYKDDDDK (SEQ ID NO: 35), protected precursors were formed. Removal of all protecting groups and the purification by high pressure liquid chromatography (HPLC) produce the designed, branched peptides D-2⊤FLAG and L-2⊤FLAG.

Example 2—Self Assembly of Enzyme Activated Peptides

Figure 4:
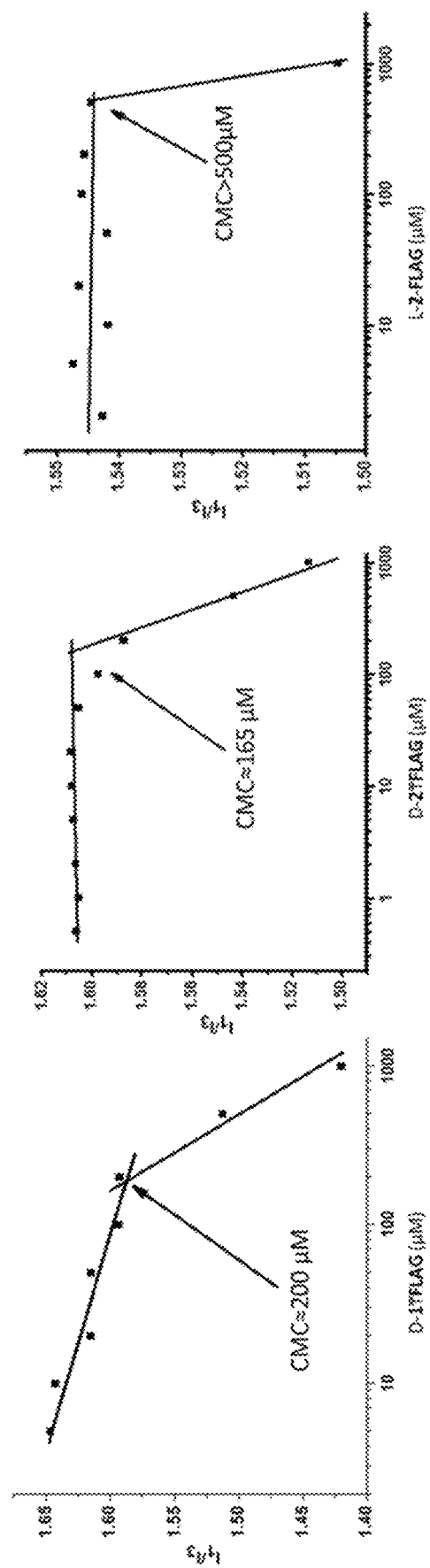
FIG. 4 is the graphical illustration of the critical micelle concentration ("CMC") of D-1 ᴛ FLAG, D-2 ᴛ FLAG and L-2-FLAG in PBS buffer.
Figure 5:
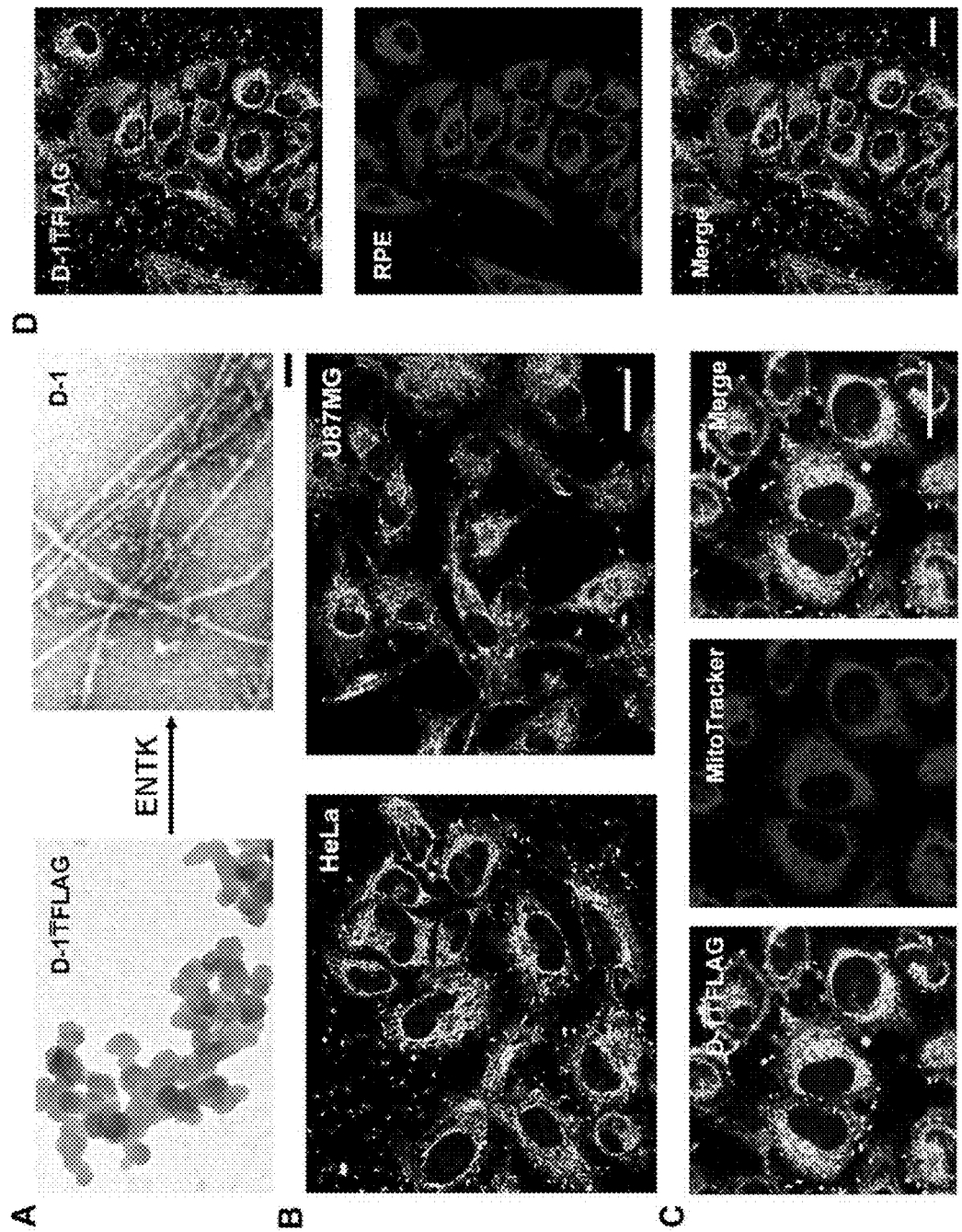
FIGS. 5A-D are representative fluorescent and TEM images of D-1 ᴛ FLAG.

D-1⊤FLAG was dissolved in PBS buffer to a final concentration 200 µM. ENTK (10 U/mL) was added to the solution of D-1⊤FLAG (200 µM), and the solution was incubated at room temperature for 24 h. TEM was then used to observe the micromorphology of D-1⊤FLAG before and after ENTK addition. It was found that D-1⊤FLAG forms nanoparticles (46±11 nm in diameter) at 200 µM (critical micelle concentration (CMC), FIG. 4), which become nanofibers (18±3 nm in diameter) upon the addition of ENTK (FIG. 5A). Circular dichroism (CD) measurement indicates the cleavage of the branch results in largely β-sheet (D-1) and random-coil (FLAG-tag) like secondary structures for the case of D-1 ⊤ FLAG, as well as for those of D-2 ⊤ FLAG and L-2 ⊤ FLAGs (FIG. 3).

Example 3—Cell Uptake of Branched Peptides

200 μM of D-1 ⊤ FLAG was dissolved in MEM medium. HeLa and U87MG cells were incubated with D-1 ⊤ FLAG (200 μM) for 2 h. Zeiss 880 confocal microscope was used to observe the intracellular distribution of D-1 ⊤ FLAG. The mitochondria of HeLa cells were stained by MitoTracker®-DeepRed (Thermofisher Scientific).

After the incubation of HeLa or U87MG cells with D-1 ⊤ FLAG for two hours, fluorescent imaging (FIG. 5B) of these the cells exhibits strong fluorescence, indicating a rapid cellular uptake of D-1 ⊤ FLAG. The preliminary endocytosis study confirms that the uptake of the precursors by HeLa cells likely involves macropinocytosis and clathrin-dependent pathway. Cell viability assay reveals that D-1 ⊤ FLAG exhibits little cytotoxicity to HeLa and U87MG cells, excluding the possibility that the rapid internalization of D-1 ⊤ FLAG originates from the increased membrane permeability caused by cell death (Elmore S., *Toxicol. Pathol.* 35(4):495-516 (2007), which is hereby incorporated by reference in its entirety).

The pattern of the distribution of D-1 ⊤ FLAG in cytosol resembles that of mitochondria (FIG. 5B). Co-staining D-1 ⊤ FLAG with MitoTracker® or Lyso-Tracker® (Thermofisher Scientific) in HeLa cells shows that the fluorescence from D-1 ⊤ FLAG mostly overlaps with the fluorescence of MitoTracker® (FIG. 5C), but co-localizes poorly with the fluorescence from Lysotracker®. These results indicate that D-1 ⊤ FLAG, escaping lysosomes after endocytosis, specifically localizes in mitochondria. However, HeLa cells treated by unbranched D-1 exhibit fluorescence both outside the cells (including membrane) and in the cytosol nonspecifically. Thus, it is inferred that the mitochondria-targeting ability of D-1 ⊤ FLAG likely depends on its unique branching architecture, as well as the electrostatic interaction between the FLAG-tag moiety (negative potential, due to carboxylic groups) and the intermembrane space of mitochondria (positive potential, resulted from abundant $H^+$) (Wikstrom, *Nature* 266(5599):271-273 (1977), which is hereby incorporated by reference in its entirety), as illustrated in FIG. 1.

Notably, D-1 ⊤ FLAG appears to accumulate in the lysosomes of a normal cell line (HS-5), but not the cancer cell lines HeLa, U87MG, Saos2, and HepG2.

Example 4—Delivery of Cargo

After mixing R-phycoerythrin (RPE) (1 μg/mL), a protein, with 200 μM D-1 ⊤ FLAG, this mixture, which forms micelles, was used to incubate HeLa cells for two hours. While the control cells (without micelles) show little fluorescence, the cells incubated with RPE and D-1 ⊤ FLAG show fluorescence localized in the mitochondria (FIG. 5D). TEM images of the mixture of RPE and D-1 ⊤ FLAG support the encapsulation of RPE by the micelles (FIG. 6). These results indicate that the micelles formed by D-1 ⊤ FLAG are able to deliver cargo molecules to mitochondria.

Mitochondria targeting of D-1 ⊤ FLAG implies that the micelles formed by other FLAG-tagged precursors made of branched peptides would localize and deliver cargo molecules to mitochondria. Thus, it was examined whether precursors D-2 ⊤ FLAG (also referred to as Mito-FLAG) and L-2 ⊤ FLAG (a diastereomer of D-2 ⊤ FLAG) (see FIG. 3) are able to deliver cargo molecules to mitochondria. The similar CMC values of D-1 ⊤ FLAG and D-2 ⊤ FLAG (FIG. 4) support the interchangeability between them. After mixing RPE, a protein (1 μg/mL), or doxorubicin (Dox) (2 μM), drug molecule, with L-2 ⊤ FLAG or D-2 ⊤ FLAG (200 μM), the micelles formed were used to incubate HeLa or U87MG cells for two hours. While the control cells (without the micelles formed by the precursors) show little fluorescence, the cells incubated with the micelles and the cargo molecules exhibit strong fluorescence (FIGS. 7A-B), indicating that the intracellular delivery of RPE and Dox by L-2 ⊤ FLAG or D-2 ⊤ FLAG. Similar to D-1 ⊤ FLAG, the patterns of the distribution of RPE (or Dox) inside the cells are akin to that of mitochondria.

To further verify whether the FLAG-tagged precursors deliver cargo molecules to mitochondria specifically, the HeLa cells expressing GFP-Cyt c (Goldstein et al., *Nat. Cell Biol.* 2(3):156-162 (2000), which is hereby incorporated by reference in its entirety) or Omi-mcherry (Tait et al., *Dev. Cell* 18(5):802-813 (2010), which is hereby incorporated by reference in its entirety) in mitochondria were incubated with RPE or Dox in the presence of D-2 ⊤ FLAG. Fluorescent images confirm that the fluorescence of RPE or Dox extensively overlaps with that from GFP-cyt c and Omi-mcherry (FIG. 7C). Quantification of the overlap of the fluorescence (Manders et al., *J. Microsc.* 169(3):375-382 (1993), which is hereby incorporated by reference in its entirety) confirms that RPE or Dox alone hardly co-localize with mitochondria, but D-2 ⊤ FLAG significantly boosts the localization of RPE or Dox in mitochondria (FIG. 7D).

Both D-2 ⊤ FLAG and L-2 ⊤ FLAG induce minimal cytotoxicity alone (FIGS. 8A-C). However, Dox, after mixing with D-2 ⊤ FLAG or L-2 ⊤ FLAG, exhibits significantly increased cytotoxicity against HeLa cells compared to Dox only. That is, the branched peptide precursors decrease the $IC_{50}$ of Dox from 3.0 μM to 400 nM (FIG. 8D). In addition, D-2 ⊤ FLAG significantly boosts the activity of Dox against Dox-resistant cancer cell line (MESA/Dx5, (Harker & Sikic, *Cancer Res.* 45(9):4091-4096 (1985), which is hereby incorporated by reference in its entirety) (FIG. 8D). The synergistic effect (FIG. 8E) of Dox and the FLAG-tagged precursors against cancer cells likely originates from the micelles enhancing the uptake of Dox and Dox interfering with mitochondrial DNA. These results confirm the generality that FLAG-tagged branch peptide precursors serve as carriers for delivering cargo molecules to mitochondria.

Example 5—Mechanics of Self-Assembly

To confirm that the nanofibers form at mitochondria after ENTK cleaves the branch of the branched peptides, mitochondria were isolated from HeLa cells incubated with D-2 ⊤ FLAG (200 μM) for different times. HeLa cells were seeded in a 6 cm petri dish and incubated in a cell incubator (37° C., 5% $CO_2$) until confluence. After that, the HeLa cells were incubated with 200 μM D-2 ⊤ FLAG (Mito-Flag) dissolved in MEM culture medium, 10% FBS, 1% Pen-strep for another 2 or 24 h. Finally, the mitochondria of HeLa cells were isolated using a mitochondria isolation kit (purchased from Thermofisher) using the procedure provided by the manufacture. TEM was then used to observe the morphology of mitochondria.

The cells treated by D-2 ⊤ FLAG for 2 h and 24 h produce mitochondria surrounded by nanoparticles and nanofibers, respectively (FIGS. 9A-B), while the mitochondria from the HeLa cells incubated with only culture medium exhibit a surface without either nanoparticles or nanofibers. Western blot analysis of the mitochondria isolated from HeLa and U87MG cells showed two ENTK bands (FIG. 10); the major band is the light chain (Lu et al., *J. Mol. Biol.* 292(2):361-373 (1999), which is hereby incorporated by reference in its entirety), indicating the presence of ENTK on mitochondria. Moreover, LC/MS analysis of the isolated mitochondria confirmed that D-2 is the main component of the nanofibers, indicating that D-2 ⊤ FLAG, after reaching mitochondria, is cleaved by ENTK. The in situ formation of nanofibers results in the localization of the nanofibers at mitochondria. To verify whether the proteolysis is necessary for mitochondria targeting, the D-peptide control (D-1 ⊤ flag) was created by connecting D-1 to the D-enantiomer of FLAG tag (flag), which is resistant to ENTK. The fluorescent images of HeLa cells incubated with D-1 ⊤ flag (200 μM, 2 h) failed to exhibit a mitochondria-specific distribution, confirming that the prevention of proteolysis (the conversion to nanofibers) catalyzed by ENTK abolishes the mitochondria targeting.

Discussion of Examples 1-5

The foregoing Examples demonstrate that branched peptides act as a novel type of substrates for enzymatic self-assembly to target mitochondria. Although carrying multiple negative charges, the FLAG-tagged precursors undergo rapid endocytosis and specifically accumulate in mitochondria. The deposition of the nanofibers affect little on the cellular activity, likely due to that the nanofibers impact less than cationic molecules on the membrane potential of mitochondria. The branch architecture is uniquely important for targeting mitochondria since the linear peptide, L-2-FLAG, was shown to be unable to deliver cargo molecule to mitochondria. This work highlights the importance of reactions, in addition to nanoarchitectonics (Komiyama et al., *Bull. Chem. Soc. Jpn.* 90(9):967-1004 (2017), which is hereby incorporated by reference in its entirety), for controlling biological systems. Contrasting to most of the reported mitochondria targeting molecules that usually are lipophilic and cationic (Hopp et al., *Nat. Biotechnol.* 6(10):1204-1210 (1988), which is hereby incorporated by reference in its entirety), this observation illustrates a new mechanism for targeting mitochondria: the integration of enzymatic reaction and self-assembly. As a consequence, the branched peptides of the invention may be able to complement other approaches, e.g., triphenyl phosphonium (TPP) (Zielonka et al., *Chem. Rev.* 117(15):10043-10120 (2017); PCT Application No. PCT/US2018/012359, each of which is hereby incorporated by reference in its entirety). Although the targeting of mitochondria relies on ENTK in this work, the strategy demonstrated here should allow the development of the substrates of other enzymes on mitochondria for mitochondria targeting. Among numerous approaches for mitochondria-specific drug delivery (Yamada et al., *Mitochondrion* 7(1-2):63-71 (2007); Schatz G., *J. Biol. Chem.* 271(50):31763-31766 (1996), which are hereby incorporated by reference in their entirety), the delivery of cargo molecules to target mitochondria by the FLAG-tagged precursors is particularly promising and worth further exploration for potential applications in biomedicine because of the cell compatibility of the FLAG-tagged precursors and the biological importance of mitochondria (Green et al., *Science* 345(6203):1466 (2014), which is hereby incorporated by reference in its entirety).

Example 6—Formation of Hydrogels

400 μL of 2.5% wt Mito-Flag (D-2 ⊤ FLAG) solution was put into a glass vial, followed by the addition of ENTK (final concentration 10U/ml). The vial with Mito-Flag solution was put into a 37° C. water bath, and incubated for 24 h. The images of hydrogel (FIG. 11) were obtained after 24 h incubation. Transmission electron microscope was used to observe the morphology of Mito-Flag solution (200 μM) before and after ENTK addition.

Example 7—Delivery of Plasmids into Mitochondria Using Mito-Flag

Figure 12:
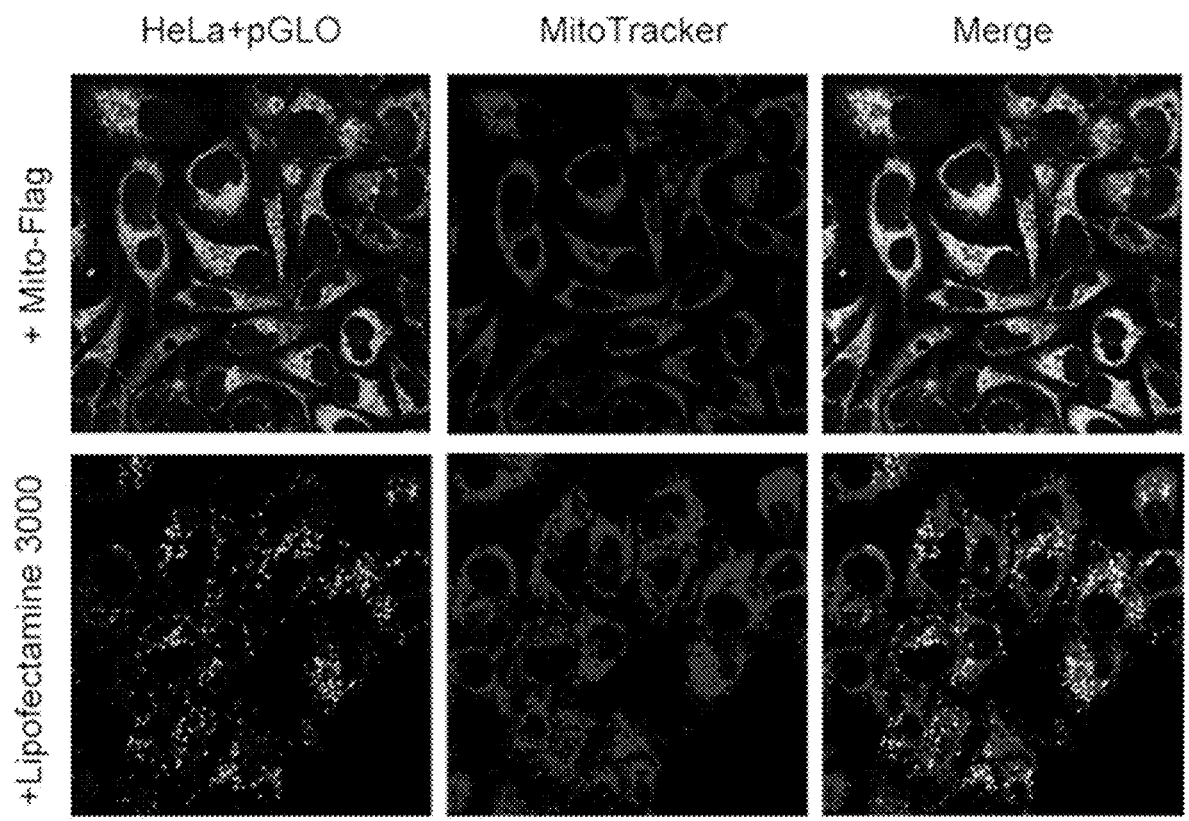
FIG. 12 are fluorescent images of HeLa cells incubated with pGLO plasmid (5 μg/ml) in the presence of Mito-Flag (200 μM) or lipofectamine 3000 for 48 h. The fluorescence from GFP expressed by pGLO plasmid extensively overlap with the fluorescence from MitoTracker®, indicating the delivery of pGLO plasmid into mitochondria.

70% Confluent HeLa cells in experiment groups were incubated with Mito-Flag (D-2 ⊤ FLAG) (200 μM) in the presence of pGLO plasmid (5 μg/mL). Lipofectamine 3000 was used to deliver pGLO plasmid to HeLa cells (70% confluent) in control groups using the procedure provided by manufacture. The cells were incubated in a cell incubator for another 48 h followed by using a Zeiss 880 confocal microscope to observe the intracellular protein expression of pGLO. As shown in FIG. 12, the fluorescence from GFP expressed by the pGLO plasmid extensively overlaps with the fluorescence from MitoTracker®, indicating the delivery of the pGlo plasmid into the mitochondria.

Figure 13:
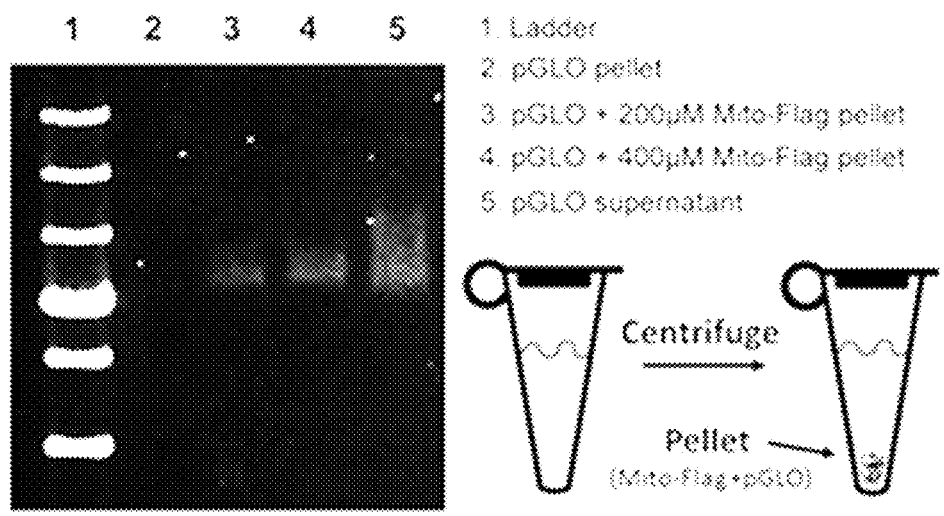
FIG. 13 shows the DNA electrophoresis analysis of pGLO plasmid in the pellet of Mito-Flag (D-2 ᴛ FLAG) after high-speed centrifugation.

DNA electrophoresis analysis of pGLO plasmid in the pellet of Mito-Flag is shown in FIG. 13. 500 μL of 1 μg/mL pGLO was mixed with Mito-Flag at different concentration (0, 200 and 400 μM) in centrifuge tubes. The pGLO plasmids in solutions were then centrifuged down (14000 g, 1.5 h). The pellet at the bottom of centrifuge tubes were collected and dissolved in 10 μL PBS buffer, followed by DNA electrophoresis analysis. 10 μL pGLO solution (1 μg/mL) was used as the positive control.

Figure 14:
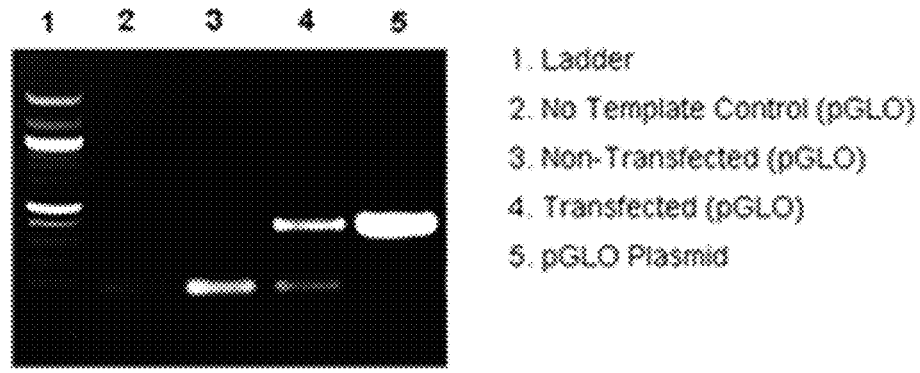
FIG. 14 is an image of the electrophoresis gel used in the detection of pGLO plasmid in the mitochondria isolated from the HeLa cells treated by pGLO (5 μg/ml) and Mito-Flag (D-2 ᴛ FLAG) (200 μM).

The detection of pGLO plasmid from the mitochondria isolated from HeLa cells treated by pGLO and Mito-Flag is shown in FIG. 14. 70% Confluent HeLa cells in experiment groups were incubated with Mito-Flag (200 μM) in the presence of pGLO plasmid (5 μg/mL). The mitochondria were isolated using mitochondria isolation kit (Thermofisher). The isolated mitochondria were then dissolved using a cell lysis buffer. The mitochondria DNA was precipitated by adding ethanol (twice volume) into the previous lysis buffer. The pGLO plasmid in mitochondria was amplified by PCR reaction and detected by DNA electrophoresis.

Example 8—Delivery of Viral Vector into Mitochondria Using Mito-Flag

Figure 15:
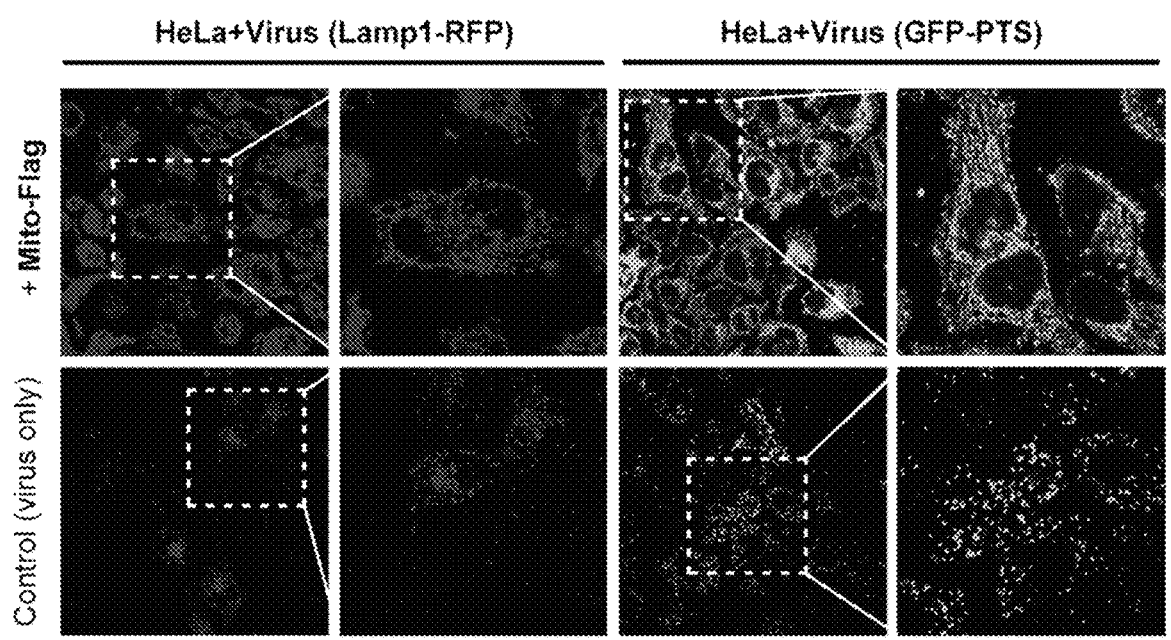
FIG. 15 is a panel of fluorescent images of HeLa cells incubated with baculovirus expressing RFP-Lamp1 (lysosomal associated membrane protein) in the presence of 200 μM Mito-Flag (D-2 ᴛ FLAG) for 24 h

70% Confluent HeLa cells in experiment groups were incubated with Mito-Flag (D-2 ⊤ FLAG) (200 μM) in the presence of baculovirus expressing LAMP1-RFP (lysosomal associated membrane protein) and GFP-PTS. Cells were then incubated in a cell incubator for another 24 h, followed by imaging using a Zeiss 880 confocal microscope to observe the intracellular protein expression. The fluorescent images of HeLa cells incubated with baculovirus expressing RFP-Lamp1 and GFP-PST is shown in FIG. 15.

The mitochondria of the transfected (baculovirus-expressing LAMP1-RFP) HeLa cells were isolated using mitochondria isolation kit (Thermofisher). The HeLa cells were treated with baculovirus expressing RFP-Lamp1 and Mito-Flag (D-2⊤FLAG) (200 μM) for 24 h. The mitochondria were then dissolved using a cell lysis buffer, and the LAMP1-RFP in the mitochondria was detected by western blot.

Figure 16:
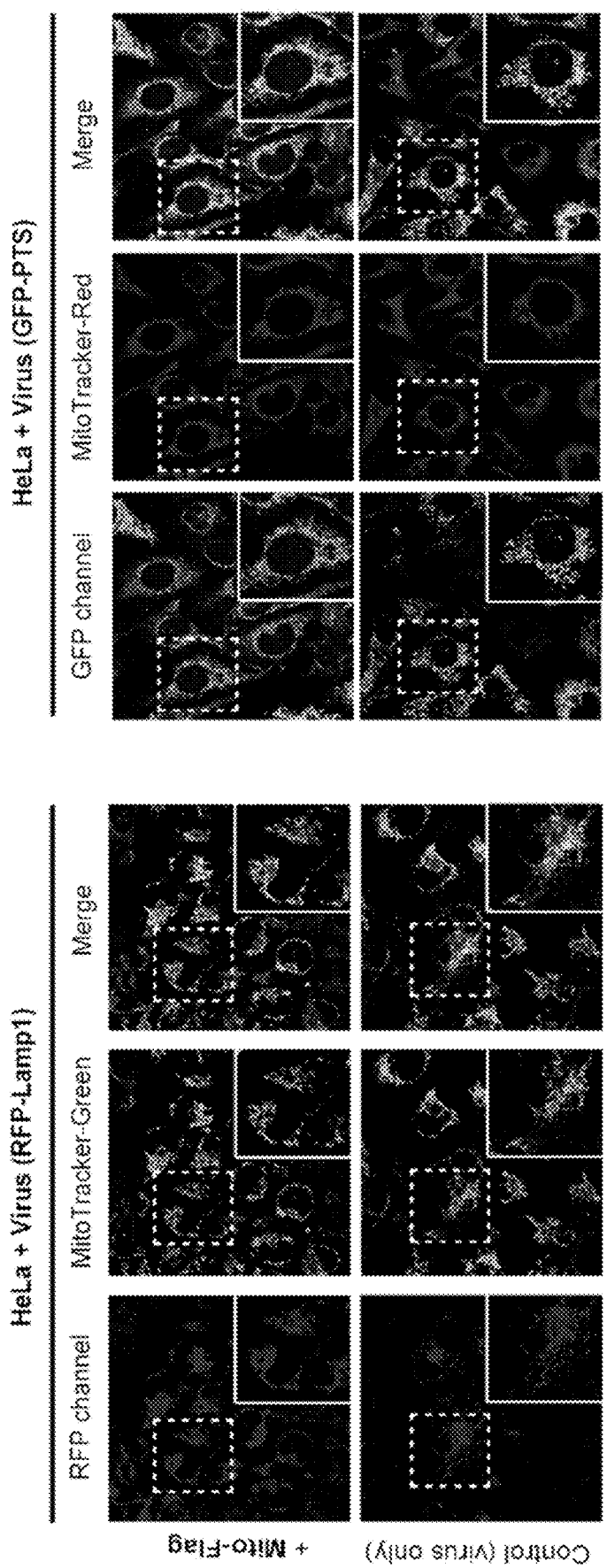
FIG. 16 is a panel of fluorescent images of GFP-Cyt C HeLa and HeLa cells are treated by virus in the presence of 200 μM Mito-Flag (D-2 ᴛ FLAG). The colocalization of RFP-Lamp1 with GFP-Cyt C, and GFP-PTS with MitoTracker confirm that the exogenous fluorescent proteins are expressed in mitochondria.

In further experimentation, 70% Confluent Cyt C-GFP HeLa and normal HeLa cells in experiment groups were incubated with Mito-Flag (D-2⊤FLAG) (200 μM) in the presence of baculovirus expressing LAMP1-RFP and GFP-PTS, respectively. The cells were incubated in a cell incubator for another 24 h followed by using a Zeiss 880 confocal microscope to observe the intracellular protein expression. MitoTracker-DeepRed was used to stain the mitochondria in normal HeLa cells. The colocalization (as seen in FIG. 16) of RFP-Lamp1 with GFP-Cyt C, and GFP-PTS with MitoTracker confirm that the exogenous fluorescent proteins are expressed in mitochondria.

Figure 17:
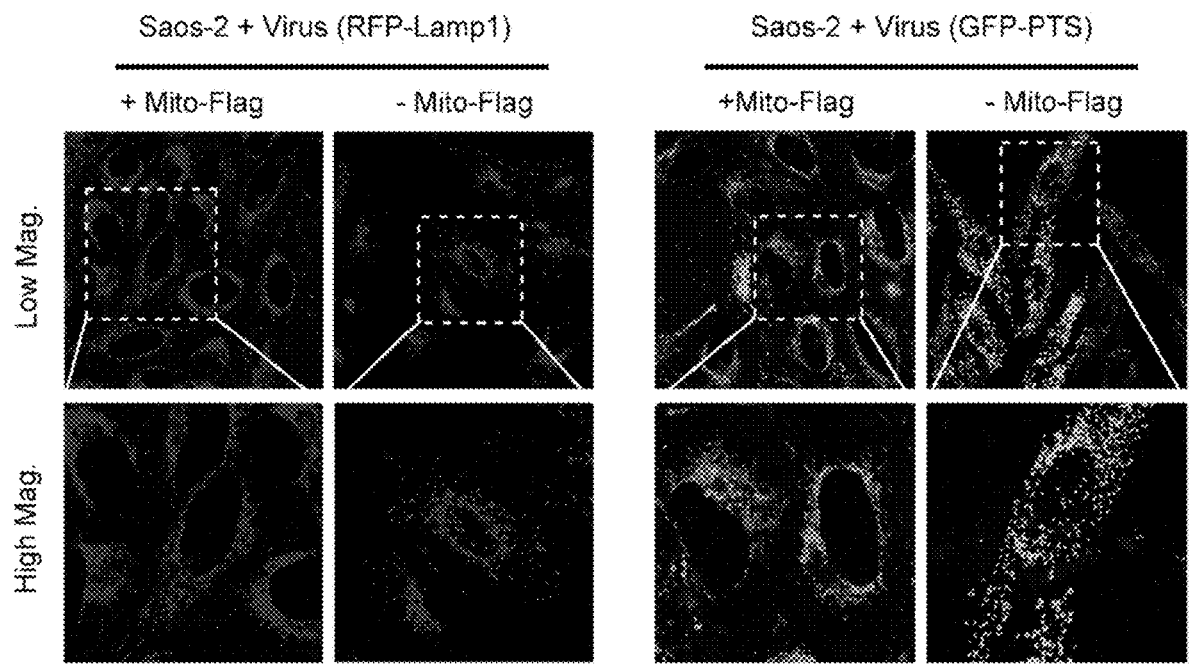
FIG. 17 is a panel of fluorescent images of Saos-2 cells are incubated with virus expressing RFP-Lamp1 and GFP-PTS with 200 μM Mito-Flag (D-2 ᴛ FLAG).
Figure 18:
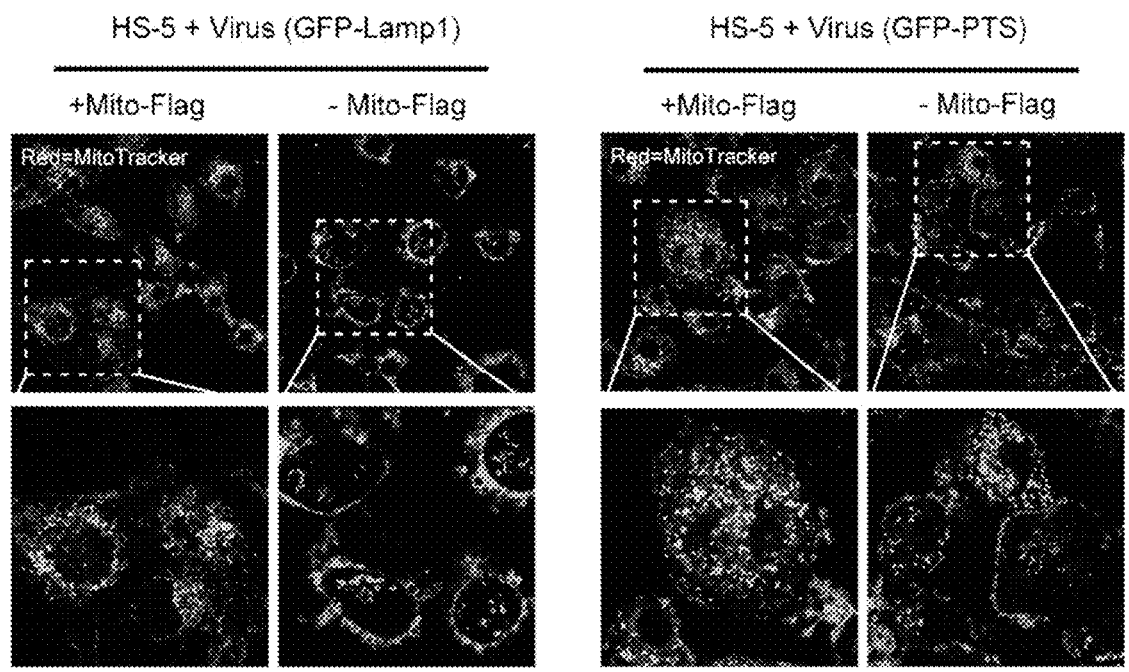
FIG. 18 is a panel of fluorescent images of HS-5 cells are incubated with virus expressing RFP-Lamp1 and GFP-PTS with 200 μM Mito-Flag (D-2 ᴛ FLAG). The absence of fluorescence in the mitochondria of HS-5 indicates a cancer cell-specific transfection.

Additionally, Saos-2, HepG2, and HS-5 cells were also tested under similar conditions. 70% Confluent Saos-2, HepG2, and HS-5 cells in experiment groups were incubated with Mito-Flag (D-2⊤FLAG) (200 μM) in the presence of baculovirus expressing LAMP1-RFP and GFP-PTS. Cells were incubated in a cell incubator for another 24 h followed by using a Zeiss 880 confocal microscope to observe the intracellular protein expression. Image of the Saos-2 Cells are displayed in FIG. 17, and the images of the HS-5 cells are displayed in FIG. 18. The Mitochondria in HS-5 were stained with MitoTracker®-DeepRed (Thermofischer).

Example 9—Gene Transfection with Mito-Flag

In order to test gene transfection, HeLa cells were grouped and treated with two processes. Group ①: 70% confluence HeLa cells were incubated with 200 μM Mito-Flag and baculovirus expressing LAMP1-RFP or GFP-PTS in MEM medium. After 24 h, old medium was removed, and cells were washed with PBS buffer 3 times. Then, HeLa cells were incubated with fresh MEM medium for another 24 h before imaging.

Figure 19:
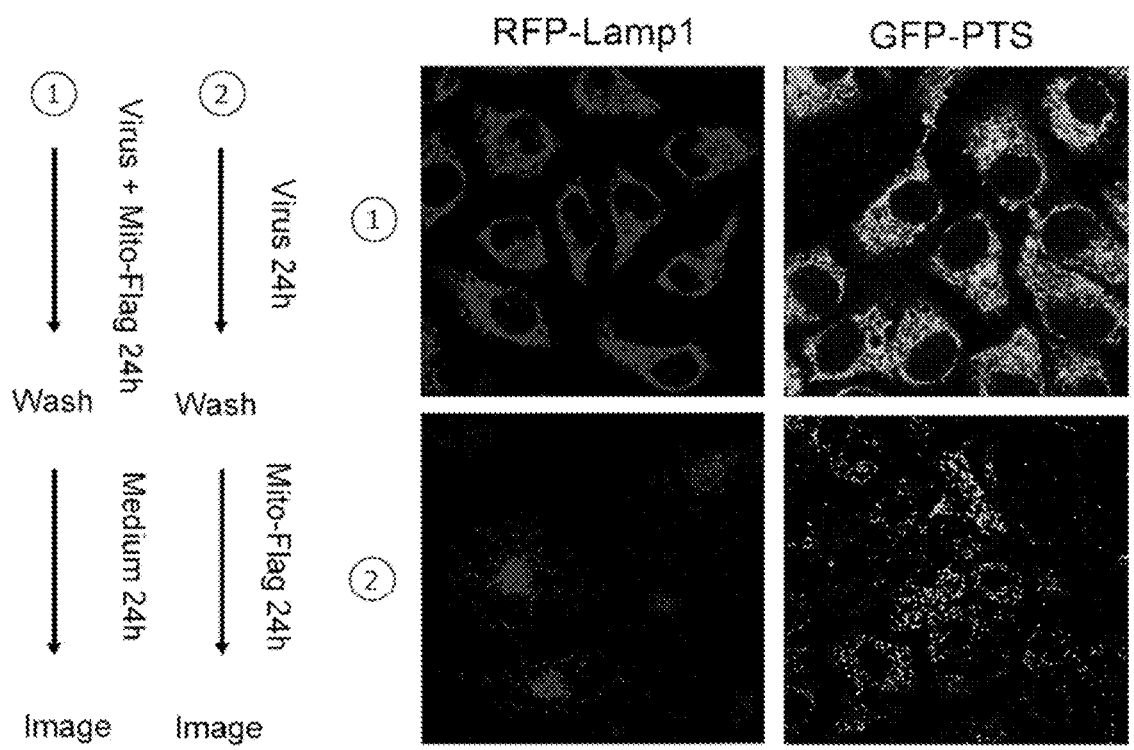
FIG. 19 is a panel of fluorescent images of HeLa cells treated by processes ①　and ②. Results indicate that the localizations of Lamp1 and GFP-PTS in mitochondria mostly originate from gene transfection.

Group ②. 70% confluence HeLa cells were incubated with baculovirus expressing LAMP1-RFP or GFP-PTS in MEM medium. After 24 h, old medium was removed, and cells were washed with PBS buffer 3 times. Then, HeLa cells were incubated with fresh MEM medium including 200 μM Mito-Flag for another 24 h before imaging. The results indicate the localization of the LAMP1-RFP and GFP-PTS in the mitochondria (displayed in FIG. 19) mostly originate from gene transfection.

Figure 20:
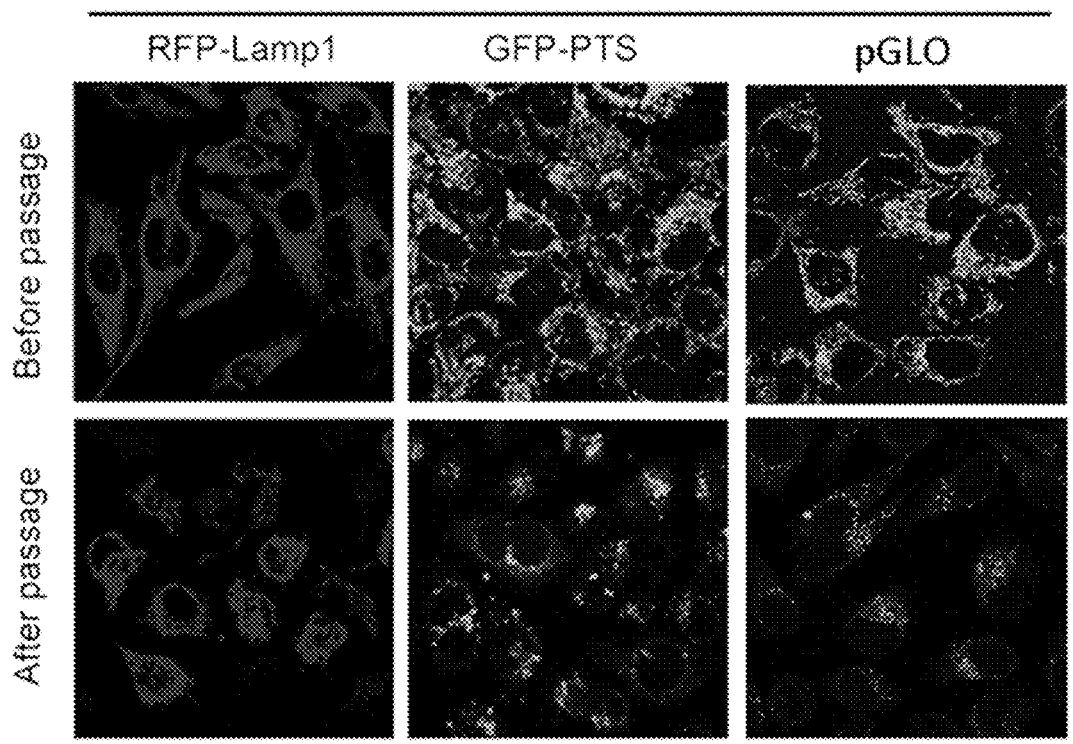
FIG. 20 is a panel of fluorescent images of gene transfected HeLa cells before and after cell passage.

Further, gene transfected HeLa cells were images before and after cell passage, as shown in FIG. 20. To accomplish this, 70% confluence HeLa cells were incubated with 200 μM Mito-Flag in the present of pGLO plasmid (5 μg/mL) or baculovirus expressing LAMP1-RFP or GFP-PTS in MEM medium. After 24 h, cells were passaged and 50% of them were seeded back to new confocal dishes. HeLa cells in new dished were incubated with fresh MEM medium for another 24 hours before imaging. Cells were imaged by Zeiss 880 confocal microscope.

Discussion of Examples 6-9

Cell selective gene expression at mitochondria holds great potentials for treating mitochondrial diseases. But current approaches, including mitochondria transfer, still suffer serious limitations. The preceding Examples 6-9 show that enzymatic morphology/phase transition of isopeptides effectively translocates gene expression to mitochondria in a cell selective manner. Consisting of DYKDDDDK (SEQ ID NO:35) as the branch and phenylalanine rich short peptides as the backbone, the isopeptides form micelles, which, upon the cleavage of the Flag catalyzed by enterokinase, turn into a gel made of nanofibers. The mitochondrial enterokinase cleaves the Flag of the isopeptides, thus turning the micelles to nanofibers on the mitochondria. Mixing the Mito-Flags and a DNA plasmid encoding GFP or baculovirus vectors carrying the genes of proteins translocates the gene expression to mitochondria, evidenced by the exclusive expression of those non-mitochondrial proteins at mitochondria. Using local enzymatic reaction to omit or override signal peptides for mitochondria-targeted gene expression, this work provides a new way to target organelles and may offer a new perspective to understanding cell specific endogenous trafficking.

Most of the reported mitochondria targeting molecules are lipophilic and cationic, which may become cytotoxic with accumulation. The preceding Examples show enzymatic cleavage of branched peptides that carry negative charges for targeting mitochondria. Conjugating a well-established protein tag (i.e., FLAG-tag) to self-assembling motifs affords the precursors that form micelles. Enzymatic cleavage of the hydrophilic FLAG motif (DDDDK) (SEQ ID NO: 17) by enterokinase (ENTK) turns the micelles to nanofibers. After being taken up by cells, the micelles, upon the action of intracellular ENTK, turns into nanofibers to locate mainly at mitochondria. The micelles of the precursors are able to deliver cargos (either small molecules or proteins) into cells, largely to mitochondria and within two hours. Preventing ENTK proteolysis diminishes mitochondria targeting. As the first report of using enzymatic self-assembly for targeting mitochondria and delivery cargos to mitochondria, this work illustrates a fundamentally new way to target subcellular organelles for biomedicine.

Example 10—Prospective Treatment of Uterine Cancer Xenograft Using Dox in Combination with Mito-Flag MES-SA/Dx5 cells are an established model cell-line (human uterine sarcoma) for evaluating the efficacy and toxicity of new drugs in vivo.

Fifteen nude mice will be used for experiments to define the tumor growth curve. $1 \times 10^7$ MES-SA/Dx5 cells will be implanted into the mice via intraperitoneal injection using a 25 G needle. Five of the tumor-bearing mice will be used to define the tumor growth curve with control treatment, five mice will be given DOX (only), and five mice will be given a mixture of DOX/D-2⊤FLAG. The mice will be injected subcutaneously and peritumorally (6 times, every 3 days starting at Day 1) with either 100 μL of D-2⊤FLAG at 4 μg/μL (400 μg dose or 40 mg/kg) with 5 mg/kg DOX in PBS buffer (experimental), or 5 mg/kg DOX in 100 μL PBS buffer (experimental), or 100 μL, of PBS buffer (control). Tumor volume measurements will be made every three days, also starting on Day 1. Volume of tumors will be measured by caliper.

Materials and Methods for Examples 11-19

Cell Culture: HeLa, HepG2, Saos-2, and HS-5 cells were purchased from American Type Culture Collection (ATCC). HEK293 cells were provided by Prof. Chris Miller from Brandeis University. All the cell lines used in these Examples authenticated by CellCheck 9—human (9 Marker STR Profile and Inter-species Contamination Test, IDEXX), confirming 100% match of the cell identity. HeLa, HepG2, and HEK293 cells were cultured in Minimum Essential Medium (MEM) supplemented with 10% (vol/vol) FBS, 0.5% (vol/vol) penicillin (10, 000 unit), and 0.5% (vol/vol) streptomycin (10, 000 unit). Saos-2 cells were cultured in McCoy's 5A with l-glutamine supplemented with 15% (vol/vol) FBS, 10% (vol/vol) FBS, 0.5% (vol/vol) penicillin (10, 000 unit), and 0.5% (vol/vol) streptomycin (10, 000 unit). HS-5 cells were cultured in Dulbecco's Modified Eagle Medium (DMEM) supplemented with 10% (vol/vol) FBS, 0.5% (vol/vol) penicillin (10, 000 unit), and 0.5% (vol/vol) streptomycin (10, 000 unit). All cells were maintained at 37° C. in a 5% $CO_2$ incubator.

Plasmid Import: For Mito-Flag-assisted delivery of plasmids (pGLO (Bassiri, "pGLO Mutagenesis: A Laboratory Procedure in Molecular Biology for Biology Students," *Biochem. Mol. Bio. Edu.* 39:432-439 (2011), which is hereby incorporated by reference in its entirety) (Bio-Rad), Mito-pGLO (Ordered from Invitrogen, the final construct was verified by sequencing), pMAX-DEST (Addgene, CAT #: 37631), FUNDC1-Myc (OriGene, CAT #: RC208211) and GFP-TP53 (Addgene, CAT #12091)), the plasmids were dissolved in culture medium (with 10% FBS) followed by the addition of Mito-Flag. The mixtures were incubated in room temperature for 20 min before adding to cells (already adhered). Lipofectamine 3000 (Invitrogen) was used for the general transfection of plasmids following the manufacture's instruction. Arabinose (0.2 wt %) was added in the delivery of pGLO and Mito-pGLO. Cells were incubated at 37° C. in a 5% $CO_2$ incubator before further analysis. Unless specifically mentioned, the final concentration of Mito-Flag was 200 µM. The dose of plasmids was 5 µg per 80, 000 cells. Recommended concentration of plasmid (in medium) is 5 µg/mL. The incubation time was 48 h.

Virus Import: For Mito-Flag-assisted delivery of viral vectors including baculovirus (Thermo Fisher Scientific, CAT #C10604 and CAT #C10597), AAV (Addgene, CAT #: 37825-AAV5), and lentivirus (abm, CAT #LVP691)), the viruses were mixed in culture medium (with 10% FBS) followed by the addition of Mito-Flag. See Goo et al., "Activity-Dependent Trafficking of Lysosomes in Dendrites and Dendritic Spines," *J. Cell Bio.* 216:2499-2513 (2017); Nilsen et al., "Peroxisomal Targeting as a Tool for Assaying Protein-Protein Interactions in the Living Cell Cytokine-Independent Survival Kinase (cisk) Binds pdk-1 in vivo in a Phosphorylation-Dependent Manner," *J. Bio. Chem.* 279: 4794-4801 (2004), each of which is hereby incorporated by reference in its entirety. The mixtures were incubated in room temperature for 20 min before adding to cells (already adhered). Following the manufacture's protocol, cells were directly incubated with virus in culture medium for the general transfection. Cells were incubated at 37° C. in a 5% $CO_2$ incubator before further analysis. Unless specifically mentioned, the final concentration of Mito-Flag was 200 µM.

Immunofluorescence: Cells were plated on confocal dishes (CellVis), fixed in 4 wt % paraformaldehyde for 15 min, and permeabilized with 1% BSA and 0.1% Tween 20. Fixed cells were incubated in primary antibody at 4° C. overnight, washed three times for 5 min each, incubated in secondary antibody for 1 h, and washed three times for 5 min each.

Confocal Microscopy: 80, 000 cells were seeded in 32 mm confocal dishes (CellVis) and incubated in cell incubator at standard condition for 24 h for adherence. After being treated by the condition of interest, cells were analyzed by ZEISS LSM 880 Confocal Microscope and images were taken.

Intracellular Fluorescence Quantification: Cells were seeded in petri dishes and incubated in standard condition for 12 h before experiment. After being treated by the condition of interest, all cells were washed by PBS (3 time for 5 min). After the washing step, cells were detached from the dishes using trypsin. The trypsin was removed by centrifuge and washing with PBS. The cell suspensions (in PBS) were diluted to $10^5$ cell/mL. 100 µL diluted cell suspension was added in a 96-well plate (at least 5 wells per sample). The intracellular fluorescence intensity was immediately determined using a DTX 880 Multimode Detector (Beckman Coulter Inc.). The experiments were repeated, and the intracellular fluorescence intensity was averaged (n>3).

Mitochondrial Isolation: Mitochondria were isolated from cells treated by conditions of interest using mitochondria isolation kit (Thermo Fisher Scientific, CAT #89874) following the manufacture's instruction. The mitochondrial DNA was extracted by Mitochondrial DNA Isolation Kit (Abcam, CAT #ab65321) following the manufacture's protocol.

Western Blots of Mitochondrial Proteins: Mitochondria were isolated from cells treated by conditions of interest using mitochondria isolation kit (Thermo Fisher Scientific). Total mitochondrial protein extracts were prepared in lysis buffer (Cell Signaling Technology, with 1× protease inhibitor cocktail (Abcam)) followed by 5 freeze-thaw circles and 30 min sonication. Protein concentration was determined by Coomassie Blue method. Protein extracts (20 µg per lane) were separated by SDS-PAGE and transferred to polyvinylidene difluoride (PVDF) membranes. Western blotting was performed according to standard protocols. Gel analysis was conducted using ImageJ. All antibodies were purchased from Abcam.

Enterokinase Gene Knockdown: For each transfection, siRNA duplex (Santa Cruz Biotechnology, cat. No. Sc-72233) was diluted into 100 µL antibiotic-free and FBS-free siRNA transfection medium (Santa Cruz Biotechnology, sc-36868). Recommended final siRNA concentration is 0.1 µM. For each transfection, 6 µL of siRNA transfection reagent (Santa Cruz Biotechnology, sc-29528) was diluted into 100 µL siRNA transfection medium. The siRNA duplex solution was mixed directly into the dilute transfection reagent using a pipette. The mixture was incubated at room temperature for 30 minutes. 0.8 mL siRNA transfection medium was added into the 0.2 mL mixture of siRNA and transfection reagent (total volume 1 mL). Cells (80, 000 per transfection, already adhered) were washed once with 2 mL of siRNA transfection medium and incubated with the 1 mL mixture of siRNA and transfection reagent for 8 h at 37° C. in a $CO_2$ incubator. 1 mL of normal growth medium containing 2 times FBS and antibiotics concentration was added to the cells without removing the transfection mixture. The cells incubated for an additional 24 hours followed by aspirating the medium and replacing with fresh 1× normal growth medium. Cells were incubated for another 48 h before further assay.

mtDNA Depletion and the Imaging of Mitochondrial DNA: Cells were incubated with 1 µM ethidium bromide for 24 h or longer time for mtDNA depletion. PicoGreen was used to check the depletion of mtDNA (Ashley et al., "Detection of Mitochondrial DNA Depletion in Living Human Cells Using PicoGreen Staining," *Exp. Cell Res.* 303:432-446 (2005), which is hereby incorporated by reference in its entirety). After that, cells were washed by PBS 3 times for 5 min. After the washing step, the mtDNA depleted cells were incubated with culture medium in the presence of free pMAX-DEST (Addgene), the mixture of Mito-Flag and pMAX-DEST, or the mixture of lipofectamine and pMAX-DEST for another 24 h. The mtDNA depleted cells incubated with only culture medium were used as mtDNA-negative control. Cells were then washed by PBS 3 times for 5 min, and then stained by PicoGreen (in culture medium) for 2 h before further analysis.

PCR Experiment: The MT-CO1 gene was amplified by Phusion DNA polymerase (New England Biolabs, CAT #M0530) via the following primers:

```
forward:
                            SEQ ID NO: 77
TAAGCACCCTAATCAACTGGC,;
and reverse:
                            SEQ ID NO: 78
GCCTCCACTATAGCAGATGCG,.
```

This was carried out according to the manufacture's protocol. The products were examined by DNA electrophoresis.

DNA Encapsulation Efficiency: To prove that plasmids are associated with Mito-Flag, free pGLO plasmid (2 µg/mL) and the mixture of Mito-Flag (200 µM) and pGLO plasmid (2 µg/mL) was centrifuged by an Eppendorf 5430 R centrifuge (14, 000 rpm, 1 h). Supernatant was transferred to new centrifuge tubes and the pellets were resuspended in 20 µL TBE buffer. The presence of pGLO plasmid in pellets was determined by DNA electrophoresis. All samples (20 µL per well) for DNA electrophoresis were loaded in 1 wt % agarose. The gel was run at 120 V for 1.5 h. Ethidium Bromide was used for DNA staining in gel. The amount of pGLO plasmid in the supernatant was quantified by PicoGreen assay (Ahn et al., "PicoGreen Quantitation of DNA: Effective Evaluation of Samples Pre- or Post PCR," *Nucleic Acids Res.* 24:2623-2625 (1996), which is hereby incorporated by reference in its entirety). Encapsulation efficiency (EE) % was calculated as: % EE=[(DNA added–Free unentrapped DNA)/DNA added]×100%

Example 11—Delivery of Nucleic Acids into Mitochondria

As shown in FIG. 21B, the nanofibers on mitochondria should increase the local viscosity, arrest the DNA cargos near the mitochondria, and promote the mitochondria-targeted gene delivery. This mechanism is supported by the import of FITC-labeled oligonucleotides and a plasmid backbone, pMAX-DEST (Klezovitch et al., "A Causal Role for ERG in Neoplastic Transformation of Prostate Epithelium," *Proc. Nat. Acad. Sci.* 105:2105-2110 (2008), which is hereby incorporated by reference in its entirety), into mitochondria. When incubated with FITC-labeled oligonucleotides and Mito-Flag, HeLa cells display green fluorescence mainly in mitochondria (FIG. 22A), but only scattering fluorescent dots in the cytosol in the absence of Mito-Flag. Ethidium bromide (EB) (Yu et al., "Depletion of Mitochondrial DNA by Ethidium Bromide Treatment Inhibits the Proliferation and Tumorigenesis of T47D Human Breast Cancer Cells," *Toxicol. Lett.* 170:83-93 (2007), which is hereby incorporated by reference in its entirety) was used to generate the mtDNA depleted ($\rho^0$) cells. PicoGreen (Yu et al., "Depletion of Mitochondrial DNA by Ethidium Bromide Treatment Inhibits the Proliferation and Tumorigenesis of T47D Human Breast Cancer Cells," *Toxicol. Lett.* 170:83-93 (2007), which is hereby incorporated by reference in its entirety), a fluorescent dye for DNA detection, confirms that EB effectively removes mtDNA. The $\rho^0$ cells incubated with the mixture of Mito-Flag and pMAX-DEST (20 µg/mL) show multiple green fluorescent spots overlapping with MitoTracker (FIG. 22B), validating that Mito-Flag delivers DNA into mitochondria. Incubating the $\rho^0$ cells with the plasmid alone or plasmids mixed by lipofectamine hardly regain the DNA in mitochondria (FIG. 22B). Imaging analysis of the mitochondria regions indicates that 89% in average of mitochondria contain DNA (stained by PicoGreen) after treating the $\rho^0$ cells with the pMAX plasmid and Mito-Flag. This ratio is close to that of normal HeLa cells (98%). This result further supports that Mito-Flag acts as a substrate for perimitochondrial ENS to deliver DNA into the mitochondria.

Example 12—CRISPR/Cas9 for Knocking Out MT-CO1 in the mtDNA

Since the mitochondrially encoded proteins, such as mitochondrial cytochrome c oxidase subunit I (MT-CO1), are critical for oxidative phosphorylation (OXPHOS), knocking out the proteins would disrupt mitochondrial energetics, reduce ATP supply, and dysfunction efflux pumps which are essential for drug resistance in cancer. This assumption is supported by the Mito-Flag facilitated delivery of LentiCRISPRV2 plasmid encoding CRISPR/Cas9 and the gRNA of MT-CO1 (SEQ ID NOS: 79 and 80) (termed CRISPR-MT-CO1) into mitochondria:

```
forward:
                            SEQ ID NO: 79
5'-CACCGGGCCCAGCTCGGCTCGAATA,;
and reverse:
                            SEQ ID NO: 80
5'-AAACTATTCGAGCCGAGCTGGGCCC,.
```

To confirm the delivery and gene expression in mitochondria, HeLa cells were incubated with the mixture of Mito-Flag and CRISPR-MT-CO1-mCherry plasmid, which encodes mCherry as the indicator of gene expression, in addition to CRISPR/Cas9 and the gRNA of MT-CO1. As shown in FIG. 23A, intensive fluorescence from mCherry presents in the mitochondria of HeLa cells incubated with Mito-Flag and CRISPR-MT-CO1-mCherry plasmid, validating the mitochondria-targeted gene delivery via Mito-Flag perimitochondrial ENS and the gene expression in mitochondria.

To examine the efficiency of mitochondria genetic engineering through CRISPR/Cas9, the protein level of MT-CO1 was evaluated in cells. Western blot and immunofluorescence staining analysis revealed a significantly reduced MT-CO1 level in the HeLa cells incubated with the mixture of Mito-Flag and CRISPR-MT-CO1 plasmid ($3^{rd}$ day), compared to those treated by solvent control (PBS), free plasmid or Mito-Flag alone (FIG. 23B). Moreover, PCR experiments (start with equal dosage of whole cell DNA) using the primers flanking the targeted cleavage site generate drastically decreased product from the HeLa cells undergo the incubation with Mito-Flag and CRISPR-MT-CO1 plasmid ($3^{rd}$ day, FIG. 23C). However, the PCR products from the cells treated by PBS, plain plasmid, or Mito-Flag are mostly identical (FIG. 23C). Replacing the gRNA in CRISPR-MT- CO1 plasmid by random gRNA (SEQ ID NOs: 81 and 82) hardly results in the KO of MT-CO1:

```
forward:
                            SEQ ID NO: 81
5'-CACCGCCAGAGAAGAAGACTACTGA,;
and reverse:
                            SEQ ID NO: 82
5'-AAACTCAGTAGTCTTCTTCTCTGGC,.
```

These results indicate that the Mito-Flag perimitochondrial ENS delivers the CRISPR-MT-CO1 plasmid into the mitochondria of HeLa cells where the Cas9 protein and gRNA are made. The CRISPR/Cas9 complex in mitochondria cleaves the target gene, leading to the knockout (KO) of MT-CO1.

Because MT-CO1 plays a critical role in OXPHOS, the KO of MT-CO1 in HeLa cell results in deficient synthesis of ATP (visualized by an ATP probe, FIG. 23D) in the mitochondria. The ATP insufficiency decreases the efficiency of the ATP-dependent drug efflux pumps and multidrug resistance (MDR) in cancer cell (FIG. 23E). Since the MDR is a major factor in the failure of many forms of chemotherapy, the MT-CO1-KO cancer cells, being MDR ineffective, become more sensitive to chemotherapeutic agents, such cisplatin, than the wild type (WT, FIG. 23F). Moreover, because the maintenance of mitochondrial membrane potential largely relies on cytochrome c oxidase (Pacelli et al., "Tight Control of Mitochondrial Membrane Potential by Cytochrome C Oxidase," *Mitochondrion* 11:334-341 (2011), which is hereby incorporated by reference in its entirety), the deletion of the subunit I in this protein also generates less polarized mitochondria in cell (FIG. 23G). These results confirm that CRISPR/Cas9-mediated knockout of any critical mitochondrial genes is a viable approach for sensitizing cancer cells to traditional chemotherapy.

Example 13—Mitochondrial Transgene Expression of FUNDC1 to Induce Mitophagy

Because the overexpression of FUNDC1 in mitochondria results in mitophagy (Liu et al., "Mitochondrial Outer-Membrane Protein FUNDC1 Mediates Hypoxia-Induced Mitophagy In Mammalian Cells," *Nat. Cell Biol.* 14:177-185 (2012), which is hereby incorporated by reference in its entirety), HeLa cells were incubated with a mixture of Mito-Flag and the plasmids encoding Myc-tagged FUNDC1 protein (FUNDC1-Myc) (Liu et al., "Mitochondrial Outer-Membrane Protein FUNDC1 Mediates Hypoxia-Induced Mitophagy In Mammalian Cells," *Nat. Cell Biol.* 14:177-185 (2012), which is hereby incorporated by reference in its entirety), in mitochondria for inducing mitophagy.

Western blot experiments reveal that the HeLa cells incubated with the mixture of Mito-Flag (200 μM) and FUNDC1 plasmid (5 μg/mL, 3 days) exhibit higher FUNDC1 and LC3B (a marker protein for autophagosome) levels in the mitochondrial and cytosolic fraction, respectively (FIG. 24A), when compared to the controls. This indicates the gene expression of FUNDC1 plasmid in mitochondria and the initiation of mitophagy in the cells. Fluorescent microscopy reveals elongated mitochondria in HeLa cells treated by Mito-Flag only, but globular mitochondria in the cells incubated with the mixture of Mito-Flag and FUNDC1-Myc plasmids (FIG. 24B), which indicates the engulfment of mitochondria by autophagosomes (Gomes et al., "Mitochondrial Morphology in Mitophagy and Macroautophagy," *Biochim. Biophys. Acta., Mol. Cell Res* 1833: 205-212 (2013), which is hereby incorporated by reference in its entirety). Immunochemical staining of LC3B in FUNDC1 plasmid-transfected HeLa cells (via Mito-Flag perimitochondrial ENS) clearly shows the redistribution of nucleus-pool LC3 to cytoplasm (Huang et al., "Identifying an Essential Role of Nuclear LC3 for Autophagy," *Autophagy* 11:852-853 (2015), which is hereby incorporated by reference in its entirety) and the co-localization with mitochondria (FIG. 24C, indicated by arrows), confirming mitophagy. Given that FUNDC1 associates with LC3 on the mitochondrial outer membrane (MOM) for mitophagy, these results also indicate that the FUNDC1-Myc protein, although produced in mitochondrial matrix, can move outside the mitochondria via protein export (Poyton et al., "Protein Export from the Mitochondrial Matrix," *Trends Cell Bio.* 2:369-375 (1992), which is hereby incorporated by reference in its entirety) to MOM where it interacts with LC3. Little co-localization between LC3 and mitochondria presents in the control HeLa cells (FIG. 24C).

Example 14—Mitochondrial Transgene Expression of p53 to Induce Apoptosis

Tumor suppressor p53 is a protein that directly participates in the intrinsic apoptosis pathway by inducing mitochondrial outer membrane permeabilization. In this Example, HeLa cells were transfected the plasmid encoding GFP-tagged p53 (GFP-TP53) (Boyd et al., "An Intact HDM2 RING-Finger Doman is Required for Nuclear Exclusion of p53," *Nat. Cell Biol.* 2:563-568 (2000), which is hereby incorporated by reference in its entirety) into mitochondria for imaging mitochondrial p53 and direct apoptosis initiation.

HeLa cells incubated with the mixture of GFP-TP53 plasmid and Mito-Flag (24 h) exhibit bright green fluorescence in mitochondria (FIG. 24D), indicating the import of GFP-TP53 plasmid and the generation of p53 protein in mitochondria. In contrast, HeLa cells treated by free plasmid show sporadic puncta in cytosol with no colocalization with mitochondria (FIG. 24D). Generally, HeLa cells escape from p53-induced apoptosis via E6 protein-mediated p53 degradation (Węsierska-Gądek et al., "Escape of p53 Protein from E6-mediated Degradation in HeLa Cells After Cisplatin Therapy," *Int. J. Cancer* 101:128-136 (2002), which is hereby incorporated by reference in its entirety). After the mitochondrial transfection of GFP-TP53 plasmid, the viability of HeLa cells reduces significantly (FIG. 24E), which agrees with the apoptosis analysis via propidium iodide (PI, FIG. 24F) and confirms the p53-induced apoptosis. Incubating free GFP-TP53 plasmid or Mito-Flag with HeLa cells hardly causes cell death (FIGS. 24E-24F). Western blot analysis shows more cytosolic cytochrome c (cyt c) in the transfected HeLa cells (by Mito-Flag, $3^{rd}$ day) than those in the control cells. These results agree with the p53-induced mitochondrial permeabilization and cyt c release in the intrinsic apoptosis pathway (Haupt et al., "Apoptosis—The p53 Network," *J. Cell Sci.* 116:4077-4085 (2003), which is hereby incorporated by reference in its entirety).

The perimitochondrial ENS of Mito-Flag also delivers GFP-TP53 plasmid into the mitochondria of Saos-2 cell, another TP53-null cancer cell line, which induces significant cell death (FIG. 24E), although free GFP-TP53 plasmid and Mito-Flag are innoxious (FIG. 24E). Since the association of p53 with the proteins from bcl-2 family at MOM is essential for triggering mitochondrial permeabilization, again, the cell death indicates that the mitochondrially encoded p53 may move out, via protein export (Poyton et al., "Protein Export from the Mitochondrial Matrix," *Trends Cell Bio.* 2:369-375 (1992), which is hereby incorporated by reference in its entirety) to MOM. On the contrary, neither free GFP-TP53 plasmid nor the mixture of Mito-Flag and GFP-TP53 plasmid impairs the viability of HS-5 cells (FIGS. 24E, 24G), which agrees with the observed specificity of Mito-Flag perimitochondrial ENS for cancer cells (FIGS. 25 and 26).

Example 15—Perimitochondrial ENS Combining with Viral Vectors for Mitochondrial Transgene Expression Mito-Flag was used to pack baculovirus vectors, because liposomes enhance transfection of viral vectors (Fraley et al., "Introduction of Liposome-Encapsulated SV40 DNA into Cells," *J. Biol. Chem.* 255:10431-10435 (1980), which is hereby incorporated by reference in its entirety). While the TEM of the solution of baculovirus shows rod-like viruses (FIG. 25A), the TEM of the mixture reveals that the micelles made of Mito-Flag adhere on the viruses, generating clusters of Mito-Flag-coated virus (FIG. 25B). Upon the addition of the enzyme, ENTK, the Mito-Flag-virus clusters break into uncoated viruses entangled by nanofibers of 6±1 nm (FIG. 25B).

Being incubated with the baculovirus encoding RFP-LAMP1 or GFP-PTS, the HeLa cells display fluorescence only in the intended organelles, that is, lysosome or peroxisome, respectively (FIG. 25C). However, the transfection with Mito-Flag perimitochondrial ENS results in the fluorescence of RFP-LAMP1 or GFP-PTS largely overlaps with the fluorescence from MitoTracker (FIG. 25D), though some fluorescence appears in the cytosol, likely due to the baculovirus without encapsulation by Mito-Flag or protein export from mitochondria (Poyton et al., "Protein Export from the Mitochondrial Matrix," *Trends Cell Bio.* 2:369-375 (1992), which is hereby incorporated by reference in its entirety). Moreover, Mito-Flag results in more cells that express RFP-LAMP1 or GFP-PTS compared to the control (free baculoviral vectors), indicating efficient transfection was achieved with Mito-Flag perimitochondrial ENS. Western blot analysis of the proteins in the isolated mitochondria (FIG. 25E) confirms that the mitochondrial expression of RFP-LAMP1 occurs only when the baculoviral vectors plus Mito-Flag are taken up by the cells and result in perimitochondrial ENS.

Both the fluorescence of GFP-PTS or RFP-LAMP1 in mitochondria of the HeLa cells decreases after subculture (FIG. 25F), with more significant reduction for GFP-PTS, indicating the dilution of the baculoviral DNAs in mitochondria during cell proliferation, and a higher proteolytic resistance for RFP-LAMP1 than GFP-PTS against mitochondrial proteases. Cells were treated using two different procedures: (1) concurrent incubation; and (2) sequential incubation. As shown in FIG. 25G, while the concurrent incubation achieves gene expression in mitochondria, the sequential incubation results in the localization of GFP-PTS and RFP-LAMP1 merely in their intended organelles. These results eliminate the possibility that the non-mitochondrial proteins observed in mitochondria originate from the Mito-Flag-induced protein redistribution to mitochondria after normal gene expression (in cytosol or ER) (He et al., "Enzyme-Instructed Assemblies Enable Mitochondria Localization of Histone H2B in Cancer Cells," *Angew. Chem. Int.* (2020), which is hereby incorporated by reference in its entirety).

Moreover, rifampicin (80 µg/mL), a mitochondrial RNA polymerase inhibitor (Gadaleta et al., "The Effect of Rifampicin on Mitochondrial RNA Polymerase From Rat Liver," *FEBS Lett.* 10:54-56 (1970), which is hereby incorporated by reference in its entirety), significantly weakens the mitochondrial fluorescence of HeLa cells treated by Mito-Flag mixed with baculovirus (RFP-LAMP1) or pGLO plasmid (FIG. 25H), but hardly affects the cell viability and protein expression in cells undergo conventional transfection, confirming that the genes delivered by perimitochondrial ENS undergo transcription in mitochondria.

Besides baculoviral vectors, the combination of Mito-Flag with adeno-associated virus (AAV) or lentivirus (LTV) encoding GFP or RFP, respectively, also results in mitochondrial specific gene expression. Without the addition of Mito-Flag, the expressed GFP diffuses in entire cells. These results indicate that the Mito-Flag perimitochondrial ENS is suitable to enhance delivery of a wide variety of frequently used viral vectors for mitochondria-targeting transfection.

Example 16—Mitochondrial Transgene Expression in a Cancer Cell-Specific Manner

Mito-Flag was used for mitochondrial transgene expression in Saos-2, HepG2, HS-5, and HEK293 cells. Like the observation in HeLa cells, cells incubated with the baculoviral vectors alone produce fluorescence at the intended organelles of the encoding proteins (i.e., RFP-LAMP1 and GFP-PTS at lysosome and peroxisome, respectively). Notably, mixing Mito-Flag with the baculoviral vectors result in the gene expression exclusively in the mitochondria of two cancer cell lines, Saos-2 and HepG2 cells (FIGS. 25I and 25J). For the two noncancerous cell lines, HS-5 (FIG. 25K) and HEK293, mixing Mito-Flag with the gene vectors (virus or plasmid) hardly yields mitochondrial exclusive gene expression. These results indicate that the Mito-Flag perimitochondrial ENS enables mitochondrial transgene expression in a cancer cell specific manner.

Example 17—Analyzing Mechanism of Action and Reasons for Cancer Cell Specificity While M-β-CD (Le et al., "Caveolin-1 is a Negative Regulator of Caveolae-Mediated Endocytosis to the Endoplasmic Reticulum," *J. Biol. Chem.* 277:3371-3379 (2002), which is hereby incorporated by reference in its entirety) hardly affects the uptake of NBD-Mito-Flag, chlorpromazine (CPZ) (Wang et al., "Mis-Assembly of Clathrin Lattices on Endosomes Reveals a Regulatory Switch for Coated Pit Formation," *J. Cell Biol.* 123:1107-1117 (1993), which is hereby incorporated by reference in its entirety) significantly decreases the intracellular fluorescence of NBD-Mito-Flag, indicating that the uptake of Mito-Flag mainly relies on clathrin-dependent endocytosis (FIG. 26A). The pretreatment of chloroquine, an inhibitor of endosomal acidification, results in significantly reduced mitochondrial localization of NBD-Mito-Flag in HeLa cells (FIG. 26B), indicating that the pH-buffering effect (Varkouhi et al.,"Endosomal Escape Pathways for Delivery of Biologicals," *J. Controlled Release* 151:220-228 (2011), which is hereby incorporated by reference in its entirety) of the carboxylic groups in Flag-tag facilitate the endosomal escape.

Given the results in Example 16, the amount of ENTK on the mitochondria isolated from HeLa, HS-5, and HEK293 cells was examined (FIG. 26C). ENTK presents in the mitochondria isolated from these three cell lines, but HeLa mitochondria have much a higher level of ENTK than those of HS-5 and HEK293 cells. This result agrees with the cancer-cell specificity of the mitochondria-localized nanoparticle-to-nanofiber transition (FIG. 26D) and gene transfection. ENTK-knockdown HeLa cells were generated via siRNA-mediated gene silencing, and this substantially reduces the accumulation of NBD-Mito-Flag in the mitochondria of the HeLa cells (FIG. 26E) compared to the cells treated by the siRNA for non-target control. Besides, the ENTK-knockdown HeLa cells yield much more non-mitochondrial fluorescence after Mito-Flag-assisted baculoviral transfection compared to those in the control (FIG. 26F), suggesting a diminished mitochondrial specificity.

Besides enzymatic conversion of the micelles of Mito-Flag to nanofibers, the electrostatic interaction between Mito-Flag and VDAC (voltage-dependent anion channel) on mitochondrial surface favors the mitochondria-specific attachment, similar to the tubulin-VDAC binding through the negatively charged C-terminal tails of tubulin (Rostovtseva et al., "Tubulin Binding Blocks Mitochondrial Voltage-Dependent Anion Channel and Regulates Respiration," *Proc. Natl. Acad. Sci.* 105:18746-18751 (2008), which is hereby incorporated by reference in its entirety). Two experiments indicated that blocking VDAC antagonizes the Mito-Flag from approaching mitochondria: Erastin, a VDAC-targeting blocker, decreases the accumulation of NBD-Mito-Flag and reduces the localization of RFP-LAMP1 (transfected by Mito-Flag) in mitochondria (FIG. 26G-26H), cells incubated with nocodazole (Ndz), a microtubule destabilizer to increase free tubulin, exhibit weakened mitochondrial fluorescence from NBD-Mito-Flag (FIG. 26I). Moreover, the pretreatment of FCCP (p-trifluoromethoxy carbonylcyanide phenylhydrazone) (Johnson et al., "Monitoring of Relative Mitochondrial Membrane Potential in Living Cells by Fluorescence Microscopy," *J Cell Biol.* 88:526-535 (1981), which is hereby incorporated by reference in its entirety), a drug that dissipates mitochondrial membrane potential and proton gradient, diminishes the mitochondria-specific localization and gene transfection by Mito-Flag perimitochondrial ENS, indicating that mitochondrial membrane potential and proton gradient contribute to the mitochondrial targeting of Mito-Flag perimitochondrial ENS (FIG. 27).

Discussion of Examples 11-19

Acting differently from the cationic cell penetrating peptides (Filipovaka et al., "Cell-Penetrating Peptides Do Not Cross Mitochondrial Membranes Even When Conjugated to a Lipophilic Cation: Evidence Against Direct Passage Through Phospholipid Bilayers," *Biochem. Journal* 383: 457-468 (2004), which is hereby incorporated by reference in its entirety), Mito-Flag, as an enzyme-responsive, negative-charged peptide, forms micelles and undergoes ENTK-induced morphology/phase transition on mitochondria. This perimitochondrial ENS process promotes DNA import into mitochondria, including plasmids and viral vectors. Notably, local enzymatic reaction converting micelles of Mito-Flag to nanofibers for mitochondrial targeting sidesteps the need of mitochondrial protein import sequence (although that may optionally be used to minimize cytosolic retention of any mislocalized expression products). Additionally, the cancer cell specific mitochondria DNA import via the Mito-Flag perimitochondrial ENS implies a new non-genetic difference between the mitochondria of cancer and normal cells. This strategy promises the development of new genetic therapeutics for cancer treatment. The stability of the Mito-Flag micelles in more complex environments, such as in vivo, will confirm the utility of Mito-Flag for cancer therapy. Illustrating perimitochondrial ENS to facilitate genetic engineering of mitochondria in cancer, this work offers a versatile and robust strategy for selectively targeting the mitochondria of cancer cells and for manipulating the metabolism of cancer cells.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A pharmaceutical composition comprising:
   an aqueous medium;
   a nucleic acid construct or recombinant viral vector; and
   a branched peptide comprising a first peptide chain and a second peptide chain having its C-terminal amino acid covalently linked to a sidechain of a lysine or cysteine residue of the first peptide chain,
   wherein the first peptide chain comprises a plurality of aromatic amino acids and an aromatic group linked to an amino terminus of the first peptide chain, and comprises the amino acid sequence of FFKY (SEQ ID NO: 1), FFFKY (SEQ ID NO: 2), FFGKY (SEQ ID NO: 3), FFGK (SEQ ID NO: 4), FFGKF (SEQ ID NO: 5), ffky, fffky, ffgky, ffgk, ffgkf, FFK(Dmt) (SEQ ID NO: 6), FFFK(Dmt) (SEQ ID NO: 7), FFGK(Dmt) (SEQ ID NO: 8), ffk(dmt), fffk(dmt), ffgk(dmt), FFCY (SEQ ID NO: 9), FFFCY (SEQ ID NO: 10), FFGCY (SEQ ID NO: 11), FFGC (SEQ ID NO: 12), FFGCF (SEQ ID NO: 13), ffcy, fffcy, ffgcy, ffgc, ffgcf, FFC(Dmt) (SEQ ID NO: 14), FFFC(Dmt) (SEQ ID NO: 15), FFGC(Dmt) (SEQ ID NO: 16), ffc(dmt), fffc(dmt), ffgc(dmt), wherein Dmt is 2,6-dimethyl-L-tyrosine and dmt is 2,6-dimethyl-D-tyrosine; and
   wherein the second peptide chain comprises a plurality of hydrophilic amino acids and an enzyme cleavage site, and comprises the amino acid sequence of DDDDK (SEQ ID NO: 17), KDDDK (SEQ ID NO: 18), DDDDR (SEQ ID NO: 19), KDDDR (SEQ ID NO: 20), DADDK (SEQ ID NO: 21), KADDK (SEQ ID NO: 22), DADDR (SEQ ID NO: 23), KADDR (SEQ ID NO: 24), DEDDK (SEQ ID NO: 25), KEDDK (SEQ ID NO: 26), DEDDR (SEQ ID NO: 27), KEDDR (SEQ ID NO: 28), EDDDK (SEQ ID NO: 29), EDDDR (SEQ ID NO: 30), EEDDK (SEQ ID NO: 31), EEDDR (SEQ ID NO: 32), DLYDDDDK (SEQ ID NO: 33), DLYDDDDR (SEQ ID NO: 34), DYKDDDDK (SEQ ID NO: 35), DYKDDDDR (SEQ ID NO: 36), DYKDADDK (SEQ ID NO: 37), DYKDADDR (SEQ ID NO: 38), DYKDEDDK (SEQ ID NO: #39), DYKDEDDR (SEQ ID NO: 40), DYKEDDDK (SEQ ID NO: 41), DYKEDDDR (SEQ ID NO: 42), DYKEEDDK (SEQ ID NO: 43), DYKEEDDR (SEQ ID NO: 44), or LKGDR (SEQ ID NO: 45);
   wherein the branched peptide is associated with the nucleic acid construct or recombinant viral vector in the aqueous medium.

2. The pharmaceutical composition according to claim 1, wherein the nucleic acid construct is present.

3. The pharmaceutical composition according to claim 2, wherein the nucleic acid construct is a plasmid comprising a transgene.

4. The pharmaceutical composition according to claim 2, wherein the branched peptide forms micelle structures that contain the nucleic acid construct.

5. The pharmaceutical composition according to claim 1, wherein the recombinant viral vector is present.

6. The pharmaceutical composition according to claim 5, wherein the recombinant viral vector comprises a transgene.

7. The pharmaceutical composition according to claim 5, wherein the branched peptide forms micelle structures that decorate the recombinant viral vector.

8. The pharmaceutical composition according to claim 5, wherein the recombinant viral vector is a baculovirus, adenovirus (Ad5), adeno-associated virus (AAV2, 3, 5, 6, 8, 9), herpes simplex virus (HSV1), lentivirus (HIV-1, -2), retrovirus (MSV, MSCV), alphavirus (SFV, SIN, VEE, M1), flavivirus (Dengue, West Nile Kunjin), or rhabdovirus (rabies, VSV).

9. The pharmaceutical composition according to claim 3, wherein the transgene encodes an RNAi molecule or a protein whose expression in mitochondria disrupts mitochondrial function and promotes cellular apoptosis.

10. The pharmaceutical composition according to claim 9, wherein the transgene encodes FUNDC1, p53, p13 (FMC1), Nix, Diablo, Cytochrome C, Porin, and combinations thereof.

11. The pharmaceutical composition according to claim 9, wherein the transgene encodes CRISPR/Cas9 and gRNA for MT-COL MT-OO2, MT-OO3, MT-ATP6, MT-ATPS, MT-ND1, MT-ND2, MT-ND3, MT-ND4, MT-ND5, MT-ND6, or combinations thereof.

12. The pharmaceutical composition according to claim 1, wherein the first peptide chain comprises the aromatic group linked to the amino terminus of the first peptide chain.

13. The pharmaceutical composition according to claim 12, wherein the aromatic group is selected from the group consisting of phenylacetyl, naphthylacetyl, fluorenylacetyl, pyrenylacetyl, and cinnamoyl.

14. The pharmaceutical composition according to claim 1, wherein the plurality of aromatic amino acids are selected from the group consisting of phenylalanine, tyrosine, and tryptophan.

15. The pharmaceutical composition according to claim 1, wherein the amino acid residue having the sidechain covalently linked to the C-terminal amino acid of the second peptide chain is:
   (i) Lys, and the covalent bond is —NH—C(O)—; or
   (ii) Cys, and the covalent bond is —S—C(O)—.

16. The pharmaceutical composition according to claim 1, wherein the first peptide chain is selected from the group consisting of napthylacetyl-FFKY (SEQ ID NO: 1), napthylacetyl-FFFKY (SEQ ID NO: 2), napthylacetyl-FFGKY (SEQ ID NO: 3), napthylacetyl-FFGK (SEQ ID NO: 4), napthylacetyl-FFGKF (SEQ ID NO: 5), napthylacetyl-ffky, napthylacetyl-fffky, napthylacetyl-ffgky, napthylacetyl-ffgk, napthylacetyl-ffgkf, napthylacetyl-FFK(Dmt) (SEQ ID NO: 6), napthylacetyl-FFFK(Dmt) (SEQ ID NO: 7), napthylacetyl-FFGK(Dmt) (SEQ ID NO: 8), napthylacetyl-ffk(dmt), napthylacetyl-fffk(dmt), napthylacetyl-ffgk(dmt), wherein Dmt is 2,6-dimethyl-L-tyrosine and dmt is 2,6-dimethyl-D-tyrosine.

17. The pharmaceutical composition according to claim 1, wherein the second peptide chain comprises an enterokinase cleavage site.

18. The pharmaceutical composition according to claim 1, wherein the second peptide chain comprises a single amino acid residue between the cleavage site and the covalent bond, where the single amino acid is other than Trp or Pro.

19. The pharmaceutical composition according to claim 1, wherein the second peptide chain comprises the amino acid sequence of DDDDK (SEQ ID NO: 17), KDDDK (SEQ ID NO: 18), DDDDR (SEQ ID NO: 19), KDDDR (SEQ ID NO: 20), DYKDDDDK (SEQ ID NO: 35), or DYKDDDDR (SEQ ID NO: 36).

20. The pharmaceutical composition according to claim 1, wherein
   the second peptide chain comprising the amino acid sequence of SEQ ID NO: 17 is DDDDK(G/A/T/S/Y/H/Q/E/N/D/R/K) (SEQ ID NO: 46), or
   the second peptide chain comprising the amino acid sequence of SEQ ID NO: 18 is KDDDK(G/A/T/S/Y/H/Q/E/N/D/R/K) (SEQ ID NO: 47), or the second peptide chain comprising the amino acid sequence of SEQ ID NO: 19 is DDDDR(G/A/T/S/Y/H/Q/E/N/D/R/K) (SEQ ID NO: 48), or the second peptide chain comprising the amino acid sequence of SEQ ID NO: 20 is KDDDR(G/A/T/S/Y/H/Q/E/N/D/R/K) (SEQ ID NO: 49), or the second peptide chain comprising the amino acid sequence of SEQ ID NO: 21 is DADDK(G/A/T/S/Y/H/Q/E/N/D/R/K) (SEQ ID NO: 50), or the second peptide chain comprising the amino acid sequence of SEQ ID NO: 22 is KADDK(G/A/T/S/Y/H/Q/E/N/D/R/K) (SEQ ID NO: 51), or the second peptide chain comprising the amino acid sequence of SEQ ID NO: 23 is DADDR(G/A/T/S/Y/H/Q/E/N/D/R/K) (SEQ ID NO: 52), or the second peptide chain comprising the amino acid sequence of SEQ ID NO: 24 is KADDR(G/A/T/S/Y/H/Q/E/N/D/R/K) (SEQ ID NO: 53), or the second peptide chain comprising the amino acid sequence of SEQ ID NO: 25 is DEDDK(G/A/T/S/Y/H/Q/E/N/D/R/K) (SEQ ID NO: 54), or the second peptide chain comprising the amino acid sequence of SEQ ID NO: 26 is KEDDK(G/A/T/S/Y/H/Q/E/N/D/R/K) (SEQ ID NO: 55), or the second peptide chain comprising the amino acid sequence of SEQ ID NO: 27 is DEDDR(G/A/T/S/Y/H/Q/E/N/D/R/K) (SEQ ID NO: 56), or the second peptide chain comprising the amino acid sequence of SEQ ID NO: 28 is KEDDR(G/A/T/S/Y/H/Q/E/N/D/R/K) (SEQ ID NO: 57), or the second peptide chain comprising the amino acid sequence of SEQ ID NO: 29 is EDDDK(G/A/T/S/Y/H/Q/E/N/D/R/K) (SEQ ID NO: 58), or the second peptide chain comprising the amino acid sequence of SEQ ID NO: 30 is EDDDR(G/A/T/S/Y/H/Q/E/N/D/R/K) (SEQ ID NO: 59), or the second peptide chain comprising the amino acid sequence of SEQ ID NO: 31 is EEDDK(G/A/T/S/Y/H/Q/E/N/D/R/K) (SEQ ID NO: 60), or the second peptide chain comprising the amino acid sequence of SEQ ID NO: 32 is EEDDR(G/A/T/S/Y/H/Q/E/N/D/R/K) (SEQ ID NO: 61), or the second peptide chain comprising the amino acid sequence of SEQ ID NO: 33 is DLYDDDDK(G/A/T/S/Y/H/Q/E/N/D/R/K) (SEQ ID NO: 62), or the second peptide chain comprising the amino acid sequence of SEQ ID NO: 34 is DLYDDDDR(G/A/T/S/Y/H/Q/E/N/D/R/K) (SEQ ID NO: 63), or the second peptide chain comprising the amino acid sequence of SEQ ID NO: 35 is DYKDDDDK(G/A/T/S/Y/H/Q/E/N/D/R/K) (SEQ ID NO: 64), or the second peptide chain comprising the amino acid sequence of SEQ ID NO: 36 is DYKDDDDR(G/A/T/S/Y/H/Q/E/N/D/R/K) (SEQ ID NO: 65), or the second peptide chain comprising the amino acid sequence of SEQ ID NO: 37 is DYKDADDK(G/A/T/S/Y/H/Q/E/N/D/R/K) (SEQ ID NO: 66), or the second peptide chain comprising the amino acid sequence of SEQ ID NO: 38 is DYKDADDR(G/A/T/S/Y/H/Q/E/N/D/R/K) (SEQ ID NO: 67), or the second peptide chain comprising the amino acid sequence of SEQ ID NO: 39 is DYKDEDDK(G/A/T/S/Y/H/Q/E/N/D/R/K) (SEQ ID NO: 68), or the second peptide chain comprising the amino acid sequence of SEQ ID NO: 40 is DYKDEDDR(G/A/T/S/Y/H/Q/E/N/D/R/K) (SEQ ID NO: 69), or the second peptide chain comprising the amino acid sequence of SEQ ID NO: 41 is DYKEDDDK(G/A/T/S/Y/H/Q/E/N/D/R/K) (SEQ ID NO: 70), or the second peptide chain comprising the amino acid sequence of SEQ ID NO: 42 is DYKEDDDR(G/A/T/S/Y/H/Q/E/N/D/R/K) (SEQ ID NO: 71), or the second peptide chain comprising the amino acid sequence of SEQ ID NO: 43 is DYKEEDDK(G/A/T/S/Y/H/Q/E/N/D/R/K) (SEQ ID NO: 72), or the second peptide chain comprising the amino acid sequence of SEQ ID NO: 44 is DYKEEDDR(G/A/T/S/Y/H/Q/E/N/D/R/K) (SEQ ID NO: 73), or the second peptide chain comprising the amino acid sequence of SEQ ID NO: 45 is LKGDR(G/A/T/S/Y/H/Q/E/N/D/R/K) (SEQ ID NO: 74).

21. The pharmaceutical composition according to claim 1, wherein the branched peptide is selected from the group consisting of:

```
Nap-FFK(εG-KDDDDKYD-NH₂)Y,

Nap-ffk(εG-KDDDDKYD-NH₂)y,

Nap-FFK(εG-RDDDDKYD-NH₂)Y,

Nap-ffk(εG-RDDDDKYD-NH₂)y,

Nap-FFK(εG-KDDDDKYD-NH₂)(Dmt),

Nap-ffk(εG-KDDDDKYD-NH₂)(dmt),

Nap-FFK(εG-RDDDDKYD-NH₂)(Dmt),

Nap-ffk(εG-RDDDDKYD-NH₂)(dmt),

Nap-FFK(εG-KDDDDK(Dmt)D-NH₂)Y,

Nap-ffk(εG-KDDDDK(Dmt)D-NH₂)y,

Nap-FFK(εG-RDDDDK(Dmt)D-NH₂)Y,

Nap-ffk(εG-RDDDDK(Dmt)D-NH₂)y,

Nap-FFK(εG-KDDDDK(Dmt)D-NH₂)(Dmt),

Nap-ffk(εG-KDDDDK(Dmt)D-NH₂)(dmt),

Nap-FFK(εG-RDDDDK(Dmt)D-NH₂)(Dmt),
```
and
```
Nap-ffk(εG-RDDDDK(Dmt)D-NH₂)(dmt),
``` wherein Dmt is 2,6-dimethyl-L-tyrosine and dmt is 2,6-dimethyl-D-tyrosine.

* * * * *

UNITED STATES PATENT AND TRADEMARK OFFICE
CERTIFICATE OF CORRECTION

PATENT NO. : 11,834,517 B2
APPLICATION NO. : 17/537418
DATED : December 5, 2023
INVENTOR(S) : He et al.

It is certified that error appears in the above-identified patent and that said Letters Patent is hereby corrected as shown below:

In the Claims

In Claim 11, at Column 84, Line 14, delete "MT-COL, MT-0O2, MT-0O3" and insert --MT-CO1, MT-CO2, MT-CO3--.

Signed and Sealed this
Fourth Day of June, 2024

Katherine Kelly Vidal
*Director of the United States Patent and Trademark Office*

SEQUENCE LISTING

<160> NUMBER OF SEQ ID NOS: 86

<210> SEQ ID NO 1
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 1

Xaa Phe Lys Tyr
1

<210> SEQ ID NO 2
<211> LENGTH: 5
<212> TYPE: PRT
<213> ORGANISM: Artificial
<220> FEATURE:
<223> OTHER INFORMATION: Hydrogelator
<220> FEATURE:

```
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 2

Xaa Phe Phe Lys Tyr
1               5

<210> SEQ ID NO 3
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 3

Xaa Phe Gly Lys Tyr
1               5

<210> SEQ ID NO 4
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 4

Xaa Phe Gly Lys
1

<210> SEQ ID NO 5
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 5

Xaa Phe Gly Lys Phe
1               5

<210> SEQ ID NO 6
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (4)..(4)
```

```
<223> OTHER INFORMATION: Xaa at position 4 is 2,6-dimethyl-L-tyrosine

<400> SEQUENCE: 6

Xaa Phe Lys Xaa
1

<210> SEQ ID NO 7
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (5)..(5)
<223> OTHER INFORMATION: Xaa at position 5 is 2,6-dimethyl-L-tyrosine

<400> SEQUENCE: 7

Xaa Phe Phe Lys Xaa
1               5

<210> SEQ ID NO 8
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (5)..(5)
<223> OTHER INFORMATION: Xaa at position 5 is 2,6-dimethyl-L-tyrosine

<400> SEQUENCE: 8

Xaa Phe Gly Lys Xaa
1               5

<210> SEQ ID NO 9
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 9

Xaa Phe Cys Tyr
1

<210> SEQ ID NO 10
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
```

```
<223> OTHER INFORMATION: Xaa at position 1 is N-napthylacetyl-
      phenylalanine

<400> SEQUENCE: 10

Xaa Phe Phe Cys Tyr
1               5

<210> SEQ ID NO 11
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 11

Xaa Phe Gly Cys Tyr
1               5

<210> SEQ ID NO 12
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 12

Xaa Phe Gly Cys
1

<210> SEQ ID NO 13
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 13

Xaa Phe Gly Cys Phe
1               5

<210> SEQ ID NO 14
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (4)..(4)
<223> OTHER INFORMATION: Xaa at position at position 4 is 2,6-dimethyl-
      L-tyrosine
```

<400> SEQUENCE: 14

Xaa Phe Cys Xaa
1

<210> SEQ ID NO 15
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (5)..(5)
<223> OTHER INFORMATION: Xaa at position 5 is 2,6-dimethyl-L-tyrosine

<400> SEQUENCE: 15

Xaa Phe Phe Cys Xaa
1               5

<210> SEQ ID NO 16
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (5)..(5)
<223> OTHER INFORMATION: Xaa at position 5 is 2,6-dimethyl-L-tyrosine

<400> SEQUENCE: 16

Xaa Phe Gly Cys Xaa
1               5

<210> SEQ ID NO 17
<211> LENGTH: 5
<212> TYPE: PRT
<213> ORGANISM: Artificial
<220> FEATURE:
<223> OTHER INFORMATION: Hydrophilic tag

<400> SEQUENCE: 17

Asp Asp Asp Asp Lys
1               5

<210> SEQ ID NO 18
<211> LENGTH: 5
<212> TYPE: PRT
<213> ORGANISM: Artificial
<220> FEATURE:
<223> OTHER INFORMATION: Hydrophilic tag

<400> SEQUENCE: 18

Lys Asp Asp Asp Lys
1               5

<210> SEQ ID NO 19
<211> LENGTH: 5

```
<212> TYPE: PRT
<213> ORGANISM: Artificial
<220> FEATURE:
<223> OTHER INFORMATION: Hydrophilic tag

<400> SEQUENCE: 19

Asp Asp Asp Asp Arg
1               5

<210> SEQ ID NO 20
<211> LENGTH: 5
<212> TYPE: PRT
<213> ORGANISM: Artificial
<220> FEATURE:
<223> OTHER INFORMATION: Hydrophilic tag

<400> SEQUENCE: 20

Lys Asp Asp Asp Arg
1               5

<210> SEQ ID NO 21
<211> LENGTH: 5
<212> TYPE: PRT
<213> ORGANISM: Artificial
<220> FEATURE:
<223> OTHER INFORMATION: Hydrophilic tag

<400> SEQUENCE: 21

Asp Ala Asp Asp Lys
1               5

<210> SEQ ID NO 22
<211> LENGTH: 5
<212> TYPE: PRT
<213> ORGANISM: Artificial
<220> FEATURE:
<223> OTHER INFORMATION: Hydrophilic tag

<400> SEQUENCE: 22

Lys Ala Asp Asp Lys
1               5

<210> SEQ ID NO 23
<211> LENGTH: 5
<212> TYPE: PRT
<213> ORGANISM: Artificial
<220> FEATURE:
<223> OTHER INFORMATION: Hydrophilic tag

<400> SEQUENCE: 23

Asp Ala Asp Asp Arg
1               5

<210> SEQ ID NO 24
<211> LENGTH: 5
<212> TYPE: PRT
<213> ORGANISM: Artificial
<220> FEATURE:
<223> OTHER INFORMATION: Hydrophilic tag

<400> SEQUENCE: 24

Lys Ala Asp Asp Arg
1               5

<210> SEQ ID NO 25
<211> LENGTH: 5
<212> TYPE: PRT
```

```
<213> ORGANISM: Artificial
<220> FEATURE:
<223> OTHER INFORMATION: Hydrophilic tag

<400> SEQUENCE: 25

Asp Glu Asp Asp Lys
1               5

<210> SEQ ID NO 26
<211> LENGTH: 5
<212> TYPE: PRT
<213> ORGANISM: Artificial
<220> FEATURE:
<223> OTHER INFORMATION: Hydrophilic tag

<400> SEQUENCE: 26

Lys Glu Asp Asp Lys
1               5

<210> SEQ ID NO 27
<211> LENGTH: 5
<212> TYPE: PRT
<213> ORGANISM: Artificial
<220> FEATURE:
<223> OTHER INFORMATION: Hydrophilic tag

<400> SEQUENCE: 27

Asp Glu Asp Asp Arg
1               5

<210> SEQ ID NO 28
<211> LENGTH: 5
<212> TYPE: PRT
<213> ORGANISM: Artificial
<220> FEATURE:
<223> OTHER INFORMATION: Hydrophilic tag

<400> SEQUENCE: 28

Lys Glu Asp Asp Arg
1               5

<210> SEQ ID NO 29
<211> LENGTH: 5
<212> TYPE: PRT
<213> ORGANISM: Artificial
<220> FEATURE:
<223> OTHER INFORMATION: Hydrophilic tag

<400> SEQUENCE: 29

Glu Asp Asp Asp Lys
1               5

<210> SEQ ID NO 30
<211> LENGTH: 5
<212> TYPE: PRT
<213> ORGANISM: Artificial
<220> FEATURE:
<223> OTHER INFORMATION: Hydrophilic tag

<400> SEQUENCE: 30

Glu Asp Asp Asp Arg
1               5

<210> SEQ ID NO 31
<211> LENGTH: 5
<212> TYPE: PRT
<213> ORGANISM: Artificial
```

```
<220> FEATURE:
<223> OTHER INFORMATION: Hydrophilic tag

<400> SEQUENCE: 31

Glu Glu Asp Asp Lys
1               5

<210> SEQ ID NO 32
<211> LENGTH: 5
<212> TYPE: PRT
<213> ORGANISM: Artificial
<220> FEATURE:
<223> OTHER INFORMATION: Hydrophilic tag

<400> SEQUENCE: 32

Glu Glu Asp Asp Arg
1               5

<210> SEQ ID NO 33
<211> LENGTH: 8
<212> TYPE: PRT
<213> ORGANISM: Artificial
<220> FEATURE:
<223> OTHER INFORMATION: Hydrophilic tag

<400> SEQUENCE: 33

Asp Leu Tyr Asp Asp Asp Asp Lys
1               5

<210> SEQ ID NO 34
<211> LENGTH: 8
<212> TYPE: PRT
<213> ORGANISM: Artificial
<220> FEATURE:
<223> OTHER INFORMATION: Hydrophilic tag

<400> SEQUENCE: 34

Asp Leu Tyr Asp Asp Asp Asp Arg
1               5

<210> SEQ ID NO 35
<211> LENGTH: 8
<212> TYPE: PRT
<213> ORGANISM: Artificial
<220> FEATURE:
<223> OTHER INFORMATION: Hydrophilic tag

<400> SEQUENCE: 35

Asp Tyr Lys Asp Asp Asp Asp Lys
1               5

<210> SEQ ID NO 36
<211> LENGTH: 8
<212> TYPE: PRT
<213> ORGANISM: Artificial
<220> FEATURE:
<223> OTHER INFORMATION: Hydrophilic tag

<400> SEQUENCE: 36

Asp Tyr Lys Asp Asp Asp Asp Arg
1               5

<210> SEQ ID NO 37
<211> LENGTH: 8
<212> TYPE: PRT
<213> ORGANISM: Artificial
<220> FEATURE:
```

```
<223> OTHER INFORMATION: Hydrophilic tag

<400> SEQUENCE: 37

Asp Tyr Lys Asp Ala Asp Asp Lys
1               5

<210> SEQ ID NO 38
<211> LENGTH: 8
<212> TYPE: PRT
<213> ORGANISM: Artificial
<220> FEATURE:
<223> OTHER INFORMATION: Hydrophilic tag

<400> SEQUENCE: 38

Asp Tyr Lys Asp Ala Asp Asp Arg
1               5

<210> SEQ ID NO 39
<211> LENGTH: 8
<212> TYPE: PRT
<213> ORGANISM: Artificial
<220> FEATURE:
<223> OTHER INFORMATION: Hydrophilic tag

<400> SEQUENCE: 39

Asp Tyr Lys Asp Glu Asp Asp Lys
1               5

<210> SEQ ID NO 40
<211> LENGTH: 8
<212> TYPE: PRT
<213> ORGANISM: Artificial
<220> FEATURE:
<223> OTHER INFORMATION: Hydrophilic tag

<400> SEQUENCE: 40

Asp Tyr Lys Asp Glu Asp Asp Arg
1               5

<210> SEQ ID NO 41
<211> LENGTH: 8
<212> TYPE: PRT
<213> ORGANISM: Artificial
<220> FEATURE:
<223> OTHER INFORMATION: Hydrophilic tag

<400> SEQUENCE: 41

Asp Tyr Lys Glu Asp Asp Asp Lys
1               5

<210> SEQ ID NO 42
<211> LENGTH: 8
<212> TYPE: PRT
<213> ORGANISM: Artificial
<220> FEATURE:
<223> OTHER INFORMATION: Hydrophilic tag

<400> SEQUENCE: 42

Asp Tyr Lys Glu Asp Asp Asp Arg
1               5

<210> SEQ ID NO 43
<211> LENGTH: 8
<212> TYPE: PRT
<213> ORGANISM: Artificial
<220> FEATURE:
<223> OTHER INFORMATION: Hydrophilic tag
```

```
<400> SEQUENCE: 43

Asp Tyr Lys Glu Glu Asp Asp Lys
1               5

<210> SEQ ID NO 44
<211> LENGTH: 8
<212> TYPE: PRT
<213> ORGANISM: Artificial
<220> FEATURE:
<223> OTHER INFORMATION: Hydrophilic tag

<400> SEQUENCE: 44

Asp Tyr Lys Glu Glu Asp Asp Arg
1               5

<210> SEQ ID NO 45
<211> LENGTH: 5
<212> TYPE: PRT
<213> ORGANISM: Artificial
<220> FEATURE:
<223> OTHER INFORMATION: Hydrophilic tag

<400> SEQUENCE: 45

Leu Lys Gly Asp Arg
1               5

<210> SEQ ID NO 46
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 46

Asp Asp Asp Asp Lys Xaa
1               5

<210> SEQ ID NO 47
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 47

Lys Asp Asp Asp Lys Xaa
1               5

<210> SEQ ID NO 48
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
```

```
      E, N, D, R, or K

<400> SEQUENCE: 48

Asp Asp Asp Asp Arg Xaa
1               5

<210> SEQ ID NO 49
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 49

Lys Asp Asp Asp Arg Xaa
1               5

<210> SEQ ID NO 50
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 50

Asp Ala Asp Asp Lys Xaa
1               5

<210> SEQ ID NO 51
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 51

Lys Ala Asp Asp Lys Xaa
1               5

<210> SEQ ID NO 52
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 52

Asp Ala Asp Asp Arg Xaa
1               5
```

```
<210> SEQ ID NO 53
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 53

Lys Ala Asp Asp Arg Xaa
1               5

<210> SEQ ID NO 54
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 54

Asp Glu Asp Asp Lys Xaa
1               5

<210> SEQ ID NO 55
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 55

Lys Glu Asp Asp Lys Xaa
1               5

<210> SEQ ID NO 56
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 56

Asp Glu Asp Asp Arg Xaa
1               5

<210> SEQ ID NO 57
<211> LENGTH: 6
<212> TYPE: PRT
<213> ORGANISM: Artificial
<220> FEATURE:
<223> OTHER INFORMATION: Hydrophilic tag
```

```
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 57

Lys Glu Asp Asp Arg Xaa
1               5

<210> SEQ ID NO 58
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 58

Glu Asp Asp Asp Lys Xaa
1               5

<210> SEQ ID NO 59
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 59

Glu Asp Asp Asp Arg Xaa
1               5

<210> SEQ ID NO 60
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 60

Glu Glu Asp Asp Lys Xaa
1               5

<210> SEQ ID NO 61
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 61
```

Glu Glu Asp Asp Arg Xaa
1               5

<210> SEQ ID NO 62
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 62

Asp Leu Tyr Asp Asp Asp Asp Lys Xaa
1               5

<210> SEQ ID NO 63
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 63

Asp Leu Tyr Asp Asp Asp Asp Arg Xaa
1               5

<210> SEQ ID NO 64
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 64

Asp Tyr Lys Asp Asp Asp Asp Lys Xaa
1               5

<210> SEQ ID NO 65
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 65

Asp Tyr Lys Asp Asp Asp Asp Arg Xaa
1               5

<210> SEQ ID NO 66
<211> LENGTH: 9

```
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 66

Asp Tyr Lys Asp Ala Asp Asp Lys Xaa
1               5

<210> SEQ ID NO 67
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 67

Asp Tyr Lys Asp Ala Asp Asp Arg Xaa
1               5

<210> SEQ ID NO 68
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 68

Asp Tyr Lys Asp Glu Asp Asp Lys Xaa
1               5

<210> SEQ ID NO 69
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 69

Asp Tyr Lys Asp Glu Asp Asp Arg Xaa
1               5

<210> SEQ ID NO 70
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
```

```
<223> OTHER INFORMATION: Xaa at position 9 can be G, A, T, S, Y, H, Q,
      E, N, D, R, or K

<400> SEQUENCE: 70

Asp Tyr Lys Glu Asp Asp Asp Lys Xaa
1               5

<210> SEQ ID NO 71
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 71

Asp Tyr Lys Glu Asp Asp Asp Arg Xaa
1               5

<210> SEQ ID NO 72
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 72

Asp Tyr Lys Glu Glu Asp Asp Lys Xaa
1               5

<210> SEQ ID NO 73
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 73

Asp Tyr Lys Glu Glu Asp Asp Arg Xaa
1               5

<210> SEQ ID NO 74
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 74

Leu Lys Gly Asp Arg Xaa
1               5
```

<210> SEQ ID NO 75
<211> LENGTH: 9
<212> TYPE: PRT
<213> ORGANISM: Artificial
<220> FEATURE:
<223> OTHER INFORMATION: Hydrophilic tag

<400> SEQUENCE: 75

Asp Tyr Lys Asp Asp Asp Asp Lys Gly
1               5

<210> SEQ ID NO 76
<211> LENGTH: 25
<212> TYPE: DNA
<213> ORGANISM: Artificial Sequence
<220> FEATURE:
<223> OTHER INFORMATION: CRISPR RNA recognition sequence
<220> FEATURE:
<221> NAME/KEY: misc_feature
<222> LOCATION: (3)..(23)
<223> OTHER INFORMATION: n is a, c, g, or t

<400> SEQUENCE: 76
ggnnnnnnnn nnnnnnnnnn nnngg                                    25

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
taagcaccct aatcaactgg c                                        21

<210> SEQ ID NO 78
<211> LENGTH: 21
<212> TYPE: DNA
<213> ORGANISM: Artificial Sequence
<220> FEATURE:
<223> OTHER INFORMATION: Primer

<400> SEQUENCE: 78
gcctccacta tagcagatgc g                                        21

<210> SEQ ID NO 79
<211> LENGTH: 25
<212> TYPE: DNA
<213> ORGANISM: Artificial Sequence
<220> FEATURE:
<223> OTHER INFORMATION: gRNA of MT-CO1, forward strand

<400> SEQUENCE: 79
caccgggccc agctcggctc gaata                                    25

<210> SEQ ID NO 80
<211> LENGTH: 25
<212> TYPE: DNA
<213> ORGANISM: Artificial Sequence
<220> FEATURE:
<223> OTHER INFORMATION: gRNA of MT-CO1, reverse strand

<400> SEQUENCE: 80
aaactattcg agccgagctg ggccc                                    25

```
<210> SEQ ID NO 81
<211> LENGTH: 25
<212> TYPE: DNA
<213> ORGANISM: Artificial Sequence
<220> FEATURE:
<223> OTHER INFORMATION: random gRNA, forward strand

<400> SEQUENCE: 81
caccgccaga gaagaagact actga                                              25

<210> SEQ ID NO 82
<211> LENGTH: 25
<212> TYPE: DNA
<213> ORGANISM: Artificial Sequence
<220> FEATURE:
<223> OTHER INFORMATION: random gRNA, reverse strand

<400> SEQUENCE: 82
aaactcagta gtcttcttct ctggc                                              25

<210> SEQ ID NO 83
<211> LENGTH: 66
<212> TYPE: DNA
<213> ORGANISM: Artificial Sequence
<220> FEATURE:
<223> OTHER INFORMATION: partial sequence of pGLO, forward strand

<400> SEQUENCE: 83
ggaaaactac ctgttccatg gccaacactt gtcactacac atggcatgga tgagctctac        60
aaataa                                                                   66

<210> SEQ ID NO 84
<211> LENGTH: 66
<212> TYPE: DNA
<213> ORGANISM: Artificial Sequence
<220> FEATURE:
<223> OTHER INFORMATION: partial sequence of pGLO, reverse strand

<400> SEQUENCE: 84
ttatttgtag agctcatcca ygccatgtgt agtgacaagt gttggccatg gaacaggtag        60
ttttcc                                                                   66

<210> SEQ ID NO 85
<211> LENGTH: 66
<212> TYPE: DNA
<213> ORGANISM: Artificial Sequence
<220> FEATURE:
<223> OTHER INFORMATION: partial sequence of Mito-pGLO, forward strand

<400> SEQUENCE: 85
ggaaaactac ctgttccatg accaacactt gtcactacac atggcatgga tgagctctac        60
aaaagg                                                                   66

<210> SEQ ID NO 86
<211> LENGTH: 66
<212> TYPE: DNA
<213> ORGANISM: Artificial Sequence
<220> FEATURE:
<223> OTHER INFORMATION: partial sequence of Mito-pGLO, reverse strand

<400> SEQUENCE: 86
ccttttgtag agctcatcca tgccatgtgt agtgacaagt gttggtcatg gaacaggtag        60
ttttcc                                                                   66
```